(12) United States Patent
Hamilton et al.

(10) Patent No.: US 12,337,058 B1
(45) Date of Patent: Jun. 24, 2025

(54) SUNSCREEN FORMULATIONS AND METHODS OF MAKING AND USING THE SAME

(71) Applicant: W.S. Badger Company, Gilsum, NH (US)

(72) Inventors: Rebecca Hamilton, Gilsum, NH (US); Flor Alvarez Mitre, Gilsum, NH (US)

(73) Assignee: W.S. Badger Company, Gilsum, NH (US)

( * ) Notice: Subject to any disclaimer, the term of this patent is extended or adjusted under 35 U.S.C. 154(b) by 0 days.

(21) Appl. No.: 18/444,424

(22) Filed: Feb. 16, 2024

(51) Int. Cl.
| | |
|---|---|
| *A61K 8/92* | (2006.01) |
| *A61K 8/27* | (2006.01) |
| *A61K 8/49* | (2006.01) |
| *A61K 8/73* | (2006.01) |
| *A61Q 17/04* | (2006.01) |

(52) U.S. Cl.
CPC ................ *A61K 8/922* (2013.01); *A61K 8/27* (2013.01); *A61K 8/498* (2013.01); *A61K 8/732* (2013.01); *A61K 8/927* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 10,758,475 B2 | 9/2020 | Ficko | |
| 2022/0287944 A1* | 9/2022 | Costache | ................ A61K 8/64 |

FOREIGN PATENT DOCUMENTS

| | | | | |
|---|---|---|---|---|
| WO | WO-2016048425 A1 * | 3/2016 | ........... | A61K 8/0229 |

OTHER PUBLICATIONS

ASTM International, "Standard Terminology Relating to Sensory Evaluations of Materials and Products, E253-09a", ASTM International, West Conshohocken, PA. E253-09a (2009) (2 pages).
Badger Online Product Brochure, "Active Mineral Sunscreen Cream—SPF 30", accessed/printed on Apr. 10, 2024 at: https://badgerbalm.com/products/clear-zinc-mineral-sunscreen-spf-30 (Apr. 2024) (12 pages).
Noren et al., "Differentiating between tackiness and stickiness and their induction in foods", *Trends in Food Science & Technology*, 2019, ISSN 0924-2244 (Abstract Only).

* cited by examiner

*Primary Examiner* — Nannette Holloman
(74) *Attorney, Agent, or Firm* — Clark & Elbing LLP

(57) ABSTRACT

Disclosed are sunscreen formulations, methods of producing the formulations, and methods of using the formulations, e.g., to reduce the risk of sun damage.

27 Claims, 46 Drawing Sheets

FIG. 1

Raw material selection for screening

OILS

| Fatty acid | No of C | Uns at | Frac Coconut (FCO) | Baba ssu (BAO) | Baoba b (BAO) | Sunflow er high oleic (SFO) | Canole (CAO) | Apricot (APO) | Rice (RO) | Sesa me (SEO) | Sunflo wer (SFO) | Grape seed (GSO) | Linsa ed (LSO) | Hemp (HEO) | Pom egra nate | Jojoba (JJO) | Abyssi nian (ABO) |
|---|---|---|---|---|---|---|---|---|---|---|---|---|---|---|---|---|---|
| Caprilic | 8 | 0 | 64% | 7% | | | | | | | | | | | | | |
| Capric | 10 | 0 | 34% | 8% | | | | | | | | | | | | | |
| Lauric | 12 | 0 | 2% | 47% | | | | | | | | | | | | | |
| Miristic | 14 | 0 | | 14% | | | | | | | | | | | | | |
| Palmitic | 16 | 0 | | 7% | 24% | 5% | 4% | 6% | 20% | 9% | 7% | 11% | 5% | 5% | 5% | 1% | 3% |
| Stearic | 18 | 0 | | 2% | 5% | 3% | 2% | 2% | | 5% | 2% | 5% | 5% | 2% | 3% | | |
| Oleic | 18 | 1 | 2% | 12% | 38% | 90% | 62% | 67% | 42% | 38% | 29% | 25% | 24% | 11% | 12% | 10% | 18% |
| Linoleic | 18 | 2 | | | 28% | 2% | 22% | 22% | 32% | 45% | 58% | 55% | 13% | 59% | 13% | | 11% |
| Linolenic | 18 | 3 | | | | | 10% | | | | | | 52% | 20% | | | 4% |
| Punicic | 18 | 3 | | | | | | | | | | | | | 65% | | |
| Gondoic | 20 | 1 | | | | | | | | | | | | | | 71% | 4% |
| Erucic | 22 | 1 | | | | | | | | | | | | | | 14% | 58% |

% of Average bibliography references

FIG. 7

Raw material selection for screening

Waxes

| Component | Candelilla (CLW) | Bees (BW) | Sunflower (SFW) | Rice bran (RW) | Carnauba (CUW) |
|---|---|---|---|---|---|
| Esters | 20-29% | 58-67% | 96% | 73% | 80-85% |
| Hydrocarbons | 50-70% | 14-27% | 0% | 22% | 1-3% |
| Free fatty acids | 7-9% | 9-12% | 3% | 0% | 3-4% |
| Alcohols | 12-14% | 1-6% | 0% | 4% | 2-3% |

FIG. 8

CGC summary

| Oil | Wax | | | | |
|-----|-----|-----|-----|-----|-----|
|     | CUW | RW | CW | BW | SFW |
| SFO | 4% | 5% | 2% | 3% | 1% |
| GSO | 4% | 5% | 2% | 3% | 1% |
| FCO | 3% | 7% | 3% | 14% | 1% |
| RO  | 4% | 5% | 2% | 3% | 1% |

FIG. 10

Thixotropy rapid test

| | Recovery | CUW | RW | CW | BW | SFW |
|---|---|---|---|---|---|---|
| SFO | After scooped | small layer trapped | small layer trapped | No sign of syneresis | small layer trapped | small layer trapped |
| | After sheared | No recovery | No recovery | Full recovery | Partial | Partial |
| GSO | After scooped | small layer trapped | No sign of syneresis | No sign of syneresis | small layer trapped | small layer trapped |
| | After sheared | No recovery | Partial | Full recovery | Full recovery | Partial |
| FCO | After scooped | small layer trapped | small layer trapped | small layer trapped | No sign of syneresis | No sign of syneresis |
| | After sheared | No recovery | No recovery | Partial | Full recovery | Partial |
| RO | After scooped | small layer trapped | small layer trapped | No sign of syneresis | small layer trapped | No sign of syneresis |
| | After sheared | No recovery | No recovery | Partial | Full recovery | Partial |

FIG. 12

Wax synergy study
WAX1+WAX2< CGC

| Oil:SFO | CUW | RW | SFW | BW | CW |
|---|---|---|---|---|---|
| BW | High viscosity | Liquid | High viscosity | Gel | |
| CW | High viscosity | Liquid | Liquid | | Gel |

| Oil:FCO | CUW | RW | SFW | BW | CW |
|---|---|---|---|---|---|
| BW | liquid | Liquid | Precipitation | Gel | |
| CW | High viscosity | High viscosity | Precipitation | | Gel |

FIG. 13

Gelation analysis

| Oil | 1%SFW | 0.5%BW+ 0.5%CW | 1.0%BW+ 0.5%CW | 1.0%BW +1%CW | 0.5%SFW +0.5%BW |
|---|---|---|---|---|---|
| HEMP | GEL | High viscosity | GEL | ------ | High viscosity |
| SEO | GEL | High viscosity | Partial Gel | GEL | Liquid |
| APO | GEL | GEL | ------ | ----- | High viscosity |
| FCO | GEL | GEL | GEL | GEL | Liquid |
| ABO | GEL | GEL | GEL | GEL | ---------- |

FIG. 23

SUMMARY OF SENSORIAL RESULTS

FORMULATION RATING

| Formulation | Oil during application | Oily absorption during | Visual graininess | Roughness | Yield | Spreadability | Total |
|---|---|---|---|---|---|---|---|
| F1 | 4 | 3 | 2 | 4 | 4 | 3 | 20 |
| F2 | 0 | 0 | 0 | 0 | 0 | 0 | 0 |
| F3 | 0 | 0 | 1 | 3 | 2 | 3 | 9 |
| *F4 | 0 | 0 | 0 | 0 | 3 | 4 | 7 |
| F5 | 0 | 0 | 0 | 0 | 0 | 0 | 0 |
| *F6 | 3 | 0 | 0 | 0 | 0 | 0 | 0 |
| F7 | 0 | 2 | 3 | 2 | 2 | 0 | 10 |
| F8 | 3 | 4 | 0 | 0 | 0 | 0 | 2 |
| F9 | 3 | 1 | 4 | 3 | 0 | 3 | 15 |
| F10 | | | 0 | 0 | 0 | 0 | 4 |

*Samples with syneresis observed

FIG. 24

Process modification

Ensure proper ZnO dispersion
Explore a softer and more pleasant skin feel

| Label | Filling Temperature | No of Homogenization steps |
|---|---|---|
| F1-62°C (H70) | 62 | 2 (84 & 70°C) |
| F1-62°C (H65) | 62 | 2 (84 & 65°C) |
| F1-57°C (H66)* | 57 | 2 (84 & 66°C) |
| F1-59°C (H66) | 59 | 2 (84 & 66°C) |
| F1-60°C (H70+H63) | 60 | 3 (84 & 70 & 63°C-3 min) |
| F1-60°C (H70+H63†) | 60 | 3 (84 & 70 & 63°C-5 min) |
| F1-58°C (H70+H63) | 58 | 3 (84 & 70 & 63°C-3 min) |

The lower the filling temperature the softer the sensation

*Sample presented syneresis after 2 days at RT

F1 Crystallization DSC

F1 Melting DSC

POLARIZED PHOTOMICROGRAPHS

FIG. 33

Thermal parameters
Adjustment of NSFW (new sunflower wax)

Crystallization Parameters - T (°C)

| F1 (sunflower wax) | $T_{cr,start}$ | $T_{cr1}$ | $T_{cr2}$ | $T_{cr3}$ | $T_{cr-end}$ | Enthalpy J/g |
|---|---|---|---|---|---|---|
| SFW | 65 | 63 | 62 | 57 | 39 | 7.6 |
| NSFW | 63 | 62 | 56 | Between 56-32 | 38 | 8.7 |

Melting Parameters - T (°C)

| F1 (sunflower wax) | $T_{M,start}$ | $T_{M1}$ | $T_{M2}$ | $T_{M3}$ | $T_{M,end}$ | Enthalpy J/g |
|---|---|---|---|---|---|---|
| SFW | 43 | 61 | 65 | 68 | 70 | 4.7 |
| NSFW | 39 | 60 | 63 | 66 | 67 | 8.4 |

SUNSCREEN FORMULATIONS AND METHODS OF MAKING AND USING THE SAME

BACKGROUND

Commercially available sunscreens often require emulsifiers, preservatives, or stabilizers to make them sufficiently stable for storage, distribution, and use. These emulsifiers, preservatives, or stabilizers can have detrimental effects on the user and the environment, and they provide little to no added protection from the sun. Creating storage-, transport-, and shelf-stable sunscreens without these emulsifiers, preservatives, and/or stabilizers, and that also contain low weight percent loading of wax relative to other commercially available sunscreens, which are texturally pleasant and provide users with a satisfying topical experience has proven challenging.

Thus, there is a need in the field for improved sunscreen formulations.

SUMMARY

Disclosed herein are compositions (e.g., sunscreen formulations), methods of producing the compositions, and methods of using the compositions (e.g., to reduce the risk of sun damage to the skin). The compositions can be shelf-stable organogels that do not separate into their constituent oils, waxes, zinc oxide particles, or additives over time (e.g., after a time of 6 months to give years) and that is capable of being smeared without compromising its original structure (oleogel) with no other chemical emulsifiers, preservatives, or stabilizers. The compositions also contain low weight percent of wax relative to other commercially available sunscreens (e.g., 10 wt % or less).

In a first aspect, the disclosure features a composition including an oil component, a wax component, a broad spectrum UV absorber, and an additive component, wherein the composition includes between 50 wt % and 90 wt % of the oil component, between 0.1 wt % and 10 wt % of the wax component, between 0 wt % and 20 wt % of the additive component, and between 10 wt % and 30 wt % of a broad spectrum UV absorber, such as zinc oxide (ZnO). In some embodiments, the composition contains 0 wt % to 5 wt % water (e.g., water naturally associated with a wax or oil component). In some embodiments, the composition lacks an emulsifier, preservative, and/or stabilizer.

In some embodiments, the composition consists of or consists essentially of the oil component, the wax component, the broad spectrum UV absorber (e.g., ZnO), and the additive component.

In some embodiments, the oil component includes coconut oil, fractionated coconut oil, medium chain triglycerides (MCT oil), babassu oil, baobab oil, sunflower oil, canola oil, apricot oil, rice oil, sesame oil, grapeseed oil, linseed oil, hemp oil, pomegranate oil, jojoba oil, Abyssinian seed oil, a mixture of alkanes of vegetable origin, or any combination thereof. In some embodiments, the oil component includes a first oil and a second oil, in which a ratio of the first oil and the second oil is between 1:100 wt/wt to 100:1 wt/wt. In some embodiments, the wax component includes candelilla wax, beeswax, sunflower wax, rice bran wax, carnauba wax, or any combination thereof.

In some embodiments, the wax component includes a first wax and a second wax, in which a ratio of the first wax and the second wax is between 1:100 wt/wt to 100:1 wt/wt. In some embodiments, the wax component includes a naturally occurring wax from a single source or an extract thereof. In some embodiments, the composition contains at most 10 wt % or between 0.5 wt % and 8 wt % of the wax component.

In some embodiments, the broad spectrum UV absorber component can be selected from zinc oxide (ZnO), titanium dioxide ($TiO_2$), p-aminobenzoic acid, 3-(4-tert-butylphenyl)-1-(4-methoxyphenyl)propane-1,3-dione, 2-ethoxyethyl (2E)-3-(4-methoxyphenyl)prop-2-enoate, (2-hydroxy-4-methoxyphenyl)(2-hydroxyphenyl)methanone, 3,3,5-trimethylcyclohexyl 2-hydroxybenzoate, (1R,3R,4S)-p-menthan-3-yl 2-aminobenzoate, 2-ethylhexyl 2-cyano-3,3-diphenylprop-2-enoate, (RS)-2-ethylhexyl (2E)-3-(4-methoxyphenyl)prop-2-enoate, 2-ethylhexyl 2-hydroxybenzoate, 2-ethylhexyl 4-(dimethylamino)benzoate, 2-phenyl-3H-benzimidazole-5-sulfonic acid, 5-benzoyl-4-hydroxy-2-methoxybenzene-1-sulfonic acid, 2-hydroxy-N,N-bis(2-hydroxyethyl)ethan-1-aminium 2-hydroxybenzoate, and combinations thereof. In an embodiment, the broad spectrum UV absorber component is ZnO. In some embodiments, the broad spectrum UV absorber includes particles of a size between 500 and 9000 nanometers in diameter.

In some embodiments, the additive component includes vitamin E, sunflower lecithin, isopropyl myristate, isopropyl palmitate, vegetable glycerin, vegetable squalene, stearic acid, cetearyl alcohol, coco glucoside, starch, niacinamide, seaweed extract, iron oxide (FeO), silicate mineral, mica, or any combination thereof.

In some embodiments, the composition is characterized as having a % strain between 0.001-25%.

In some embodiments, the composition has a relative % UV absorption between 70% and 100%, a relative % visible light absorption between 3% and 7%, and/or a relative % near infrared light absorption between 10% and 14%, all inclusive of the end points.

In some embodiments, the composition has a melting temperature of between 25° C. and 90° C.

In some embodiments, the composition contains any of the following components:
a) about 4.30 wt % sunflower wax, about 76.75 wt % fractionated coconut oil, about 0.20 wt % vitamin E, and about 18.75 wt % ZnO; or
b) about 4.30 wt % sunflower wax, about 71.25 wt % fractionated coconut oil, about 0.20 wt % vitamin E, about 3.50 wt % babassu starch, about 2.00 wt % seaweed extract, and about 18.75 wt % ZnO; or
c) about 4.30 wt % sunflower wax, about 76.95 wt % fractionated coconut oil, and about 18.75 wt % ZnO; or
d) about 2.15 wt % beeswax, about 2.15 wt % candelilla, about 76.95 wt % fractionated coconut oil, and about 18.75 wt % ZnO; or
e) about 4.30 wt % sunflower wax, about 57.71 wt % fractionated coconut oil, about 19.24 wt % Abyssinian seed oil, and about 18.75 wt % ZnO; or
f) about 2.15 wt % beeswax, about 2.15 wt % candelilla, about 57.71 wt % fractionated coconut oil, about 19.24 wt % Abyssinian seed oil, and about 18.75 wt % ZnO; or
g) about 4.30 wt % sunflower wax, about 57.71 wt % fractionated coconut oil, about 19.24 wt % apricot oil, and about 18.75 wt % ZnO; or
h) about 2.15 wt % beeswax, about 2.15 wt % candelilla, about 57.71 wt % fractionated coconut oil, about 19.24 wt % apricot oil, and about 18.75 wt % ZnO; or
i) about 4.30 wt % sunflower wax, about 57.71 wt % fractionated coconut oil, about 19.24 wt % hemp, and about 18.75 wt % ZnO; or j) about 2.15 wt % beeswax, about 2.15 wt % candelilla, about 57.71 wt % fractionated coconut oil, about 19.24 wt % hemp, and about 18.75 wt % ZnO; or k) about 4.30 wt % sunflower wax, about 57.71 wt % fractionated coconut oil, about 19.24 wt % sesame oil, and about 18.75 wt % ZnO; or l) about 2.15 wt % beeswax, about 2.15 wt % candelilla, about 57.71 wt % fractionated coconut oil, about 19.24 wt % sesame oil, and about 18.75 wt % ZnO.

In some embodiments, the composition exhibits an SPF of between 10 and 50 (e.g., 10, 15, 20, 25, 30, 35, 40, 45, or 50).

In a second aspect, the disclosure features a method of making the composition of the first aspect by heating, mixing, and/or cooling a component or a combination of components.

In some embodiments, the method of the second aspect includes making a composition, including any of the steps of:
a) combining an oil component and a wax component with heating above a melting temperature of the oil and wax components to form a mixture, optionally with mixing;
b) adding a broad spectrum UV absorber component to the mixture, optionally with mixing;
c) cooling the mixture, optionally with mixing;
d) adding an additive component to the mixture, optionally with mixing;
e) optionally further cooling the mixture, optionally with mixing;
f) optionally holding the mixture at a temperature, optionally with mixing; and
g) optionally further cooling the mixture, optionally with mixing, thereby forming the composition.

In some embodiments, the oil component, wax component, and/or broad spectrum UV absorber component is added or dispersed before, during, and/or after the heating of aforementioned step a), and/or the additive component is added or dispersed after the heating of step a). In some embodiments, one or more of aforementioned steps a)-g) are performed under vacuum, wherein optionally the vacuum is between 0.2-0.6 bar below atmospheric pressure or about 0.2-0.6 bar (e.g., 0.3, 0.4, or 0.5 bar) below atmospheric pressure. In some embodiments, a component or a combination of components is heated, for example, in the aforementioned step a) to a temperature of between 25° C. and 95° C. In some embodiments, the holding step, for example, in the aforementioned step f), occurs at a temperature of between 25° C. and 85° C. In some embodiments, the cooling of aforementioned steps c), e), or g) is performed at a temperature of between 25° C. and 85° C. In some embodiments, a component or a combination of components is heated or cooled, for example, in the aforementioned steps a), c), e), or g), at a rate of between 0.1° C./min and 10° C./min. In some embodiments, the component or a combination of components is mixed during any of aforementioned steps a)-g) at a rate of between 0.05 $s^{-1}$ and 25 $s^{-1}$. In some embodiments, the component or a combination of components is held during any of aforementioned steps a)-g) at a specific temperature or mixed at a certain rate for a duration of time between 1 and 800 minutes.

In a third aspect, the disclosure features a method of making a sunscreen composition including any or all of the following steps:
a) combining an oil component and a wax component to form a mixture and heating the mixture above the melting temperature of the oil component or wax component, optionally while mixing;
b) adding a broad spectrum UV absorber component to the mixture of step a), optionally while mixing for a duration of time, and optionally under a vacuum;
c) cooling the mixture of step b), optionally while mixing, and optionally under a vacuum; and
d) adding an additive component to the mixture of step c), optionally while mixing for a duration of time, and optionally under a vacuum;

wherein the method optionally further includes one or more of:
e) further cooling the mixture of step d), optionally while mixing;
f) holding the mixture of step e) at a temperature for a duration of time, optionally while mixing; and
g) further cooling the mixture of step e) or f), optionally while mixing.

In some embodiments, the method of the third aspect includes any or all of the following details:
i) step a) includes heating the oil component and the wax component combined as the mixture to a temperature of between 50-95° C., optionally while mixing at a speed of between 0.05 $s^{-1}$ and 25 $s^{-1}$,
ii) step b) includes adding the broad spectrum UV absorber component to the mixture at a temperature of between 25-95° C., optionally while mixing at a speed of between 0.05 $s^{-1}$ and 25 $s^{-1}$ for a duration of time between 1-800 minutes, and/or optionally under a vacuum of between 0.2-0.6 bar below atmospheric pressure;
iii) step c) includes cooling the mixture to a temperature of between 25-85° C., optionally while mixing at a speed of between 0.05 $s^{-1}$ and 25 $s^{-1}$, and/or optionally under a vacuum of between 0.2-0.6 bar below atmospheric pressure;
iv) step d) includes adding the additive component to the mixture at a temperature of between 25-85° C., optionally while mixing at a speed of between 0.05 $s^{-1}$ and 25 $s^{-1}$ for a duration of between 1-800 minutes, and/or optionally under a vacuum of between 0.2-0.6 bar below atmospheric pressure;
vi) optional step e) includes cooling the mixture to a temperature of between 25-85° C., and/or optionally while mixing at a speed between 0.05 $s^{-1}$ and 25 $s^{-1}$.
v) optional step f) includes holding the mixture at a temperature of between 25-85° C. for a duration of time of between 1-800 min, and/or optionally while mixing at a speed between 0.05 $s^{-1}$ and 25 $s^{-1}$; and/or
vi) optional step g) includes further cooling the mixture to a temperature of between 25-85° C., optionally while mixing at a speed between 0.05 $s^{-1}$ and 25 $s^{-1}$.

In some embodiments, the method of the third aspect includes any or all of the following details:
the oil component of step a) includes between 50-90 wt % of the composition, and the wax component of step a) includes between 0.1-10 wt % of the composition;
the broad spectrum UV absorber component of step b) includes between 10-30 wt % of the composition;
the additive component of step d) includes between 0-20 wt % of the composition; and
the optional mixing of steps a)-g) includes one or more mixers comprising a central mixer, an anchor mixer, a rotor stator, or a combination thereof.

In some embodiments, the methods of the second or third aspects include any or all of the following details:

in step a), the oil component includes about 76.75 wt % fractionated coconut oil, the wax component includes about 4.3 wt % sunflower wax, the heating step includes heating the mixture to a temperature of about 75-85° C. (e.g., 80° C., 82° C., or 83° C.), and/or the optional mixing step includes mixing with a central mixer mixing at about 0.85-1.05 $s^{-1}$ (e.g., 0.93, 0.95, or 0.97 $s^{-1}$) and/or an anchor mixer mixing at about 0.80-1.00 $s^{-1}$ (e.g., 0.87, 0.90, or 0.93 $s^{-1}$), in step b), the broad spectrum UV absorber added to the mixture of step a) includes about 18.75 wt % zinc oxide, the optional mixing step includes mixing with a central mixer mixing at about 0.85-1.05 $s^{-1}$ (e.g., 0.93, 0.95, or 0.97 $s^{-1}$) or about 1.50-1.70 $s^{-1}$ (e.g., 1.52, 1.58, or 1.61 $s^{-1}$), an anchor mixer mixing at about 0.80-1.00 $s^{-1}$ (e.g., 0.87, 0.90, or 0.93 $s^{-1}$) or about 1.50-1.60 $s^{-1}$ (e.g., 1.50, 1.51, or 1.54 $s^{-1}$) and/or a rotor stator mixing at about 9.50-11.50 $s^{-1}$ (e.g., 9.85, 10.47, or 11.03 $s^{-1}$) or about 12.00-13.50 $s^{-1}$ (e.g., 12.57, 12.83, or 13.06 $s^{-1}$), the optional vacuum pressure is about 0.2-0.6 bar (e.g., 0.3, 0.4, or 0.5 bar) below atmospheric pressure, and/or the duration of time spent mixing is about 275-300 minutes (e.g., 284, 290, or 292 minutes);

in step c), the cooling step includes cooling the mixture to a temperature of about 69-75° C. (e.g., 69° C., 70° C., or 72° C.), the optional mixing step includes mixing with a central mixer mixing at about 0.85-1.05 $s^{-1}$ (e.g., 0.93, 0.95, or 0.97 $s^{-1}$), an anchor mixer mixing at about 0.80-1.00 $s^{-1}$ (e.g., 0.87, 0.90, or 0.93 $s^{-1}$) and a rotor stator mixing at about 12.00-13.50 $s^{-1}$ (e.g., 12.57, 12.83, or 13.06 $s^{-1}$), and/or the optional vacuum pressure is about 0.2-0.6 bar (e.g., 0.3, 0.4, or 0.5 bar) below atmospheric pressure;

in step d), the additive component includes Tocopherol (vitamin E, 0.2 wt %), the optional mixing step includes mixing with a central mixer mixing at about 0.85-1.05 $s^{-1}$ (e.g., 0.93, 0.95, or 0.97 $s^{-1}$) or about 1.50-1.70 $s^{-1}$ (e.g., 1.52, 1.58, or 1.61 $s^{-1}$), an anchor mixer mixing at about 0.80-1.00 $s^{-1}$ (e.g., 0.87, 0.90, or 0.93 $s^{-1}$) or about 1.50-1.60 $s^{-1}$ (e.g., 1.50, 1.51, or 1.54 $s^{-1}$) and a rotor stator mixing at about 9.50-11.50 $s^{-1}$ (e.g., 9.85, 10.47, or 11.03 $s^{-1}$) or about 12.00-13.50 $s^{-1}$ (e.g., 12.57, 12.83, or 13.06 $s^{-1}$), the optional vacuum pressure is about 0.2-0.6 bar (e.g., 0.3, 0.4, or 0.5 bar) below atmospheric pressure, and/or the duration of time spent mixing is about 500-600 minutes (e.g., 543, 554, or 570 minutes);

in step f), the holding step includes holding the mixture at a temperature of about 69-75° C. (e.g., 69° C., 70° C., or 72° C.), and/or mixing with a central mixer mixing at about 1.50-1.70 $s^{-1}$ (e.g., 1.52, 1.58, or 1.61 $s^{-1}$) and an anchor mixer mixing at about 1.50-1.60 $s^{-1}$ (e.g., 1.50, 1.51, or 1.54 $s^{-1}$) for about 720-800 minutes (e.g., 725, 750, or 800 minutes);

in step g), the cooling step includes cooling the mixture to a temperature of about 62-68° C. (e.g., 66° C., 67° C., or 68° C.), and/or mixing with a central mixer mixing at about 1.50-1.70 $s^{-1}$ (e.g., 1.52, 1.58, or 1.61 $s^{-1}$) and an anchor mixer mixing at about 1.50-1.60 $s^{-1}$ (e.g., 1.50, 1.51, or 1.54 $s^{-1}$), further cooling the mixture to about 51-61° C. (e.g., 54° C., 56° C., or 57° C.), and/or mixing with a central mixer mixing at about 0.85-1.05 $s^{-1}$ (e.g., 0.91, 0.92, or 0.96 $s^{-1}$) and an anchor mixer mixing at about 0.80-1.00 $s^{-1}$ (e.g., 0.87, 0.90, or 0.93 $s^{-1}$).

In some embodiments, the methods of the second or third aspects includes any or all of the following details:

in step a), the oil component includes about 71.25 wt % FCO, the wax component includes about 4.3 wt % SFW, the heating step includes heating the mixture to a temperature of about 75-85° C. (e.g., 80° C., 82° C., or 83° C.), and/or the optional mixing step includes mixing with a central mixer mixing at about 0.85-1.05 $s^{-1}$ (e.g., 0.93, 0.95, or 0.97 $s^{-1}$) and an anchor mixer mixing at about 0.80-1.00 $s^{-1}$ (e.g., 0.87, 0.90, or 0.93 $s^{-1}$);

in step b), the broad spectrum UV absorber includes about 18.75 wt % zinc oxide while mixing with a central mixer mixing at about 0.85-1.05 $s^{-1}$ (e.g., 0.93, 0.95, or 0.97 $s^{-1}$) or about 1.50-1.70 $s^{-1}$ (e.g., 1.52, 1.58, or 1.61 $s^{-1}$), an anchor mixer mixing at about 0.80-1.00 $s^{-1}$ (e.g., 0.87, 0.90, or 0.93 $s^{-1}$) or about 1.50-1.60 $s^{-1}$ (e.g., 1.50, 1.51, or 1.54 $s^{-1}$), and/or a rotor stator mixing at about 9.50-11.50 $s^{-1}$ (e.g., 9.85, 10.47, or 11.03 $s^{-1}$) or about 25.00-26.00 $s^{-1}$ (e.g., 25.31, 25.52, or 25.65 $s^{-1}$), the optional vacuum pressure is about 0.2-0.6 bar (e.g., 0.3, 0.4, or 0.5 bar) below atmospheric pressure, and/or the duration of time spent mixing is about 160-190 minutes (e.g., 165, 174, or 189 minutes);

in step c), the cooling step includes cooling the mixture to a temperature of about 69-75° C. (e.g., 69° C., 70° C., or 72° C.), the optional mixing step includes mixing with a central mixer mixing at about 0.85-1.05 $s^{-1}$ (e.g., 0.93, 0.95, or 0.97 $s^{-1}$), an anchor mixer mixing at about 0.80-1.00 $s^{-1}$ (e.g., 0.87, 0.90, or 0.93 $s^{-1}$) and a rotor stator mixing at about 12.00-13.50 $s^{-1}$ (e.g., 12.57, 12.83, or 13.06 $s^{-1}$), and/or the optional vacuum pressure is about 0.2-0.6 bar (e.g., 0.3, 0.4, or 0.5 bar) below atmospheric pressure;

in step d), the additive component includes Tocopherol (vitamin E, 0.2 wt %), seaweed extract (2.0 wt %) and babassu starch (3.5 wt %), the optional mixing step includes mixing with a central mixer mixing at about 0.85-1.05 $s^{-1}$ (e.g., 0.93, 0.95, or 0.97 $s^{-1}$) or about 1.50-1.70 $s^{-1}$ (e.g., 1.52, 1.58, or 1.61 $s^{-1}$), an anchor mixer mixing at about 0.80-1.00 $s^{-1}$ (e.g., 0.87, 0.90, or 0.93 $s^{-1}$) or about 1.50-1.60 $s^{-1}$ (e.g., 1.50, 1.51, or 1.54 $s^{-1}$), and a rotor stator mixing at about 12.00-13.50 $s^{-1}$ (e.g., 12.57, 12.83, or 13.06 $s^{-1}$), the optional vacuum pressure is about 0.2-0.6 bar (e.g., 0.3, 0.4, or 0.5 bar) below atmospheric pressure, and/or the duration of time spent mixing is about 300-360 minutes (e.g., 305, 332, or 345 minutes);

in step f), the holding step includes holding the mixture at a temperature of about 69-75° C. (e.g., 69° C., 70° C., or 72° C.), and/or mixing with a central mixer mixing at about 1.50-1.70 $s^{-1}$ (e.g., 1.52, 1.58, or 1.61 $s^{-1}$) and an anchor mixer mixing at about 1.50-1.60 $s^{-1}$ (e.g., 1.50, 1.51, or 1.54 $s^{-1}$) for about 720-800 minutes (e.g., 725, 750, or 800 minutes);

in step g), the cooling step includes cooling the mixture to a temperature of about 62-68° C. (e.g., 66° C., 67° C., or 68° C.), and/or mixing with a central mixer mixing at about 1.50-1.70 $s^{-1}$ (e.g., 1.52, 1.58, or 1.61 $s^{-1}$) and an anchor mixer mixing at about 1.50-1.60 $s^{-1}$ (e.g., 1.50, 1.51, or 1.54 $s^{-1}$), further cooling the mixture to about 51-61° C. (e.g., 54° C., 56° C., or 58° C.), and/or mixing with a central mixer mixing at about 0.85-1.05 $s^{-1}$ (e.g., 0.91, 0.92, or 0.96 $s^{-1}$) and an anchor mixer mixing at about 0.80-1.00 $s^{-1}$ (e.g., 0.87, 0.90, or 0.93 $s^{-1}$).

In a fourth aspect, the disclosure features a method of reducing the risk of sun damage to the skin by applying the composition of the first aspect to the skin. The composition can be reapplied one or more times, as needed to maintain sun protection. For example, the composition can be reapplied once every 1, 2, 3, 4, 5, 6, 7, 8, 9, or 10 hours or at a time between 1-10 hours.

Definitions

As used herein, "a" or "an" means "at least one" or "one or more" unless otherwise indicated. In addition, the singular forms "a", "an", and "the" include plural referents unless the context clearly dictates otherwise.

As used herein, the term "about" means +/−10% of the recited value.

As used herein, the term "organogel" means a semi-solid system with an organic liquid phase immobilized by a three-dimensional network composed of self-assembled, crosslinked or entangled gelators in a specific morphology, e.g., fibers, plates, needles, spherulites or other form.

As used herein, the term "oleogel" means an organic liquid entrapped within a thermally reversible, three-dimensional gel network.

As used herein, the term "oil" means a viscous liquid derived from a plant or other natural source, especially for use as a lubricant or emollient. Oils from other sources can also be used to produce a composition of the disclosure.

As used herein, the term "wax" means a lipophilic or amphiphilic, malleable, organic compound that is solid near ambient temperature. A wax can include higher alkanes, esters and lipids with melting points above ambient temperature that are insoluble or substantially insoluble in water but soluble in nonpolar organic solvents or amphiphilic. A wax may also be synthetically produced.

As used herein, the term "stiffness" means the extent to which a composition resist deformation in response to an applied force.

As used herein, the term "hardness" means the resistance of a composition to localized deformation, such as indentation or scratching.

As used herein, the term "spreadability" means the extent to which a composition can be extended or distributed over a larger space or surface.

As used herein, the term "dryness" refers to the feeling that an oil leaves after applying it on the skin. The higher the dryness the least residue is left and therefore a lower oily after feel (see, e.g., ASTM International. 2009. Standard Terminology Relating to Sensory Evaluations of Materials and Products, E253-09a. ASTM International, West Conshohocken, PA. E253-09a; incorporated herein by reference).

As used herein, the term "absorption time" means the time required for a composition applied to skin to travel from the site of application to a site of action, e.g., the time needed for a composition to transfer from a supradermal location to an epidermal location.

As used herein, the term "% strain" means the amount of deformation made to the shape of the product as force is applied before the sample structure is ruptured, an oscillatory force that is applied in a parallel orientation to the surface of the fluid.

As used herein, the term "antioxidant" means a substance that inhibits oxidation, especially one used to counter act the deterioration of a composition.

As used herein, the term "application" or "topical application" or "apply" means the act of applying a composition or substance to a surface, e.g., the skin.

As used herein, the term "broad spectrum UV absorber" means a material that absorbs UV radiation from both the UVA (320-400 nm) and UVB (280-320 nm) ranges within the UV light range of the electromagnetic spectrum.

As used herein, the term "sun damage" or "skin damage" means the damage that exposure to the sun does to skin, which can cause premature aging or cancer.

As used herein, the term "critical gelation concentration" or "CGC" means the minimum concentration of a gelator needed to form a consistent gel.

As used herein, the term "gelator" means any substance capable of forming a gel.

As used herein, the term "syneresis" means the release of liquid from the gel network observed as the separating out of liquid from a composition.

As used herein, the term "thixotropy" means the property of structural recovery of a gel after being subjected to an applied stress. For example, a gel may become temporarily fluid when shaken or mixed followed by a re-structure of the gel network in static conditions.

As used herein, the term "unsaturated" or "unsaturated bonds" means having carbon-carbon double or triple bonds and therefore not containing the greatest possible number of hydrogen atoms for the number of carbons.

As used herein, the term "water activity" or "Aw" means the partial vapor pressure of water in a composition divided by the standard state partial vapor pressure of water.

BRIEF DESCRIPTION OF THE DRAWINGS

FIG. 1 is a table showing the fatty acid composition (in wt %) including caprylic, capric, lauric, myristic, palmitic, stearic, oleic, linoleic, linolenic, punicic, gondoic, or erucic acid, of various raw oils, including coconut oil (CO), fractionated coconut oil (FCO), medium chain triglycerides (MCT oil), babassu oil, baobab oil (BAO), sunflower oil (SFO), canola oil (CAO), apricot oil (APO), rice oil (RO), sesame oil (SEO), grapeseed oil (GSO), linseed oil (LSO), hemp oil (HEO or HEMP), pomegranate oil, jojoba oil (JJO), and Abyssinian seed oil (ABO), selected for screening. The "No C" column lists the number of carbon atoms in the fatty acid chain, and the "Unsat" column lists the number of carbon-carbon bonds within the fatty acid chain that are double or triple bonds, otherwise known as unsaturated bonds.

FIG. 7 is a table showing the raw waxes, including candelilla wax (CLW), beeswax (BW), sunflower wax (SFW), rice bran wax (RW), carnauba wax (CUW), selected for screening broken down into their ester, hydrocarbon, free fatty acid, and alcohol components by wt %.

FIG. 8 is a table showing the critical gelation concentrations (CGC) for the combinations of one of CUW, RW, CW, or BW, and SFW with one of SFO, GSO, FCO, or RO.

FIG. 10 is a table showing the results of the thixotropy test performed on scooped and sheared samples of each gel composition made from one wax and one oil. The light grey shading indicates an undesirable result, whereas the dark grey shading indicates a desirable result.

FIG. 12 is a table showing the fluid properties of compositions formed using a wax component comprising 1:1 ratios of one of CUW, RW, SFW, BW, or CW with one of BW or CW, and an oil component comprising either SFO or FCO. Only 1:1 BW:CW wax forms a gel with SFO or FCO.

FIG. 13 is a table showing the fluid properties of compositions formed using a wax component comprising one of 1 wt % SFW, 0.5 wt % BW+0.5 wt % CW, 1.0 wt % BW+0.5 wt % CW, 1.0 wt % BW+1 wt % CW, or 0.5 wt % SFW+0.5 wt % BW, with an oil component comprising one of HEMP, SEO, APO, FCO, or ABO. While 1 wt % SFW formed a gel with any of the five oils, 0.5 wt % BW+0.5 wt % CW only formed gels with APO, FCO, and ABO, 1.0 wt % BW+0.5 wt % CW only formed gels with HEMP, FCO, and ABO, 1.0 wt % BW+1 wt % CW only formed gels with SEO, FCO, and ABO, and 0.5 wt % SFW+0.5 wt % BW did not form gels with any oils.

FIG. 23 is a table showing the summarized results from the sensorial tests. Composition F1 was determined to provide the most satisfactory user experience with a sensorial result of 20 and F9 had the second most satisfactory user experience with a sensorial result of 17. Formulations F2, F5, and F6 had the least satisfactory user experience with a sensorial result of 0, and formulations F4 and F6 displayed undesirable syneresis.

FIG. 24 is a table showing modifications to the process on base formulation F1 to find a softer and more pleasant skin feel.

FIG. 33 is a table showing the thermal parameters of crystallization and melting such as start and end peak locations and enthalpies from the high resolution DSC curves of SFW and NSFW.

DETAILED DESCRIPTION

Figure 2:
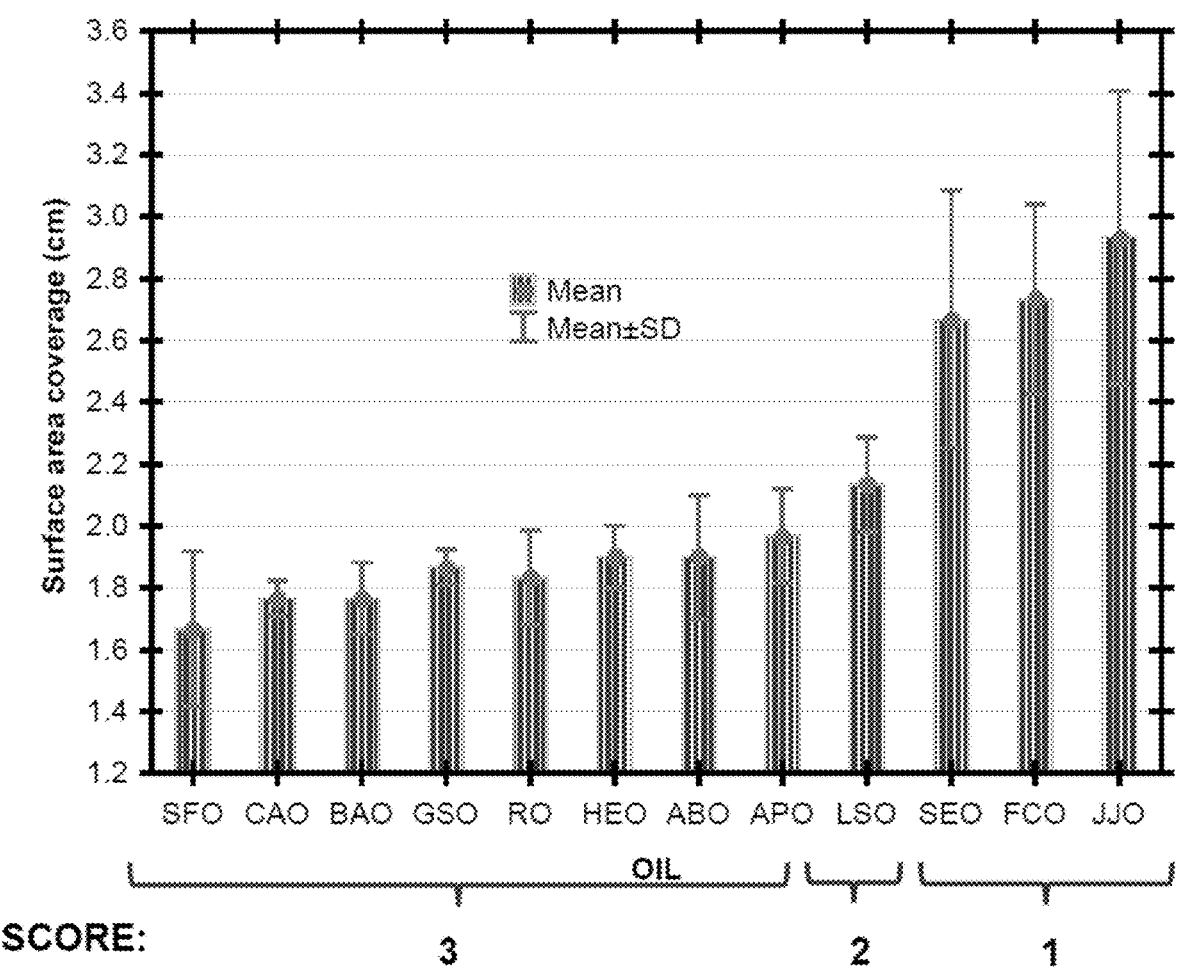
FIG. 2 is a plot showing the surface area coverage diameters in centimeters of each oil and their corresponding numerical score.

The disclosure features compositions (e.g., sunscreen compositions), methods of producing the compositions, and methods of using the compositions (e.g., to reduce the risk of sun damage to the skin). The compositions can be shelf-stable organogels that do not separate into their constituent oils, waxes, broad spectrum UV absorbers, or additives for two-three years or more and that is capable of being smeared without compromising original structure (oleogel) or its original viscosity with no other chemical emulsifiers, preservatives, or stabilizers. The compositions also contain a low weight percent loading of wax relative to other commercially available sunscreens (e.g., 10 wt % or less). The compositions may be oil-based compositions that do not contain any added water (e.g., anhydrous, with a water activity (Aw) less than 0.7, or with less than 0.1 wt % water or that contain water naturally associated with a wax or oil component and in an amount of less than 20 wt % (e.g., 0.5 wt % or less). The compositions may contain a wax component that is at most 10 wt % of the composition. The compositions are able to reduce the risk of sun damage (e.g., they have an SPF of 10 to 50 (e.g., 10, 15, 20, 25, 30, 35, 40, 45, or 50), and, thus, can be used as a topical sunscreen.

Compositions of the Disclosure

The compositions described herein may include an oil component, a wax component, broad spectrum UV absorber component, and an additive component. In some embodiments, the oil, wax, and additive components may include one or more ingredients, e.g., the oil component includes one or more oils, the wax component includes one or more waxes, and the additive component includes one or more additives. Certain combinations of these constituents produce compositions with desirable physicochemical properties including, e.g., a lack of constituent separation, or lack of syneresis, and/or a viscosity that changes upon application of stress but fully or partially recovers after the applied stress is removed (shows a degree of thixotropy) formulations with low syneresis and some degree of thixotropy contain an oil component of between 50-90 wt % (w/w), a wax component of between 0.1-10 wt % (w/w), a broad spectrum UV absorber component of between 10-30 wt % (w/w), an additive component of between 0-20 wt % (w/w), and a water component of between 0-20 wt % (w/w). In a particular example, a sunscreen formulation exhibiting low syneresis and neutral thixotropy may be a composition containing about 4.30 wt % SFW, about 76.75 wt % FCO, about 0.20 wt % vitamin E, and about 18.75 wt % ZnO. In a particular example, the sunscreen formulation does not contain an appreciable amount of water (e.g., Aw<0.7, less than 0.1 wt % water, or anhydrous). In a particular example, the sunscreen formulation contains a wax component that is at most 10 wt % of the composition.

Oil Component

A composition of the disclosure may include between 50-90 wt % (w/w) of the oil component, e.g., about 50, 55, 60, 65, 70, 75, 80, 85, or 90 wt %, greater than 50 wt %, greater than 55 wt %, greater than 60 wt %, greater than 65 wt %, greater than 70 wt %, greater than 75 wt %, greater than 80 wt %, greater than 85 wt %, less than 90 wt %, less than 85 wt %, less than 80 wt %, less than 75 wt %, less than 70 wt %, less than 65 wt %, less than 60 wt %, or less than 55 wt %, 50-55 wt %, 55-60 wt %, 60-65 wt %, 65-70 wt %, 70-75 wt %, 75-80 wt %, 80-85 wt %, 85-90 wt %, 50-60 wt %, 55-65 wt %, 60-70 wt %, 65-75 wt %, 70-80 wt %, 75-85 wt %, 80-90 wt %, 50-65 wt %, 55-70 wt %, 60-75 wt %, 65-80 wt %, 70-85 wt %, 75-90 wt %, 50-70 wt %, 55-75 wt %, 60-80 wt %, 65-85 wt %, 70-90 wt %, 50-75 wt %, 55-80 wt %, 60-85 wt %, 65-90 wt %, 50-80 wt %, 55-85 wt %, 60-90 wt %, 50-85 wt %, or 55-90 wt % of the oil component. In a particular embodiment, the composition includes 50-90 wt % of the oil component. For example, the composition includes about 76.75 wt % of the oil component.

In some embodiments, the oil component may include coconut oil (CO), fractionated coconut oil (FCO), medium chain triglycerides (MCT oil), babassu oil, baobab oil (BAO), sunflower oil (SFO), canola oil (CAO), apricot oil (APO), rice oil (RO), sesame oil (SEO), grapeseed oil (GSO), linseed oil (LSO), hemp oil (HEO or HEMP), pomegranate oil, jojoba oil (JJO), Abyssinian seed oil (ABO), a mixture of alkanes of vegetable origin, or any combination thereof. In preferred embodiment, the oil component includes FCO.

In some embodiments, the oil component may include a first oil and a second oil, in which a ratio of the first oil and the second oil is between 1:100 wt/wt to 100:1 wt/wt, e.g., about 1:100, 1:75, 1:50, 1:20, 1:10, 1:5, 1:2, 1:1, 2:1, 5:1, 10:1, 20:1, 50:1, 75:1, 100:1 wt/wt, or between 1:100-1:75, 1:75-1:50, 1:50-1:20, 1:20-1:10, 1:10-1:5, 1:5-1:2, 1:2-1:1, 1:1-2:1, 2:1-5:1, 5:1-10:1, 10:1-20:1, 20:1-50:1, 50:1-75:1, or 75:1-100:1. In a preferred embodiment, the oil component includes a single oil.

Wax Component

A composition of the disclosure may include between 0.1-10 wt % of the wax component, e.g., about 0.1, 0.2, 0.5, 1, 2, 5, or 10 wt %, greater than 0.1 wt %, greater than 0.2 wt %, greater than 0.5 wt %, greater than 1 wt %, greater than 2 wt %, greater than 5 wt %, less than 10 wt %, less than 5 wt %, less than 2 wt %, less than 1 wt %, less than 0.5 wt %, less than 0.2 wt %, 0.1-0.2 wt %, 0.2-0.5 wt %, 0.5-1 wt %, 1-2 wt %, 2-5 wt %, 5-10 wt %, 0.1-0.5 wt %, 0.2-1 wt %, 0.5-2 wt %, 1-5 wt %, 2-10 wt %, 0.1-1 wt %, 0.2-2 wt %, 0.5-5 wt %, or 1-10 wt % of the wax component. In a particular embodiment, the composition includes 0.1-10 wt % of the wax component. For example, the composition includes about 4.30 wt % of the wax component. In a preferred embodiment, the sunscreen formulation contains a wax component that is at most 10 wt % of the composition.

In some embodiments, the waxes that include the wax component include candelilla wax (CLW), beeswax (BW), sunflower wax (SFW), rice bran wax (RW), carnauba wax (CUW), or any combination thereof. In some embodiments, the wax component may include one or more naturally occurring waxes from a single source and/or any of the extracts obtained from the original source. For example, the wax component may include SFW.

In some embodiments, the wax component may include a first wax and a second wax, in which a ratio of the first wax and the second wax is between 1:100 wt/wt to 100:1 wt/wt, e.g., about 1:100, 1:75, 1:50, 1:20, 1:10, 1:5, 1:2, 1:1, 2:1, 5:1, 10:1, 20:1, 50:1, 75:1, 100:1 wt/wt, or between 1:100-1:75, 1:75-1:50, 1:50-1:20, 1:20-1:10, 1:10-1:5, 1:5-1:2, 1:2-1:1, 1:1-2:1, 2:1-5:1, 5:1-10:1, 10:1-20:1, 20:1-50:1, 50:1-75:1, or 75:1-100:1. For example, the wax component may include a single wax. In another example, the wax component may include two waxes.

Broad Spectrum UV Absorber Component

A composition of the disclosure may include 10-30 wt % of a broad spectrum UV absorber, e.g., about 10, 12, 15, 20, 22, 25, or 30 wt %, greater than 10 wt %, greater than 12 wt %, greater than 15 wt %, greater than 20 wt %, greater than 22 wt %, greater than 25 wt %, less than 30 wt %, less than 25 wt %, less than 22 wt %, less than 20 wt %, less than 15 wt %, less than 12 wt %, 10-12 wt %, 12-15 wt %, 15-20 wt %, 20-22 wt %, 22-25 wt %, 25-30 wt %, 10-15 wt %, 12-20 wt %, 15-22 wt %, 20-25 wt %, 22-30 wt %, 10-20 wt %, 12-22 wt %, 15-25 wt %, 20-30 wt %, 10-22 wt %, 12-25 wt %, 15-30 wt %, 10-25 wt %, or 12-30 wt %. In particular embodiments, the composition includes 10-30 wt % of a broad spectrum UV absorber. For example, the composition may include about 18.75 wt % of a broad spectrum UV absorber (e.g., ZnO).

In some embodiments, the broad spectrum UV absorber may be selected from the group consisting of zinc oxide (ZnO), titanium dioxide ($TiO_2$), p-aminobenzoic acid, 3-(4-tert-butylphenyl)-1-(4-methoxyphenyl)propane-1,3-dione, 2-ethoxyethyl (2E)-3-(4-methoxyphenyl)prop-2-enoate, (2-hydroxy-4-methoxyphenyl)(2-hydroxyphenyl)methanone, 3,3,5-trimethylcyclohexyl 2-hydroxybenzoate, (1R,3R,4S)-p-menthan-3-yl 2-aminobenzoate, 2-ethylhexyl 2-cyano-3,3-diphenylprop-2-enoate, (RS)-2-ethylhexyl (2E)-3-(4-methoxyphenyl)prop-2-enoate, 2-ethylhexyl 2-hydroxybenzoate, 2-ethylhexyl 4-(dimethylamino)benzoate, 2-phenyl-3H-benzimidazole-5-sulfonic acid, 5-benzoyl-4-hydroxy-2-methoxybenzene-1-sulfonic acid, 2-hydroxy-N,N-bis(2-hydroxyethyl)ethan-1-aminium 2-hydroxybenzoate, and combinations thereof. For example, the broad spectrum UV absorber may be ZnO or titanium dioxide.

In some embodiments, the broad spectrum UV absorber may be in the form of particles (e.g., microparticles or nanoparticles). In some embodiments, the broad spectrum UV absorber may include particles of a size between 500 and 9000 nanometers in diameter, e.g., about 500, 1000, 1500, 2000, 2500, 3000, 3500, 4000, 4500, 5000, 5500, 6000, 6500, 7000, 7500, 8000, 8500, or 9000 nm, greater than 500 nm, greater than 1000 nm, greater than 1500 nm, greater than 2000 nm, greater than 2500 nm, greater than 3000 nm, greater than 3500 nm, greater than 4000 nm, greater than 4500 nm, greater than 5000 nm, greater than 5500 nm, greater than 6000 nm, greater than 6500 nm, greater than 7000 nm, greater than 7500 nm, greater than 8000 nm, greater than 8500 nm, less than 9000 nm, less than 8500 nm, less than 8000 nm, less than 7500 nm, less than 7000 nm, less than 6500 nm, less than 6000 nm, less than 5500 nm, less than 5000 nm, less than 4500 nm, less than 4000 nm, less than 3500 nm, less than 3000 nm, less than 2500 nm, less than 2000 nm, less than 1500 nm, less than 1000 nm, between 500-1000 nm, 1000-1500 nm, 1500-2000 nm, 2000-2500 nm, 2500-3000 nm, 3000-3500 nm, 3500-4000 nm, 4000-4500 nm, 4500-5000 nm, 5000-5500 nm, 5500-6000 nm, 6000-6500 nm, 6500-7000 nm, 7000-7500 nm, 7500-8000 nm, 8000-8500 nm, 8500-9000 nm, 500-1500 nm, 1000-2000 nm, 1500-2500 nm, 2000-3000 nm, 2500-3500 nm, 3000-4000 nm, 3500-4500 nm, 4000-5000 nm, 4500-5500 nm, 5000-6000 nm, 5500-6500 nm, 6000-7000 nm, 6500-7500 nm, 7000-8000 nm, 7500-8500 nm, 8000-9000 nm, 500-2000 nm, 1000-2500 nm, 1500-3000 nm, 2000-3500 nm, 2500-4000 nm, 3000-4500 nm, 3500-5000 nm, 4000-5500 nm, 4500-6000 nm, 5000-6500 nm, 5500-7000 nm, 6000-7500 nm, 6500-8000 nm, 7000-8500 nm, 7500-9000 nm, 500-2500 nm, 1000-3000 nm, 1500-3500 nm, 2000-4000 nm, 2500-4500 nm, 3000-5000 nm, 3500-5500 nm, 4000-6000 nm, 4500-6500 nm, 5000-7000 nm, 5500-7500 nm, 6000-8000 nm, 6500-8500 nm, 7000-9000 nm, 500-3000 nm, 1000-3500 nm, 1500-4000 nm, 2000-4500 nm, 2500-5000 nm, 3000-5500 nm, 3500-6000 nm, 4000-6500 nm, 4500-7000 nm, 5000-7500 nm, 5500-8000 nm, 6000-8500 nm, 6500-9000 nm, 500-3500 nm, 1000-4000 nm, 1500-4500 nm, 2000-5000 nm, 2500-5500 nm, 3000-6000 nm, 3500-6500 nm, 4000-7000 nm, 4500-7500 nm, 5000-8000 nm, 5500-8500 nm, 6000-9000 nm, 500-4000 nm, 1000-4500 nm, 1500-5000 nm, 2000-5500 nm, 2500-6000 nm, 3000-6500 nm, 3500-7000 nm, 4000-7500 nm, 4500-8000 nm, 5000-8500 nm, 5500-9000 nm, 500-4500 nm, 1000-5000 nm, 1500-5500 nm, 2000-6000 nm, 2500-6500 nm, 3000-7000 nm, 3500-7500 nm, 4000-8000 nm, 4500-8500 nm, 5000-9000 nm, 500-5000 nm, 1000-5500 nm, 1500-6000 nm, 2000-6500 nm, 2500-7000 nm, 3000-7500 nm, 3500-8000 nm, 4000-8500 nm, 4500-9000 nm, 500-5500 nm, 1000-6000 nm, 1500-6500 nm, 2000-7000 nm, 2500-7500 nm, 3000-8000 nm, 3500-8500 nm, 4000-9000 nm, 500-6500 nm, 1000-7000 nm, 1500-7500 nm, 2000-8000 nm, 2500-8500 nm, 3000-9000 nm, 500-7000 nm, 1000-7500 nm, 1500-8000 nm, 2000-8500 nm, 2500-9000 nm, 500-7500 nm, 1000-8000 nm, 1500-8500 nm, 1000-9000 nm, 500-8000 nm, 1000-8500 nm, 1500-9000 nm, 500-8500 nm, or 1000-9000 nm.

Additive Component

A composition of the disclosure may include between 0-20 wt % of the additive component, e.g., about 0, 0.1, 0.2, 0.5, 1, 2, 5, 10, or 20 wt %, greater than 0 wt %, greater than 0.1 wt %, greater than 0.2 wt %, greater than 0.5 wt %, greater than 1 wt %, greater than 2 wt %, greater than 5 wt %, greater than 10 wt %, less than 20 wt %, less than 10 wt %, less than 5 wt %, less than 2 wt %, less than 1 wt %, less than 0.5 wt %, less than 0.2 wt %, less than 0.1 wt %, 0-0.1 wt %, 0.1-0.2 wt %, 0.2-0.5 wt %, 0.5-1 wt %, 1-2 wt %, 2-5 wt %, 5-10 wt %, 10-20 wt %, 0-0.2 wt %, 0.1-0.5 wt %, 0.2-1 wt %, 0.5-2 wt %, 1-5 wt %, 2-10 wt %, 5-20 wt %, 0-0.5 wt %, 0.1-1 wt %, 0.2-2 wt %, 0.5-5 wt %, 1-10 wt %, or 2-20 wt % of the additive component. In particular embodiments, the composition includes 0-20 wt % of the additive component. For example, the composition may include about 0.20 wt % of the additive component.

In some embodiments, the additive of the additive component may be vitamin E, sunflower lecithin, isopropyl myristate, isopropyl palmitate, vegetable glycerin, vegetable squalene, stearic acid, cetearyl alcohol, coco glucoside, starch, niacinamide, seaweed extract, babassu starch, iron oxide (FeO), a silicate mineral, e.g., mica, or any combination thereof. For example, the additive component may be or may include vitamin E. In another example, the additive component may include vitamin E, babassu starch, and seaweed extract. In another example, the additive component may include a single component. In another example, the additive component may include two components.

Other Components

A composition of the disclosure may include between 0 wt % and 20 wt % water, e.g., about 0, 0.1, 0.2, 0.5, 1, 2, 5, 10, or 20 wt %, greater than 0 wt %, greater than 0.1 wt %, greater than 0.2 wt %, greater than 0.5 wt %, greater than 1 wt %, greater than 2 wt %, greater than 5 wt %, greater than 10 wt %, less than 20 wt %, less than 10 wt %, less than 5 wt %, less than 2 wt %, less than 1 wt %, less than 0.5 wt %, less than 0.2 wt %, less than 0.1 wt %, 0-0.1 wt %, 0.1-0.2 wt %, 0.2-0.5 wt %, 0.5-1 wt %, 1-2 wt %, 2-5 wt %, 5-10 wt %, 10-20 wt %, 0-0.2 wt %, 0.1-0.5 wt %, 0.2-1 wt %, 0.5-2 wt %, 1-5 wt %, 2-10 wt %, 5-20 wt %, 0-0.5 wt %, 0.1-1 wt %, 0.2-2 wt %, 0.5-5 wt %, 1-10 wt %, or 2-20 wt % water. In particular embodiments, the composition includes 0-20 wt % of water. For example, the composition may not include water (e.g., includes about 0 wt % water, is anhydrous, or has an Aw<0.7). Water, if present in the composition, may be water that naturally accompanies one of the other components (e.g., the wax or oil component) and may be present in an amount of 20 wt % or less (e.g., 0.5 wt % or less).

In some embodiments, the composition includes only the oil component, the wax component, the broad spectrum UV absorber (e.g., ZnO), and vitamin E. In some embodiments, the composition includes only oil, wax, a broad spectrum UV absorber (e.g., ZnO), vitamin E, babassu starch, and seaweed extract. In some embodiments, the composition may not include an emulsifier, preservative, or stabilizer. In some embodiments, the composition essentially lacks any water (e.g., the composition is anhydrous).

Compositions

Compositions of the disclosure may include an oil component in an amount of between 50-90 wt % (w/w), e.g., about 50, 55, 60, 65, 70, 75, 80, 85, or 90 wt %, greater than 50 wt %, greater than 55 wt %, greater than 60 wt %, greater than 65 wt %, greater than 70 wt %, greater than 75 wt %, greater than 80 wt %, greater than 85 wt %, less than 90 wt %, less than 85 wt %, less than 80 wt %, less than 75 wt %, less than 70 wt %, less than 65 wt %, less than 60 wt %, or less than 55 wt %, 50-55 wt %, 55-60 wt %, 60-65 wt %, 65-70 wt %, 70-75 wt %, 75-80 wt %, 80-85 wt %, 85-90 wt %, 50-60 wt %, 55-65 wt %, 60-70 wt %, 65-75 wt %, 70-80 wt %, 75-85 wt %, 80-90 wt %, 50-65 wt %, 55-70 wt %, 60-75 wt %, 65-80 wt %, 70-85 wt %, 75-90 wt %, 50-70 wt %, 55-75 wt %, 60-80 wt %, 65-85 wt %, 70-90 wt %, 50-75 wt %, 55-80 wt %, 60-85 wt %, 65-90 wt %, 50-80 wt %, 55-85 wt %, 60-90 wt %, 50-85 wt %, or 55-90 wt %, a wax component in an amount of between 0.1-10 wt % (w/w), e.g., about 0.1, 0.2, 0.5, 1, 2, 5, or 10 wt %, greater than 0.1 wt %, greater than 0.2 wt %, greater than 0.5 wt %, greater than 1 wt %, greater than 2 wt %, greater than 5 wt %, less than 10 wt %, less than 5 wt %, less than 2 wt %, less than 1 wt %, less than 0.5 wt %, less than 0.2 wt %, 0.1-0.2 wt %, 0.2-0.5 wt %, 0.5-1 wt %, 1-2 wt %, 2-5 wt %, 5-10 wt %, 0.1-0.5 wt %, 0.2-1 wt %, 0.5-2 wt %, 1-5 wt %, 2-10 wt %, 0.1-1 wt %, 0.2-2 wt %, 0.5-5 wt %, or 1-10 wt %, a broad spectrum UV absorber component (e.g., ZnO) in an amount of between 10-30 wt % (w/w), e.g., about 10, 12, 15, 20, 22, 25, or 30 wt %, greater than 10 wt %, greater than 12 wt %, greater than 15 wt %, greater than 20 wt %, greater than 22 wt %, greater than 25 wt %, less than 30 wt %, less than 25 wt %, less than 22 wt %, less than 20 wt %, less than 15 wt %, less than 12 wt %, 10-12 wt %, 12-15 wt %, 15-20 wt %, 20-22 wt %, 22-25 wt %, 25-30 wt %, 10-15 wt %, 12-20 wt %, 15-22 wt %, 20-25 wt %, 22-30 wt %, 10-20 wt %, 12-22 wt %, 15-25 wt %, 20-30 wt %, 10-22 wt %, 12-25 wt %, 15-30 wt %, 10-25 wt %, or 12-30 wt %, an additive component (e.g., vitamin E) in an amount of between 0-20 wt % (w/w), e.g., about 0, 0.1, 0.2, 0.5, 1, 2, 5, 10, or 20 wt %, greater than 0 wt %, greater than 0.1 wt %, greater than 0.2 wt %, greater than 0.5 wt %, greater than 1 wt %, greater than 2 wt %, greater than 5 wt %, greater than 10 wt %, less than 20 wt %, less than 10 wt %, less than 5 wt %, less than 2 wt %, less than 1 wt %, less than 0.5 wt %, less than 0.2 wt %, less than 0.1 wt %, 0-0.1 wt %, 0.1-0.2 wt %, 0.2-0.5 wt %, 0.5-1 wt %, 1-2 wt %, 2-5 wt %, 5-10 wt %, 10-20 wt %, 0-0.2 wt %, 0.1-0.5 wt %, 0.2-1 wt %, 0.5-2 wt %, 1-5 wt %, 2-10 wt %, 5-20 wt %, 0-0.5 wt %, 0.1-1 wt %, 0.2-2 wt %, 0.5-5 wt %, 1-10 wt %, or 2-20 wt %, and, optionally, an aqueous component (e.g., water) in an amount of between 0-20 wt % (w/w), e.g., about 0, 0.1, 0.2, 0.5, 1, 2, 5, 10, or 20 wt %, greater than 0 wt %, greater than 0.1 wt %, greater than 0.2 wt %, greater than 0.5 wt %, greater than 1 wt %, greater than 2 wt %, greater than 5 wt %, greater than 10 wt %, less than 20 wt %, less than 10 wt %, less than 5 wt %, less than 2 wt %, less than 1 wt %, less than 0.5 wt %, less than 0.2 wt %, less than 0.1 wt %, 0-0.1 wt %, 0.1-0.2 wt %, 0.2-0.5 wt %, 0.5-1 wt %, 1-2 wt %, 2-5 wt %, 5-10 wt %, 10-20 wt %, 0-0.2 wt %, 0.1-0.5 wt %, 0.2-1 wt %, 0.5-2 wt %, 1-5 wt %, 2-10 wt %, 5-20 wt %, 0-0.5 wt %, 0.1-1 wt %, 0.2-2 wt %, 0.5-5 wt %, 1-10 wt %, or 2-20 wt %.

In some embodiments, the composition is characterized as having or may exhibit a % strain between 0.001-25%, e.g., about 0.001, 0.002, 0.005, 0.01, 0.02, 0.05, 0.1, 0.2, 0.5, 1, 2, 5, 10, 15, 20, or 25%, greater than 0.001%, greater than 0.002%, greater than 0.005%, greater than 0.01%, greater than 0.02%, greater than 0.05%, greater than 0.1%, greater than 0.2%, greater than 0.5%, greater than 1%, greater than 2%, greater than 5%, greater than 10%, greater than 15%, greater than 20%, less than 0.002%, less than 0.005%, less than 0.01%, less than 0.02%, less than 0.05%, less than 0.1%, less than 0.2%, less than 0.5%, less than 1%, less than 2%, less than 5%, less than 10%, less than 15%, less than 20%, less than 25%, 0.001-0.002%, 0.002-0.005%, 0.005-0.01%, 0.01-0.02%, 0.02-0.05%, 0.05-0.1%, 0.1%-0.2%, 0.2-0.5%, 0.5-1%, 1-2%, 2-5%, 5-10%, 10-15%, 15-20%, 20-25%, 0.001-0.005%, 0.002-0.01%, 0.005-0.02%, 0.01-0.05%, 0.02-0.1%, 0.05-0.2%, 0.1%-0.5%, 0.2-1%, 0.5-2%, 1-5%, 2-10%, 5-15%, 10-20%, 15-25%, 0.001-0.01%, 0.002-0.02%, 0.005-0.05%, 0.01-0.1%, 0.02-0.2%, 0.05-0.5%, 0.1%-1%, 0.2-2%, 0.5-5%, 1-10%, 2-15%, 5-20%, 10-25%, 0.001-0.02%, 0.002-0.05%, 0.005-0.1%, 0.01-0.2%, 0.02-0.5%, 0.05-1%, 0.1%-2%, 0.2-5%, 0.5-10%, 1-15%, 2-20%, 5-25%, 0.001-0.05%, 0.002-0.1%, 0.005-0.2%, 0.01-0.5%, 0.02-1%, 0.05-2%, 0.1%-5%, 0.2-10%, 0.5-15%, 1-20%, 2-25%, 0.001-0.1%, 0.002-0.2%, 0.005-0.5%, 0.01-1%, 0.02-2%, 0.05-5%, 0.1%-10%, 0.2-15%, 0.5-20%, 1-25%, 0.001-0.2%, 0.002-0.5%, 0.005-1%, 0.01-2%, 0.02-5%, 0.05-10%, 0.1%-15%, 0.2-20%, 0.5-25%, 0.001-0.5%, 0.002-1%, 0.005-2%, 0.01-5%, 0.02-10%, 0.05-15%, 0.1%-20%, 0.2-25%, 0.001-1%, 0.002-2%, 0.005-5%, 0.01-10%, 0.02-15%, 0.05-20%, 0.1%-25%, 0.001-2%, 0.002-5%, 0.005-10%, 0.01-15%, 0.02-20%, 0.05-25%, 0.001-5%, 0.002-10%, 0.005-15%, 0.01-20%, 0.02-25%, 0.001-10%, 0.002-15%, 0.005-20%, 0.01-25%, 0.001-15%, 0.002-20%, 0.005-25%, 0.001-20%, or 0.002-25%.

In some embodiments, the composition may exhibit a low degree of hardness ($\eta^* < 15000$ Pa·s). In some embodiments, the composition may exhibit a low degree of stiffness (firmness <220 gf). In some embodiments, the composition may exhibit an easy sampling difficulty (yield strain <0.025%). In some embodiments, the composition may exhibit a medium resistance to oil release (crossover strain >8% and <25%). In some embodiments, the composition may exhibit an easy level of spreadability (tackiness <100 gf, stickiness <2000 gf.s).

In some embodiments, the composition may have a relative % UV absorption between 70-100%, e.g., about 70, 75, 80, 85, 90, 95, or 100%, greater than 70%, greater than 75%, greater than 80%, greater than 85%, greater than 90%, greater than 95%, less than 100%, less than 95%, less than 90%, less than 85%, less than 80%, less than 75%, between 70-75%, 75-80%, 80-85%, 85-90%, 90-95%, 95-100%, 70-80%, 75-85%, 80-90%, 85-95%, 90-100%, 70-85%, 75-90%, 80-95%, 85-100%, 70-90%, 75-95%, 80-100%, 70-95%, or 75-100%, a relative % visible light absorption between 3-7%, e.g., about 3, 4, 5, 6, or 7%, greater than 3%, greater than 4%, greater than 5%, greater than 6%, less than 7%, less than 6%, less than 5%, less than 4%, between 3-4%, 4-5%, 5-6%, 6-7%, 3-5%, 4-6%, 5-7%, 3-6%, or 4-7%, and a relative % near infrared light absorption between 10-14%, e.g., about 10, 11, 12, 13, or 14%, greater than 10%, greater than 11%, greater than 12%, greater than 13%, less than 14%, less than 13%, less than 12%, less than 11%, between 10-11%, 11-12%, 12-13%, 13-14%, 10-12%, 11-13%, 12-14%, 10-13%, or 11-14%.

In some embodiments, the composition may have a melting temperature of between 25° C. and 75° C., e.g., about 25, 30, 35, 40, 45, 50, 55, 60, 65, 70, or 75° C., greater than 25° C., greater than 30° C., greater than 35° C., greater than 40° C., greater than 45° C., greater than 50° C., greater than 55° C., greater than 60° C., greater than 65° C., greater than 70° C., less than 75° C., less than 70° C., less than 65° C., less than 60° C., less than 55° C., less than 50° C., less than 45° C., less than 40° C., less than 35° C., less than 30° C., between 25-30° C., 30-35° C., 35-40° C., 40-45° C., 45-50° C., 50-55° C., 55-60° C., 60-65° C., 65-70° C., 70-75° C., 25-35° C., 30-40° C., 35-45° C., 40-50° C., 45-55° C., 50-60° C., 55-65° C., 60-70° C., 65-75° C., 25-40° C., 30-45° C., 35-50° C., 40-55° C., 45-60° C., 50-65° C., 55-70° C., 60-75° C., 25-45° C., 30-50° C., 35-55° C., 40-60° C., 45-65° C., 50-70° C., 55-75° C., 25-50° C., 30-55° C., 35-60° C., 40-65° C., 45-70° C., 50-75° C., 25-55° C., 30-60° C., 35-65° C., 40-70° C., 45-75° C., 25-60° C., 30-65° C., 35-70° C., 40-75° C., 25-65° C., 30-70° C., 35-75° C., 25-70° C., or 30-75° C.

Table I provides various wax and oil gel compositions, their weight percents wax relative to the gel, and their thixotropy test results. Thixotropy test results are qualified as follows: "positive" results include full recovery of the viscosity (i.e., high thixotropy) of the gel after applied stress or no signs of syneresis, "neutral" results include a small layer of trapped oil, and "negative" results include observed signs of syneresis or no recovery of viscosity.

TABLE I

Composition wt % of various wax and oil gel compositions and the results of corresponding thixotropy tests.

| Wt % (w/w) wax in oil | CUW | RW | CW | BW | SFW |
|---|---|---|---|---|---|
| FSO | 5% | 6% | 3% | 4% | 2% |
| GSO | 5% | 6% | 3% | 4% | 2% |
| FCO | 4% | 8% | 4% | 15% | 2% |
| RO | 5% | 6% | 3% | 4% | 2% |

| Applied Force | | CUW | RW | CW | BW | SFW |
|---|---|---|---|---|---|---|
| SFO | scoop | neutral | neutral | positive | neutral | neutral |
|  | shear | negative | negative | positive | neutral | neutral |
| GSO | scoop | neutral | neutral | positive | neutral | neutral |
|  | shear | negative | neutral | positive | positive | neutral |
| FCO | scoop | neutral | neutral | neutral | positive | positive |
|  | shear | negative | negative | neutral | positive | neutral |
| RO | scoop | neutral | neutral | positive | neutral | positive |
|  | shear | negative | negative | neutral | positive | neutral |

Sunscreen Formulations

Exemplary sunscreen formulations of the disclosure are described as follows.

Upon determining the positive thixotropy results with gels made from certain waxes and oils from the previous section, various formulations, shown in Table II and listed as F1 to F10, were produced and tested to determine a combination with superior user experience.

The composition referred to as F1 includes about 4.30 wt % SFW, about 76.95 wt % FCO, and about 18.75 wt % ZnO. Such a composition could be formulated to include, e.g., about 2-5 wt % SFW, about 70-80 wt % FCO, and about 15-22 wt % ZnO.

The composition referred to as F2 includes about 2.15 wt % BW, about 2.15 wt % CW, about 76.95 wt % FCO, and about 18.75 wt % ZnO. Such a composition could be formulated to include, e.g., about 2-4 wt % BW, about 70-80 wt % FCO, and about 15-22 wt % ZnO.

The composition referred to as F3 includes about 4.30 wt % SFW, about 57.71 wt % FCO, about 19.24 wt % ABO, and about 18.75 wt % ZnO. Such a composition could be formulated to include, e.g., about 2-6 wt % SFW, about 50-65 wt % FCO, about 15-22 wt % ABO, and about 15-22 wt % ZnO.

The composition referred to as F4 includes about 2.15 wt % BW, about 2.15 wt % CW, about 57.71 wt % FCO, about 19.24 wt % ABO, and about 18.75 wt % ZnO. Such a composition could be formulated to include, e.g., about 1-5 wt % BW, about 50-65 wt % FCO, about 15-22 wt % ABO, and about 15-22 wt % ZnO.

The composition referred to as F5 includes about 4.30 wt % SFW, about 57.71 wt % FCO, about 19.24 wt % APO, and about 18.75 wt % ZnO. Such a composition could be formulated to include, e.g., about 2-6 wt % SFW, about 50-65 wt % FCO, about 15-22 wt % APO, and about 15-22 wt % ZnO.

The composition referred to as F6 includes about 2.15 wt % BW, about 2.15 wt % CW, about 57.71 wt % FCO, about 19.24 wt % APO, and about 18.75 wt % ZnO. Such a composition could be formulated to include, e.g., about 1-5 wt % BW, about 50-65 wt % FCO, about 15-22 wt % APO, and about 15-22 wt % ZnO.

The composition referred to as F7 includes about 4.30 wt % SFW, about 57.71 wt % FCO, about 19.24 wt % HEO, and about 18.75 wt % ZnO. Such a composition could be formulated to include, e.g., about 2-6 wt % SFW, about 50-65 wt % FCO, about 15-22 wt % HEO, and about 15-22 wt % ZnO.

The composition referred to as F8 includes about 2.15 wt % BW, about 2.15 wt % CW, about 57.71 wt % FCO, about 19.24 wt % HEO, and about 18.75 wt % ZnO. Such a composition could be formulated to include, e.g., about 1-5 wt % CW, about 50-65 wt % FCO, about 15-22 wt % HEO, and about 15-22 wt % ZnO.

The composition referred to as F9 includes about 4.30 wt % SFW, about 57.71 wt % FCO, about 19.24 wt % SEO, and about 18.75 wt % ZnO. Such a composition could be formulated to include, e.g., about 2-6 wt % SFW, about 50-65 wt % FCO, about 15-22 wt % SEO, and about 15-22 wt % ZnO.

The composition referred to as F10 includes about 2.15 wt % BW, about 2.15 wt % CW, about 57.71 wt % FCO, about 19.24 wt % SEO, and about 18.75 wt % ZnO. Such a composition could be formulated to include, e.g., about 1-5 wt % BW, about 50-65 wt % FCO, about 15-22 wt % SEO, and about 15-22 wt % ZnO.

The composition referred to as F11 includes greater than 10.00 wt % BW, SFO, Vitamin E, and about 18.75 wt % ZnO.

A sunscreen formulation of the disclosure, which is referred to herein as formulation F34, may include about 4.30 wt % SFW, about 76.75 wt % FCO, about 0.20 wt % vitamin E, and about 18.75 wt % ZnO.

A sunscreen formulation of the disclosure, which is referred to herein as the formulation F26, may include about 4.30 wt % SFW, about 71.25 wt % FCO, about 0.20 wt % vitamin E, about 3.50 wt % babassu starch, about 2.00 wt % seaweed extract, and about 18.75 wt % ZnO.

TABLE II

Formulations F1-F10 and their constituents.

| Material | F1 | F2 | F3 | F4 | F5 | F6 | F7 | F8 | F9 | F10 |
|---|---|---|---|---|---|---|---|---|---|---|
| SFW | 4.30 | 0.00 | 4.30 | 0.00 | 4.30 | 0.00 | 4.30 | 0.00 | 4.30 | 0.00 |
| BW | 0.00 | 2.15 | 0.00 | 2.15 | 0.00 | 2.15 | 0.00 | 2.15 | 0.00 | 2.15 |
| CW | 0.00 | 2.15 | 0.00 | 2.15 | 0.00 | 2.15 | 0.00 | 2.15 | 0.00 | 2.15 |
| FCO | 76.95 | 76.95 | 57.71 | 57.71 | 57.71 | 57.71 | 57.71 | 57.71 | 57.71 | 57.71 |
| ABO | 0.00 | 0.00 | 19.24 | 19.24 | 0.00 | 0.00 | 0.00 | 0.00 | 0.00 | 0.00 |
| APO | 0.00 | 0.00 | 0.00 | 0.00 | 19.24 | 19.24 | 0.00 | 0.00 | 0.00 | 0.00 |
| HEO | 0.00 | 0.00 | 0.00 | 0.00 | 0.00 | 0.00 | 19.24 | 19.24 | 0.00 | 0.00 |
| SEO | 0.00 | 0.00 | 0.00 | 0.00 | 0.00 | 0.00 | 0.00 | 0.00 | 19.24 | 19.24 |
| ZnO | 18.75 | 18.75 | 18.75 | 18.75 | 18.75 | 18.75 | 18.75 | 18.75 | 18.75 | 18.75 |
| % TOTAL | 100.00 | 100.00 | 100.00 | 100.00 | 100.00 | 100.00 | 100.00 | 100.00 | 100.00 | 100.00 |

Methods for Producing a Sunscreen Formulation

A sunscreen formulation, as described herein, can be produced by heating, mixing, and cooling the oil, wax, broad spectrum UV absorber, and/or additive components to form the composition. The method may further include increasing and decreasing the temperature of the composition at a specific rate. The method may further include mixing the composition at a fixed speed for a duration. In some embodiments, the method may further include adding the components, e.g., an oil component, a wax component, a broad spectrum UV absorber (e.g., ZnO particles), or an additive component, while heating, mixing, or cooling. In some embodiments, the method may further include adding the components under vacuum.

Heating Step

To combine the oil and wax components, first combine the components at a temperature sufficiently high (e.g., a temperature above the melting point of each of the components) to melt the components such that they form a uniform solution without solid structure that would alter the physical properties of the final product. For example, the method may include heating the component or components to a temperature of between 25° C. and 95° C., e.g., about 25, 30, 35, 40, 45, 50, 55, 60, 65, 70, 75, 80, 85, 90, or 95° C., greater than 25° C., greater than 30° C., greater than 35° C., greater than 40° C., greater than 45° C., greater than 50° C., greater than 55° C., greater than 60° C., greater than 65° C., greater than 70° C., greater than 75° C., greater than 80° C., greater than 85° C., greater than 90° C., less than 95° C., less than 90° C., less than 85° C., less than 80° C., less than 75° C., less than 70° C., less than 65° C., less than 60° C., less than 55° C., less than 50° C., less than 45° C., less than 40° C., less than 35° C., less than 30° C., between 25-30° C., 30-35° C., 35-40° C., 40-45° C., 45-50° C., 50-55° C., 55-60° C., 60-65° C., 65-70° C., 70-75° C., 75-80° C., 80-85° C., 85-90° C., 90-95° C., 25-35° C., 30-40° C., 35-45° C., 40-50° C., 45-55° C., 50-60° C., 55-65° C., 60-70° C., 65-75° C., 70-80° C., 75-85° C., 80-90° C., 85-95° C., 25-40° C., 30-45° C., 35-50° C., 40-55° C., 45-60° C., 50-65° C., 55-70° C., 60-75° C., 65-80° C., 70-85° C., 75-90° C., 80-95° C., 25-45° C., 30-50° C., 35-55° C., 40-60° C., 45-65° C., 50-70° C., 55-75° C., 60-80° C., 65-85° C., 70-90° C., 75-95° C., 25-50° C., 30-55° C., 35-60° C., 40-65° C., 45-70° C., 50-75° C., 55-80° C., 60-85° C., 65-90° C., 70-95° C., 25-55° C., 30-60° C., 35-65° C., 40-70° C., 45-75° C., 50-80° C., 55-85° C., 60-90° C., 65-95° C., 25-60° C., 30-65° C., 35-70° C., 40-75° C., 45-80° C., 50-85° C., 55-90° C., 60-95° C., 25-65° C., 30-70° C., 35-75° C., 40-80° C., 45-85° C., 50-90° C., 55-95° C., 25-70° C., 30-75° C., 35-80° C., 40-85° C., 45-90° C., 25-75° C., 30-80° C., 35-85° C., 40-90° C., 45-95° C., 25-80° C., 30-85° C., 35-90° C., 40-95° C., 25-85° C., 30-90° C., 35-95° C., 25-90° C., or 30-95° C. The method may include heating the component or components at a rate of between 0.1 to 10° C./min, e.g., about 0.1, 0.5, 1, 2, 3, 4, 5, 6, 7, 8, 9, or 10° C./min, greater than 0.1° C./min, greater than 0.5° C./min, greater than 1° C./min, greater than 2° C./min, greater than 3° C./min, greater than 4° C./min, greater than 5° C./min, greater than 6° C./min, greater than 7° C./min, greater than 8° C./min, greater than 9° C./min, less than 10° C./min, less than 9° C./min, less than 8° C./min, less than 7° C./min, less than 6° C./min, less than 5° C./min, less than 4° C./min, less than 3° C./min, less than 2° C./min, less than 1° C./min, less than 0.5° C./min, between 0.1-0.5° C./min, 0.5-1° C./min, 1-2° C./min, 2-3° C./min, 3-4° C./min, 4-5° C./min, 5-6° C./min, 6-7° C./min, 7-8° C./min, 8-9° C./min, 9-10° C./min, 0.1-1° C./min, 0.5-2° C./min, 1-3° C./min, 2-4° C./min, 3-5° C./min, 4-6° C./min, 5-7° C./min, 6-8° C./min, 7-9° C./min, 8-10° C./min, 0.1-2° C./min, 0.5-3° C./min, 1-4° C./min, 2-5° C./min, 3-6° C./min, 4-7° C./min, 5-8° C./min, 6-9° C./min, 7-10° C./min, 0.1-3° C./min, 0.5-4° C./min, 1-5° C./min, 2-6° C./min, 3-7° C./min, 4-8° C./min, 5-9° C./min, 6-10° C./min, 0.1-4° C./min, 0.5-5° C./min, 1-6° C./min, 2-7° C./min, 3-8° C./min, 4-9° C./min, 5-10° C./min, 0.1-5° C./min, 0.5-6° C./min, 1-7° C./min, 2-8° C./min, 3-9° C./min, 4-10° C./min, 0.1-6° C./min, 0.5-7° C./min, 1-8° C./min, 2-9° C./min, 3-10° C./min, 0.1-7° C./min, 0.5-8° C./min, 1-9° C./min, 2-10° C./min, 0.1-8° C./min, 0.5-9° C./min, 0.1-9° C./min, or 0.5-10° C./min.

Cooling Step

After a heating step, as discussed in the prior paragraph, and once the components are sufficiently melted to form a uniform solution, the method further includes a cooling step. For example, the component or components can be cooled to a temperature of between 25° C. and 85° C., e.g., about 25, 30, 35, 40, 45, 50, 55, 60, 65, 70, 75, 80, or 85° C., greater than 25° C., greater than 30° C., greater than 35° C., greater than 40° C., greater than 45° C., greater than 50° C., greater than 55° C., greater than 60° C., greater than 65° C., greater than 70° C., greater than 75° C., greater than 80° C., less than 85° C., less than 80° C., less than 75° C., less than 70° C., less than 65° C., less than 60° C., less than 55° C., less than 50° C., less than 45° C., less than 40° C., less than 35° C., less than 30° C., between 25-30° C., 30-35° C., 35-40° C., 40-45° C., 45-50° C., 50-55° C., 55-60° C., 60-65° C., 65-70° C., 70-75° C., 75-80° C., 80-85° C., 25-35° C., 30-40° C., 35-45° C., 40-50° C., 45-55° C., 50-60° C., 55-65° C., 60-70° C., 65-75° C., 70-80° C., 75-85° C., 25-40° C., 30-45° C., 35-50° C., 40-55° C., 45-60° C., 50-65° C., 55-70° C., 60-75° C., 65-80° C., 70-85° C., 25-45° C., 30-50° C., 35-55° C., 40-60° C., 45-65° C., 50-70° C., 55-75° C., 60-80° C., 65-85° C., 25-50° C., 30-55° C., 35-60° C., 40-65° C., 45-70° C., 50-75° C., 55-80° C., 60-85° C., 25-55° C., 30-60° C., 35-65° C., 40-70° C., 45-75° C., 50-80° C., 55-85° C., 25-60° C., 30-65° C., 35-70° C., 40-75° C., 45-80° C., 50-85° C., 25-65° C., 30-70° C., 35-75° C., 40-80° C., 45-85° C., 25-70° C., 30-75° C., 35-80° C., 40-85° C., 25-75° C., 30-80° C., 35-85° C., 25-80° C., 30-85° C., or 25-85° C. The method may include cooling the component or components at a rate of between 0.1 to 10° C./min, e.g., about 0.1, 0.5, 1, 2, 3, 4, 5, 6, 7, 8, 9, or 10° C./min, greater than 0.1° C./min, greater than 0.5° C./min, greater than 1° C./min, greater than 2° C./min, greater than 3° C./min, greater than 4° C./min, greater than 5° C./min, greater than 6° C./min, greater than 7° C./min, greater than 8° C./min, greater than 9° C./min, less than 10° C./min, less than 9° C./min, less than 8° C./min, less than 7° C./min, less than 6° C./min, less than 5° C./min, less than 4° C./min, less than 3° C./min, less than 2° C./min, less than 1° C./min, less than 0.5° C./min, between 0.1-0.5° C./min, 0.5-1° C./min, 1-2° C./min, 2-3° C./min, 3-4° C./min, 4-5° C./min, 5-6° C./min, 6-7° C./min, 7-8° C./min, 8-9° C./min, 9-10° C./min, 0.1-1° C./min, 0.5-2° C./min, 1-3° C./min, 2-4° C./min, 3-5° C./min, 4-6° C./min, 5-7° C./min, 6-8° C./min, 7-9° C./min, 8-10° C./min, 0.1-2° C./min, 0.5-3° C./min, 1-4° C./min, 2-5° C./min, 3-6° C./min, 4-7° C./min, 5-8° C./min, 6-9° C./min, 7-10° C./min, 0.1-3° C./min, 0.5-4° C./min, 1-5° C./min, 2-6° C./min, 3-7° C./min, 4-8° C./min, 5-9° C./min, 6-10° C./min, 0.1-4° C./min, 0.5-5° C./min, 1-6° C./min, 2-7° C./min, 3-8° C./min, 4-9° C./min, 5-10° C./min, 0.1-5° C./min, 0.5-6° C./min, 1-7° C./min, 2-8° C./min, 3-9° C./min, 4-10° C./min, 0.1-6° C./min, 0.5-7° C./min, 1-8° C./min, 2-9° C./min, 3-10° C./min, 0.1-7° C./min, 0.5-8° C./min, 1-9° C./min, 2-10° C./min, 0.1-8° C./min, 0.5-9° C./min, 0.1-9° C./min, or 0.5-10° C./min. The method may further include confirmation of completion of the cooling step once the mixture reaches a target temperature, also known as a set temperature. The method may include cooling the composition into a flowable gel.

Mixing Step

During the heating step, between the heating and cooling step(s), and intermittently through the cooling step(s) as components are added, the method may further include a mixing step. The method may include mixing in the form of stirring. For example, the component or components can be mixed at a rate of between 0.05 $s^{-1}$ and 25 $s^{-1}$, e.g., 0.05, 0.1, 0.15, 0.2, 0.25, 0.5, 1, 2, 5, 10, 12, 15, 20, 22, or 25 $s^{-1}$, greater than 0.05 $s^{-1}$, greater than 0.1 $s^{-1}$, greater than 0.15 $s^{-1}$, greater than 0.2 $s^{-1}$, greater than 0.25 $s^{-1}$, greater than 0.5 $s^{-1}$, greater than 1 $s^{-1}$, greater than 2 $s^{-1}$, greater than 5 $s^{-1}$, greater than 10 $s^{-1}$, greater than 12 $s^{-1}$, greater than 15 $s^{-1}$, greater than 20 $s^{-1}$, greater than 22 $s^{-1}$, less than 25 $s^{-1}$, less than 22 $s^{-1}$, less than 20 $s^{-1}$, less than 15 $s^{-1}$, less than 12 $s^{-1}$, less than 10 $s^{-1}$, less than 5 $s^{-1}$, less than 2 $s^{-1}$, less than 1 $s^{-1}$, less than 0.5 $s^{-1}$, less than 0.25 $s^{-1}$, less than 0.2 $s^{-1}$, less than 0.15 $s^{-1}$, less than 0.1 $s^{-1}$, between 0.05-0.1 $s^{-1}$, 0.1-0.15 $s^{-1}$, 0.15-0.2 $s^{-1}$, 0.2-0.25 $s^{-1}$, 0.25-0.5 $s^{-1}$, 0.5-1 $s^{-1}$, 1-2 $s^{-1}$, 2-5 $s^{-1}$, 5-10 $s^{-1}$, 10-12 $s^{-1}$, 12-15 $s^{-1}$, 15-20 $s^{-1}$, 20-22 $s^{-1}$, 22-25 $s^{-1}$, 0.05-0.15 $s^{-1}$, 0.1-0.2 $s^{-1}$, 0.15-0.25 $s^{-1}$, 0.2-0.5 $s^{-1}$, 0.25-1 $s^{-1}$, 0.5-2 $s^{-1}$, 1-5 $s^{-1}$, 2-10 $s^{-1}$, 5-12 $s^{-1}$, 10-15 $s^{-1}$, 12-20 $s^{-1}$, 15-22 $s^{-1}$, 20-25 $s^{-1}$, 0.05-0.2 $s^{-1}$, 0.1-0.25 $s^{-1}$, 0.15-0.5 $s^{-1}$, 0.2-1 $s^{-1}$, 0.25-2 $s^{-1}$, 0.5-5 $s^{-1}$, 1-10 $s^{-1}$, 2-12 $s^{-1}$, 5-15 $s^{-1}$, 10-20 $s^{-1}$, 12-22 $s^{-1}$, 15-25 $s^{-1}$, 0.05-0.25 $s^{-1}$, 0.1-0.5 $s^{-1}$, 0.15-1 $s^{-1}$, 0.2-2 $s^{-1}$, 0.25-5 $s^{-1}$, 0.5-10 $s^{-1}$, 1-12 $s^{-1}$, 2-15 $s^{-1}$, 5-20 $s^{-1}$, 10-22 $s^{-1}$, 12-25 $s^{-1}$, 0.05-0.5 $s^{-1}$, 0.1-1 $s^{-1}$, 0.15-2 $s^{-1}$, 0.2-5 $s^{-1}$, 0.25-10 $s^{-1}$, 0.5-12 $s^{-1}$, 1-15 $s^{-1}$, 2-20 $s^{-1}$, 5-25 $s^{-1}$, 0.05-1 $s^{-1}$, 0.1-2 $s^{-1}$, 0.15-5 $s^{-1}$, 0.2-10 $s^{-1}$, 0.25-12 $s^{-1}$, 0.5-15 $s^{-1}$, 1-20 $s^{-1}$, 2-22 $s^{-1}$, 5-25 $s^{-1}$, 0.05-2 $s^{-1}$, 0.1-5 $s^{-1}$, 0.15-10 $s^{-1}$, 0.2-15 $s^{-1}$, 0.25-20 $s^{-1}$, 0.5-22 $s^{-1}$, 1-25 $s^{-1}$, 2-25 $s^{-1}$, 0.05-5 $s^{-1}$, 0.1-10 $s^{-1}$, 0.15-15 $s^{-1}$, 0.2-20 $s^{-1}$, 0.25-22 $s^{-1}$, 0.5-25 $s^{-1}$, 0.05-10 $s^{-1}$, 0.1-15 $s^{-1}$, 0.15-20 $s^{-1}$, 0.2-22 $s^{-1}$, 0.25-25 $s^{-1}$, 0.05-15 $s^{-1}$, 0.1-20 $s^{-1}$, 0.15-22 $s^{-1}$, 0.2-25 $s^{-1}$, 0.05-20 $s^{-1}$, 0.1-22 $s^{-1}$, 0.15-25 $s^{-1}$, 0.05-22 $s^{-1}$, or 0.1-25 $s^{-1}$.

The method may further include mixing with one or more mixers. The method may further include mixing with a central mixer, an anchor mixer, a rotor stator, or a combination thereof.

Holding Step

Figure 25:
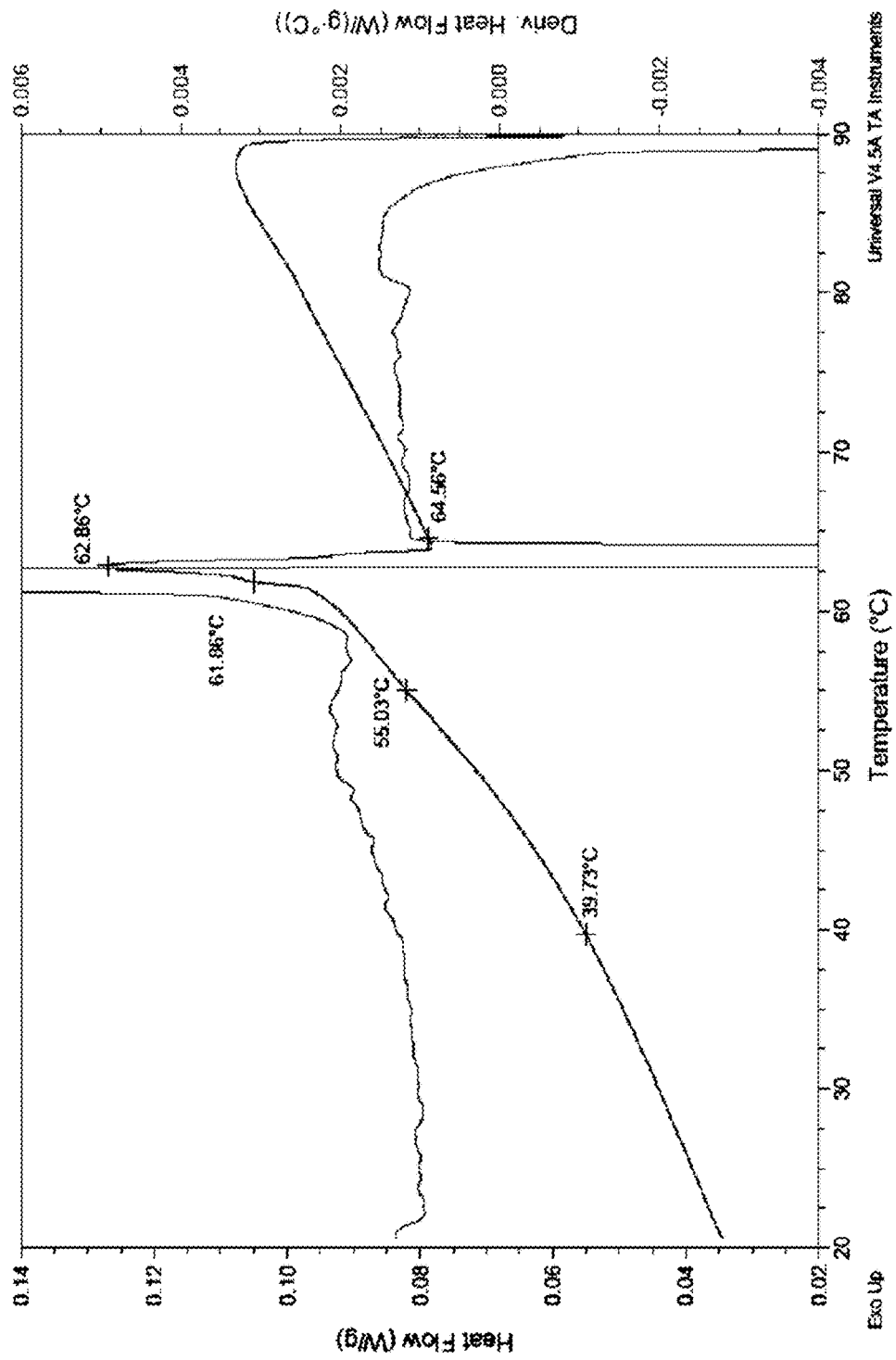
FIG. 25 is a plot showing a high resolution crystallization differential scanning calorimetry (DSC) of F1 to determine all intermediate crystallization temperatures between the start of and completion of the crystallization manifold. The derivative of the heat flow was plotted as well to verify the locations of the peaks, as the peaks in the heat flow derivative plot corresponded to places where the slope changed drastically, e.g., inflection points and peaks.
Figure 26:
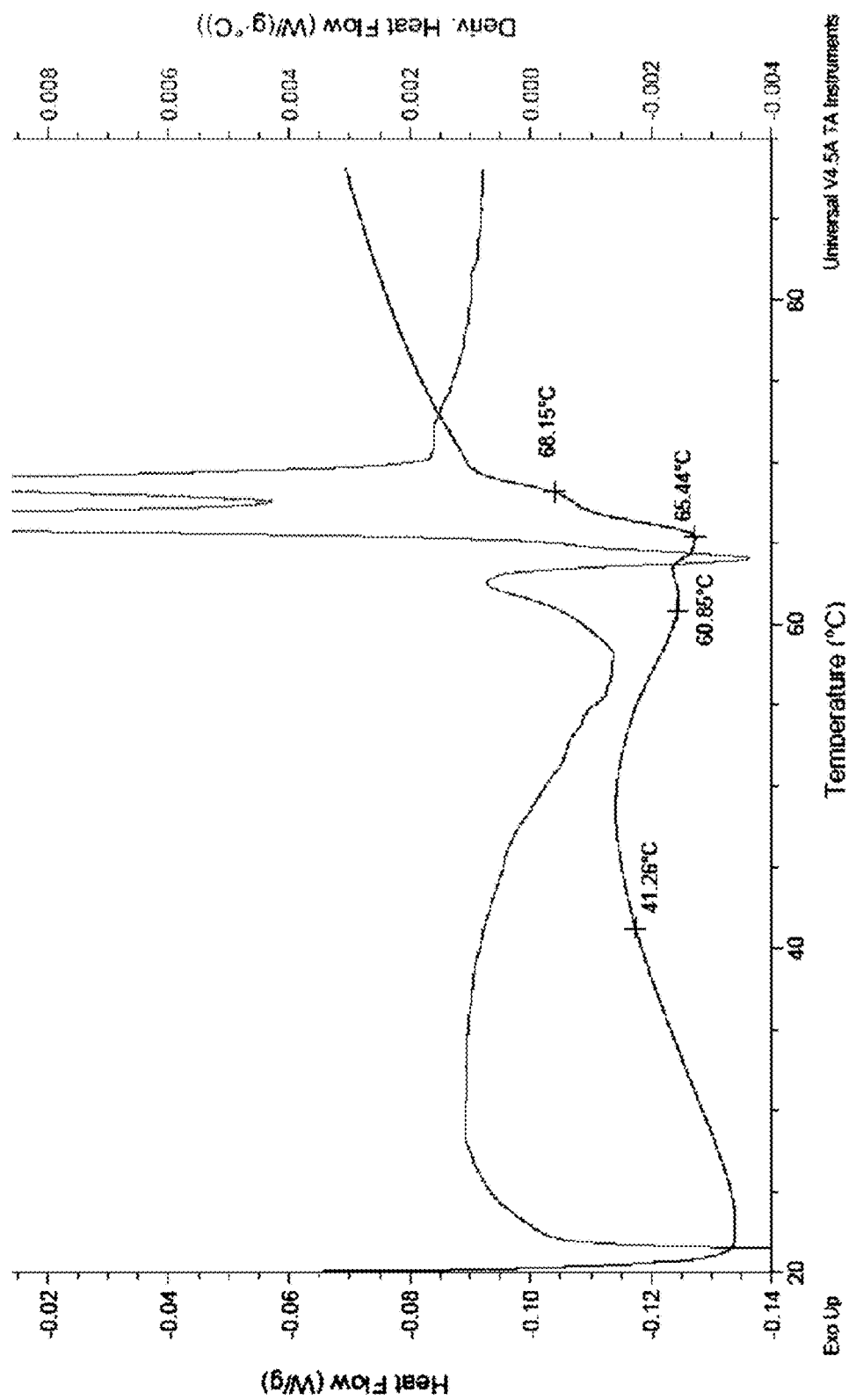
FIG. 26 is a plot showing a high resolution melting DSC of F1 to determine all intermediate melting temperatures between onset of and completion of the melting manifold. The derivative of the heat flow was plotted as well to verify the locations of the peaks, as the peaks in the heat flow derivative plot corresponded to places where the slope changed drastically, e.g., inflection points and peaks.

Intermittently through the cooling step, the method may further include a holding step, in which the composition is mixed or allowed to rest at a constant temperature for a set period of time. As shown in FIGS. 25 and 26, the melting and crystallizing temperatures of the compositions feature multiple peaks, indicating the formation of intermediate solid or liquid phases between the pure solid and pure liquid phases. The holding step takes into account the formation of these intermediate phases by allowing the solid to form more of these intermediate phases in the process of solidification, thereby changing the structure of composition to improve its stability and texture. The method may also include resting or mixing the component or components at a certain mix rate and/or certain temperature for between 1 and 800 minutes, e.g. about 1, 2, 5, 10, 12, 15, 20, 25, 30, 45, 60, 75, 90, 105, 120, 150, 180, 210, 240, 270, 300, 330, 360, 390, 420, 450, 480, 510, 540, 570, 600, 650, 700, 750, or 800 minutes, greater than 1 min, greater than 2 min, greater than 5 min, greater than 10 min, greater than 12 min, greater than 15 min, greater than 20 min, greater than 25 min, greater than 30 min, greater than 45 min, greater than 60 min, greater than 75 min, greater than 90 min, greater than 105 min, greater than 120 min, greater than 150 min, greater than 180 min, greater than 210 min, greater than 240 min, greater than 270 min, greater than 300 min, greater than 330 min, greater than 360 min, greater than 390 min, greater than 420 min, greater than 450 min, greater than 480 min, greater than 510 min, greater than 540 min, greater than 570 min, greater than 650 min, greater than 700 min, greater than 750 min, less than 800 min, less than 750 min, less than 700 min, less than 600 min, less than 570 min, less than 540 min, less than 510 min, less than 480 min, less than 450 min, less than 420 min, less than 390 min, less than 360 min, less than 330 min, less than 300 min, less than 270 min, less than 240 min, less than 210 min, less than 180 min, less than 150 min, less than 120 min, less than 75 min, less than 60 min, less than 45 min, less than 30 min, less than 25 min, less than 20 min, less than 15 min, less than 12 min, less than 10 min, less than 5 min, less than 2 min, between 1-2 min, 2-5 min, 5-10 min, 10-12 min, 12-15 min, 15-20 min, 20-25 min, 25-30 min, 30-45 min, 45-60 min, 60-75 min, 75-90 min, 90-105 min, 105-120 min, 120-150 min, 150-180 min, 180-210 min, 210-240 min, 240-270 min, 270-300 min, 300-330 min, 330-360 min, 360-390 min, 390-420 min, 420-450 min, 450-480 min, 480-510 min, 510-540 min, 540-570 min, 570-600 min, 600-650 min, 650-700 min, 700-750 min, 750-800 min, 1-5 min, 2-10 min, 5-12 min, 10-15 min, 12-20 min, 15-25 min, 20-30 min, 25-45 min, 30-60 min, 45-75 min, 60-90 min, 75-105 min, 90-120 min, 105-150 min, 120-180 min, 150-210 min, 180-240 min, 210-270 min, 240-300 min, 270-330 min, 300-360 min, 330-390 min, 360-420 min, 390-450 min, 420-480 min, 450-510 min, 480-540 min, 510-570 min, 540-600 min, 570-650 min, 600-700 min, 650-750 min, 700-800 min, 1-10 min, 2-12 min, 5-15 min, 10-20 min, 12-25 min, 15-30 min, 20-45 min, 25-60 min, 30-75 min, 45-90 min, 60-105 min, 75-120 min, 90-150 min, 105-180 min, 120-210 min, 150-240 min, 180-270 min, 210-300 min, 240-330 min, 270-360 min, 300-390 min, 330-420 min, 360-450 min, 390-480 min, 420-510 min, 450-540 min, 480-570 min, 510-600 min, 540-650 min, 570-700 min, 600-750 min, 650-800 min, 1-12 min, 2-15 min, 5-20 min, 10-25 min, 12-30 min, 15-45 min, 20-60 min, 25-75 min, 30-90 min, 45-105 min, 60-120 min, 75-150 min, 90-180 min, 105-210 min, 120-240 min, 150-270 min, 180-300 min, 210-330 min, 240-360 min, 270-390 min, 300-420 min, 330-450 min, 360-480 min, 390-510 min, 420-540 min, 450-570 min, 480-600 min, 510-650 min, 540-700 min, 570-750 min, 600-800 min, 1-15 min, 2-20 min, 5-25 min, 10-30 min, 12-45 min, 15-60 min, 20-75 min, 25-90 min, 30-105 min, 45-120 min, 60-150 min, 75-180 min, 90-210 min, 105-240 min, 120-270 min, 150-300 min, 180-330 min, 210-360 min, 240-390 min, 270-420 min, 300-450 min, 330-480 min, 360-510 min, 390-540 min, 420-570 min, 450-600 min, 480-650 min, 510-700 min, 540-750 min, 570-800 min, 1-20 min, 2-25 min, 5-30 min, 10-45 min, 12-60 min, 15-75 min, 20-90 min, 25-105 min, 30-120 min, 45-150 min, 60-180 min, 75-210 min, 90-240 min, 105-270 min, 120-300 min, 150-330 min, 180-360 min, 210-390 min, 240-420 min, 270-450 min, 300-480 min, 330-510 min, 360-540 min, 390-570 min, 420-600 min, 450-650 min, 480-700 min, 510-750 min, 540-800 min, 1-25 min, 2-30 min, 5-45 min, 10-60 min, 12-75 min, 15-90 min, 20-105 min, 25-120 min, 30-150 min, 45-180 min, 60-210 min, 75-240 min, 90-270 min, 105-300 min, 120-330 min, 150-360 min, 180-390 min, 210-420 min, 240-450 min, 270-480 min, 300-510 min, 330-540 min, 360-570 min, 390-600 min, 420-650 min, 450-700 min, 480-750 min, 510-800 min, 1-30 min, 2-45 min, 5-60 min, 10-75 min, 12-90 min, 15-105 min, 20-120 min, 25-150 min, 30-180 min, 45-210 min, 60-240 min, 75-270 min, 90-300 min, 105-330 min, 120-360 min, 150-390 min, 180-420 min, 210-450 min, 240-480 min, 270-510 min, 300-540 min, 330-570 min, 360-600 min, 390-650 min, 420-700 min, 450-750 min, 480-800 min, 1-45 min, 2-60 min, 5-75 min, 10-90 min, 12-105 min, 15-120 min, 20-150 min, 25-180 min, 30-210 min, 45-240 min, 60-270 min, 75-300 min, 90-330 min, 105-360 min, 120-390 min, 150-420 min, 180-450 min, 210-480 min, 240-510 min, 270-540 min, 300-570 min, 330-600 min, 360-650 min, 390-700 min, 420-750 min, 450-800 min, 1-60 min, 2-75 min, 5-90 min, 10-105 min, 12-120 min, 15-150 min, 20-180 min, 25-210 min, 30-240 min, 45-270 min, 60-300 min, 75-330 min, 90-360 min, 105-390 min, 120-420 min, 150-450 min, 180-480 min, 210-510 min, 240-540 min, 270-570 min, 300-600 min, 330-650 min, 360-700 min, 390-750 min, 420-800 min, 1-75 min, 2-90 min, 5-105 min, 10-120 min, 12-150 min, 15-180 min, 20-210 min, 25-240 min, 30-270 min, 45-300 min, 60-330 min, 75-360 min, 90-390 min, 105-420 min, 120-450 min, 150-480 min, 180-510 min, 210-540 min, 240-570 min, 270-600 min, 300-650 min, 330-700 min, 360-750 min, 390-800 min, 1-90 min, 2-105 min, 5-120 min, 10-150 min, 12-180 min, 15-210 min, 20-240 min, 25-270 min, 30-300 min, 45-330 min, 60-360 min, 75-390 min, 90-420 min, 105-450 min, 120-480 min, 150-510 min, 180-540 min, 210-570 min, 240-600 min, 270-650 min, 300-700 min, 330-750 min, 360-800 min, 1-105 min, 2-120 min, 5-150 min, 10-180 min, 12-210 min, 15-240 min, 20-270 min, 25-300 min, 30-330 min, 45-360 min, 60-390 min, 75-420 min, 90-450 min, 105-480 min, 120-510 min, 150-540 min, 180-570 min, 210-600 min, 240-650 min, 270-700 min, 300-750 min, 330-800 min, 1-120 min, 2-150 min, 5-180 min, 10-210 min, 12-240 min, 15-270 min, 20-300 min, 25-330 min, 30-360 min, 45-390 min, 60-420 min, 75-450 min, 90-480 min, 105-510 min, 120-540 min, 150-570 min, 180-600 min, 210-650 min, 240-700 min, 270-750 min, 300-800 min, 1-150 min, 2-180 min, 5-210 min, 10-240 min, 12-270 min, 15-300 min, 20-330 min, 25-360 min, 30-390 min, 45-420 min, 60-450 min, 75-480 min, 90-510 min, 105-540 min, 120-570 min, 150-600 min, 180-650 min, 210-700 min, 240-750 min, 270-800 min, 1-180 min, 2-210 min, 5-240 min, 10-270 min, 12-300 min, 15-330 min, 20-360 min, 25-390 min, 30-420 min, 45-450 min, 60-480 min, 75-510 min, 90-540 min, 105-570 min, 120-600 min, 150-650 min, 180-700 min, 210-750 min, 240-800 min, 1-210 min, 2-240 min, 5-270 min, 10-300 min, 12-330 min, 15-360 min, 20-390 min, 25-420 min, 30-450 min, 45-480 min, 60-510 min, 75-540 min, 90-570 min, 105-600 min, 120-650 min, 150-700 min, 180-750 min, 210-800 min, 1-240 min, 2-270 min, 5-300 min, 10-330 min, 12-360 min, 15-390 min, 20-420 min, 25-450 min, 30-480 min, 45-510 min, 60-540 min, 75-570 min, 90-600 min, 105-650 min, 120-700 min, 150-750 min, 180-800 min, 1-270 min, 2-300 min, 5-330 min, 10-360 min, 12-390 min, 15-420 min, 20-450 min, 25-480 min, 30-510 min, 45-540 min, 60-570 min, 75-600 min, 90-650 min, 105-700 min, 120-750 min, 150-800 min, 1-300 min, 2-330 min, 5-360 min, 10-390 min, 12-420 min, 15-450 min, 20-480 min, 25-510 min, 30-540 min, 45-570 min, 60-600 min, 75-650 min, 90-700 min, 105-750 min, 120-800 min, 1-330 min, 2-360 min, 5-390 min, 10-420 min, 12-450 min, 15-480 min, 20-510 min, 25-540 min, 30-570 min, 45-600 min, 60-650 min, 75-700 min, 90-750 min, 105-800 min, 1-360 min, 2-390 min, 5-420 min, 10-450 min, 12-480 min, 15-510 min, 20-540 min, 25-570 min, 30-600 min, 45-650 min, 60-700 min, 75-750 min, 90-800 min, 1-390 min, 2-420 min, 5-450 min, 10-480 min, 12-510 min, 15-540 min, 20-570 min, 25-600 min, 30-650 min, 45-700 min, 60-750 min, 75-800 min, 1-420 min, 2-450 min, 5-480 min, 10-510 min, 12-540 min, 15-570 min, 20-600 min, 25-650 min, 30-700 min, 45-750 min, 60-800 min, 1-450 min, 2-480 min, 5-510 min, 10-540 min, 12-570 min, 15-600 min, 20-650 min, 25-700 min, 30-750 min, 45-800 min, 1-480 min, 2-510 min, 5-540 min, 10-570 min, 12-600 min, 15-650 min, 20-700 min, 25-750 min, 30-800 min, 1-510 min, or 2-540 min. 5-570 min, 10-600 min, 12-650 min, 15-700 min, 20-750 min, 25-800 min, 1-540 min, or 2-570 min. 5-600 min, 10-650 min, 12-700 min, 15-750 min, 20-800 min, 1-570 min, 2-600 min, 5-650 min, 10-700 min, 12-750 min, 15-800 min, 1-600 min, 2-650 min, 5-700 min, 10-750 min, 12-800 min, 1-650 min, 2-700 min, 5-750 min, 10-800 min, 1-700 min, 2-750 min, 5-800 min, 1-750 min, or 2-800 min.

Component Addition Step

Intermittently through the cooling step, the method may further include a component addition step, in which additional components (e.g., broad spectrum UV absorber (e.g., ZnO), vitamin E, babassu starch, seaweed extract, etc.) are added to the combined components, optionally, e.g., under vacuum. The method may include adding a component under a vacuum of between 0.1 to 1 bar below atmospheric pressure, e.g., about 0.1, 0.2, 0.3, 0.4, 0.5, 0.6, 0.7, 0.8, 0.9, or 1 bar below atmospheric pressure. The component may be added under vacuum during a heating, cooling, or mixing step. For example, the method may include adding a component under a vacuum of about 0.2-0.6 bar (e.g., 0.3, 0.4, or 0.5 bar) below atmospheric pressure, optionally while heating, mixing, or cooling.

Method for Forming a Sunscreen Composition

A sunscreen composition of the disclosure can be prepared using a method that includes the aforementioned heating, cooling, mixing, holding, and/or component addition steps. The method may be performed, as follows.

The oil and wax components may be combined and heated to about 50-95° C. with or without mixing. Then, a broad spectrum UV absorber (e.g., zinc oxide or titanium dioxide) may be added while mixing with or without high shear. The broad spectrum UV absorber may be dispersed with or without vacuum with high shear mixing for about 1-800 minutes. The components can then be cooled with or without vacuum to about 40-85° C. while mixing with or without high shear mixer. Then an additive(s) (e.g., tocopherol or a combination of tocopherol, SEPIFINE™ (babassu starch), and ANTILEUKINE™ 6) may be added and dispersed into the mix with or without mixing at any point during the process for about 1-800 minutes. The composition may be held at about 40-85° C. for about 0-800 min while mixing. The components may be cooled in one step to about 25-80° C. while mixing or using a second cooling step and then may be further cooled to about 25-60° C. while mixing. The components may be transferred from the main vessel to a side vessel for filling or filled directly from main vessel with or without mixing with optional use of recirculation of the composition with or without control of the temperature from 25-65° C. The composition may be filled in the final containers with or without mixing.

Method for Forming a Sunscreen Composition Using a High Melting Temperature Wax(es)

A sunscreen composition of the disclosure containing a high melting temperature wax, or a combination of different high melting temperature waxes, can be prepared using a method that includes the aforementioned heating, cooling, mixing, holding, and/or component addition steps. The method may be performed, as follows.

The oil and wax components may be combined and heated to about 75-95° C. while mixing. Then, a broad spectrum UV absorber component may be added while mixing. Then a broad spectrum UV absorber component (e.g., zinc oxide or titanium dioxide) may be dispersed with or without vacuum with or without a high shear mixing for about 1-800 minutes. The components can then be cooled with or without vacuum to about 62-74° C. while mixing with or without a high shear mixer. Then an additive(s) (e.g., tocopherol or a combination of tocopherol, SEPIFINE™ (babassu starch), and ANTILEUKINE™ 6) may be added and dispersed into the mix with or without mixing for about 1-800 minutes. The composition may be held at about 62-74° C. for about 0-800 min while mixing. The components may be cooled to about 48-61° C. while mixing. The components may be transferred from the main vessel to a side vessel for filling or filled directly from main vessel with or without mixing with optional use of recirculation of the composition with control of the temperature from 48-61° C. The composition may be filled in the final containers with or without mixing.

Method for Forming a Sunscreen Composition Using a Low Melting Temperature Wax(es)

A sunscreen composition of the disclosure containing a low melting temperature wax, or a combination of different low melting temperature waxes, can be prepared using a method that includes the aforementioned heating, cooling, mixing, holding, and/or component addition steps. The method may be performed, as follows.

The oil and wax components (e.g., Fractionated coconut oil and candelilla wax) may be combined and heated to about 55-95° C. with mixing. Then, a broad spectrum UV absorber (e.g., zinc oxide or titanium dioxide) may be added while mixing. The broad spectrum UV absorber may be dispersed with or without vacuum with or without a high shear mixing for about 1-800 minutes. The components can then be cooled with or without vacuum to about 40-68° C. while mixing with or without a high shear mixer. Then an additive(s) (e.g., tocopherol or a combination of tocopherol, SEPIFINE™ (babassu starch), and ANTILEUKINE™ 6) may be added and dispersed into the mix with or without while mixing for about 1-800 minutes. The composition may be held at about 40-68° C. for about 0-800 min while mixing. The components may be cooled to about 25-48° C. while mixing. The components may be transferred from the main vessel to a side vessel for filling or filled directly from main vessel with or without mixing with optional use of recirculation of the composition with control of the temperature from 25-48° C. The composition may be filled in the final containers with or without mixing.

Method for Forming a Formulation F34 Composition

Figure 34:
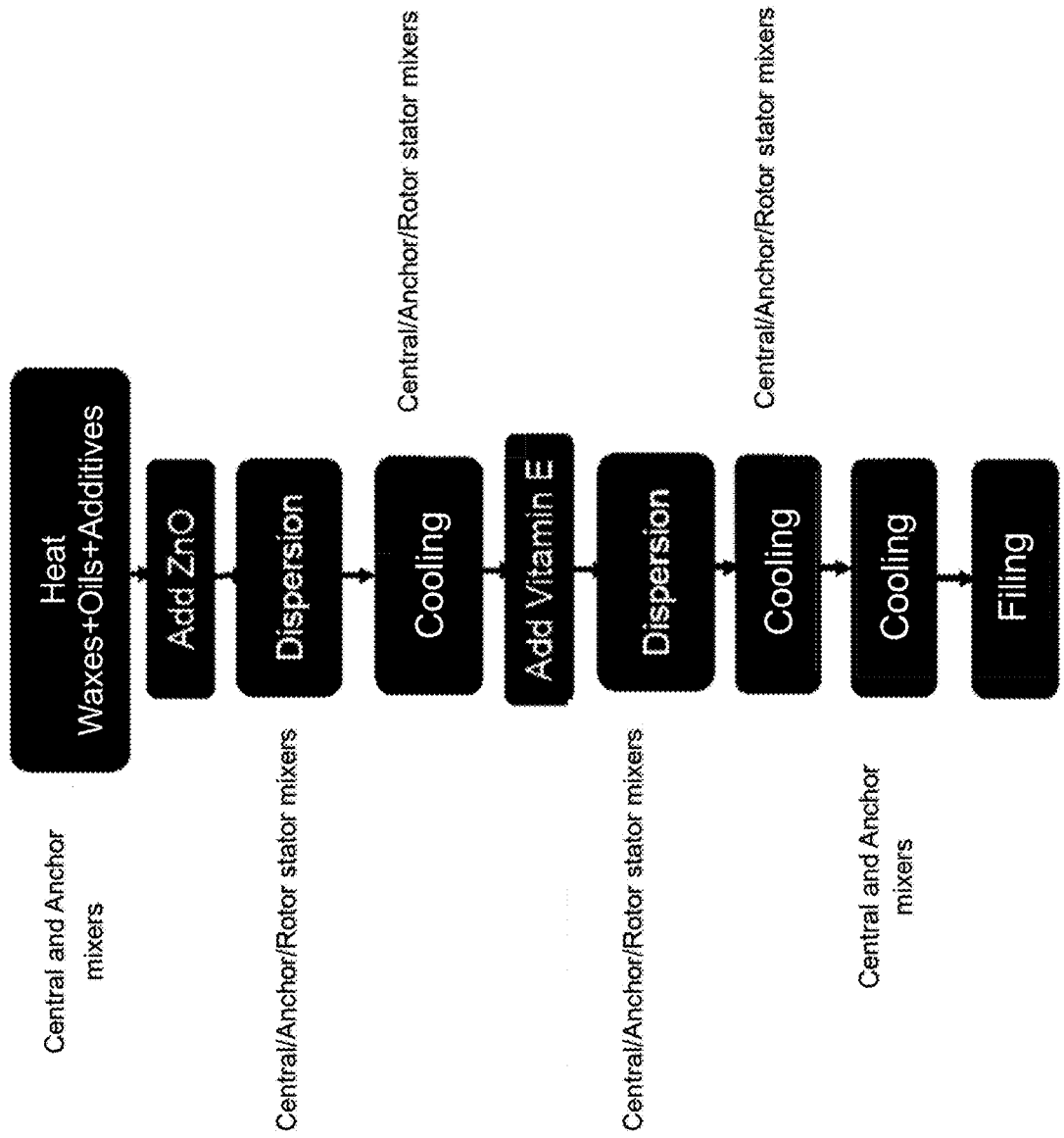
FIG. 34 is a scheme showing a manufacturing process that includes the NSFW. First, waxes and oils were heated to form a homogeneous liquid composition and mixed. Next, ZnO particles were added, disperse, cooled, further dispersed, and cooled, before vitamin E was added. The composition was mixed to disperse the vitamin E, cooled further, mixed to disperse further, cooled further, and transferred.

A composition corresponding to Formulation F34 was observed to produce an optimal user experience when applied to skin. Formulation F34 can be prepared by a combination of the aforementioned heating, cooling, mixing, holding, and component addition steps. The method of preparation is illustrated, e.g., in FIG. 34, and is described as follows.

The oil and wax components may be about 76.75 wt % FCO and about 4.3 wt % SFW, respectively, and may be combined and heated to about 75-85° C. (e.g., 80° C., 82° C., or 83° C.) with mixing (e.g., using a central mixer at about 0.40-0.47 $s^{-1}$ (e.g., 0.42, 0.43, or 0.46 $s^{-1}$) and an anchor mixer at about 0.23-0.27 $s^{-1}$ (e.g., 0.23, 0.25, or 0.27 $s^{-1}$)). Then, zinc oxide (18.75 wt %) may be added while mixing (e.g., with the central mixer at about 0.40-0.47 $s^{-1}$ (e.g., 0.42, 0.43, or 0.46 $s^{-1}$), the anchor mixer at about 0.23-0.27

$s^{-1}$ (e.g., 0.23, 0.25, or 0.27 $s^{-1}$), and the rotor stator at about 20.00-21.50 $s^{-1}$ (e.g., 20.34, 20.83, or 21.35 $s^{-1}$)). The zinc oxide may be dispersed under vacuum (about 0.2-0.6 bar (e.g., 0.3, 0.4, or 0.5 bar) below atmospheric pressure) while mixing (e.g., with the central mixer at about 0.65-0.78 $s^{-1}$ (e.g., 0.67, 0.72, or 0.75 $s^{-1}$), the anchor mixer at about 0.40-0.47 $s^{-1}$ (e.g., 0.42, 0.43, or 0.46 $s^{-1}$), and the rotor stator at about 25.00-26.00 $s^{-1}$ (e.g., 25.31, 25.52, or 25.65 $s^{-1}$)) for about 275-300 minutes (e.g., 284, 290, or 292 minutes). The components can then be cooled under vacuum (e.g., at about 0.2-0.6 bar (e.g., 0.3, 0.4, or 0.5 bar) below atmospheric pressure) to about 69-75° C. (e.g., 69° C., 70° C., or 72° C.) with mixing (e.g., with the central mixer at about 0.40-0.47 $s^{-1}$ (e.g., 0.42, 0.43, or 0.46 $s^{-1}$), the anchor mixer at about 0.23-0.27 $s^{-1}$ (e.g., 0.23, 0.25, or 0.27 $s^{-1}$), and the rotor stator at about 25.00-26.00 $s^{-1}$ (e.g., 25.31, 25.52, or 25.65 $s^{-1}$)). Tocopherol (vitamin E, 0.2 wt %) may be added while maintaining the same mixing rates and dispersed into the mix under vacuum (e.g., at about 0.2-0.6 bar (e.g., 0.3, 0.4, or 0.5 bar) below atmospheric pressure) with mixing (e.g., with the central mixer at about 0.65-0.78 $s^{-1}$ (e.g., 0.67, 0.72, or 0.75 $s^{-1}$), the anchor mixer at about 0.40-0.47 $s^{-1}$ (e.g., 0.42, 0.43, or 0.46 $s^{-1}$), and the rotor stator at about 25.00-26.00 $s^{-1}$ (e.g., 25.31, 25.52, or 25.65 $s^{-1}$)) for about 500-600 minutes (e.g., 543, 554, or 570 minutes). The rotor stator may be turned off, and the composition may be held at about 69-75° C. (e.g., 69° C., 70° C., or 72° C.) with the central mixer at about 0.65-0.78 $s^{-1}$ (e.g., 0.67, 0.72, or 0.75 $s^{-1}$) and the anchor mixer at about 0.40-0.47 $s^{-1}$ (e.g., 0.42, 0.43, or 0.46 $s^{-1}$) overnight. The components may be cooled to about 62-68° C. (e.g., 66° C., 67° C., or 68° C.) with mixing (e.g., the central mixer at about 0.65-0.78 $s^{-1}$ (e.g., 0.67, 0.72, or 0.75 $s^{-1}$) and the anchor mixer at about 0.40-0.47 $s^{-1}$ (e.g., 0.42, 0.43, or 0.46 $s^{-1}$)), and then may be further cooled to about 51-61° C. (e.g., 54° C., 56° C., or 57° C.) with mixing (e.g., the central mixer at about 0.40-0.47 $s^{-1}$ (e.g., 0.42, 0.43, or 0.46 $s^{-1}$) and the anchor mixer at about 0.23-0.27 $s^{-1}$ (e.g., 0.23, 0.25, or 0.27 $s^{-1}$)). The components may be transferred from the main vessel to a side vessel for filling to mix and recirculate the composition while maintaining the last temperature of the main vessel (about 51-61° C. (e.g., 54° C., 56° C., or 57° C.) for the formulation F34) while mixing at about 0.06-0.08 $s^{-1}$ (e.g., 0.06, 0.07, or 0.08 $s^{-1}$). The composition may be placed into a hopper for filling where the hopper may be mixed constantly until all of the product is transferred to containers.

Method for Forming the Formulation F26 Composition

A composition corresponding to Formulation F26 was observed to produce an optimal user experience when applied to skin. Formulation F26 can be prepared by a combination of the aforementioned heating, cooling, mixing, holding, and component addition steps. The method of preparation is described as follows.

The oil and wax components may be about 71.25 wt % FCO and about 4.3 wt % SFW, respectively, and may be combined and heated to about 75-85° C. (e.g., 80° C., 82° C., or 83° C.) with mixing (e.g., with the central mixer at about 0.85-1.05 $s^{-1}$ (e.g., 0.93, 0.95, or 0.97 $s^{-1}$) and the anchor mixer at about 0.80-1.00 $s^{-1}$ (e.g., 0.87, 0.90, or 0.93 $s^{-1}$)). Then, zinc oxide (18.75 wt %) may be added while mixing (e.g., with the central mixer at about 0.85-1.05 $s^{-1}$ (e.g., 0.93, 0.95, or 0.97 $s^{-1}$), the anchor mixer at about 0.80-1.00 $s^{-1}$ (e.g., 0.87, 0.90, or 0.93 $s^{-1}$), and the rotor stator at about 9.50-11.50 $s^{-1}$ (e.g., 9.85, 10.47, or 11.03 $s^{-1}$)). The zinc oxide may be dispersed under vacuum (e.g., at about 0.2-0.6 bar (e.g., 0.3, 0.4, or 0.5 bar) below atmospheric pressure) with mixing (e.g., with the central mixer at about 1.50-1.70 $s^{-1}$ (e.g., 1.52, 1.58, or 1.61 $s^{-1}$), the anchor mixer at about 1.50-1.60 $s^{-1}$ (e.g., 1.50, 1.51, or 1.54 $s^{-1}$), and the rotor stator at about 12.00-13.50 $s^{-1}$ (e.g., 12.57, 12.83, or 13.06 $s^{-1}$)) for about 160-190 minutes (e.g., 165, 174, or 189 minutes). The components can then be cooled under vacuum (e.g., at about 0.2-0.6 bar (e.g., 0.3, 0.4, or 0.5 bar) below atmospheric pressure) to about 69-75° C. (e.g., 69° C., 70° C., or 72° C.) with mixing (e.g., with the central mixer at about 0.85-1.05 $s^{-1}$ (e.g., 0.93, 0.95, or 0.97 $s^{-1}$), the anchor mixer at about 0.80-1.00 $s^{-1}$ (e.g., 0.87, 0.90, or 0.93 $s^{-1}$), and the rotor stator at about 12.00-13.50 $s^{-1}$ (e.g., 12.57, 12.83, or 13.06 $s^{-1}$)). Tocopherol (vitamin E, 0.2 wt %), seaweed extract (2.0 wt %), and babassu starch (3.5 wt %) may be added while maintaining the same mixing rates and dispersed into the mix under vacuum (e.g., at about 0.2-0.6 bar (e.g., 0.3, 0.4, or 0.5 bar) below atmospheric pressure) with mixing (e.g., with the central mixer at about 1.50-1.70 $s^{-1}$ (e.g., 1.52, 1.58, or 1.61 $s^{-1}$), the anchor mixer at about 1.50-1.60 $s^{-1}$ (e.g., 1.50, 1.51, or 1.54 $s^{-1}$), and the rotor stator at about 12.00-13.50 $s^{-1}$ (e.g., 12.57, 12.83, or 13.06 $s^{-1}$)) for about 300-360 minutes (e.g., 305, 332, or 345 minutes). The rotor stator may be turned off, and the composition may be held at about 69-75° C. (e.g., 69° C., 70° C., or 72° C.) with the central mixer at about 1.50-1.70 $s^{-1}$ (e.g., 1.52, 1.58, or 1.61 $s^{-1}$) and the anchor mixer at about 1.40-1.60 $s^{-1}$ (e.g., 1.43, 1.52, or about 1.50-1.70 $s^{-1}$ (e.g., 1.52, 1.58, or 1.61 $s^{-1}$)) overnight. The components may be cooled to about 62-68° C. (e.g., 66° C., 67° C., or 68° C.) with the central mixer at about 1.50-1.70 $s^{-1}$ (e.g., 1.52, 1.58, or 1.61 $s^{-1}$) and the anchor mixer at about 1.50-1.60 $s^{-1}$ (e.g., 1.50, 1.51, or 1.54 $s^{-1}$), then may be further cooled to about 51-61° C. (e.g., 54° C., 56° C., or 57° C.) for the formulation F26 with mixing (e.g., with the central mixer at about 0.85-1.00 $s^{-1}$ (e.g., 0.85, 0.92, or 0.93 $s^{-1}$) and the anchor mixer at about 0.80-1.00 $s^{-1}$ (e.g., 0.87, 0.90, or 0.93 $s^{-1}$)). The components may be transferred from the main vessel to a side vessel for filling to mix and recirculate the composition while maintaining the last temperature of the main vessel (about 51-61° C. (e.g., 54° C., 56° C., or 58° C.) for the formulation F26) while mixing at about 0.14-0.16 $s^{-1}$ (e.g., 0.14, 0.15, or 0.16 $s^{-1}$) until all the product is transferred. while mixing at about 0.14-0.16 $s^{-1}$ (e.g., 0.14, 0.15, or 0.16 $s^{-1}$). The composition may be placed into a hopper for filling where the hopper may be mixed constantly for the formulation F26 until all of the product is transferred to containers.

Assays for Testing Properties of a Sunscreen Formulation of the Disclosure

Oscillatory Rheology Analysis

Assays can be performed to assess or measure the properties of a composition of the disclosure (e.g., a sunscreen formulation). For example, assays can be performed to measure an oscillatory rheological property of a composition. Oscillatory rheological properties may include, e.g., elastic modulus, viscous modulus, complex viscosity, yield strain, or crossover strain.

An assay is provided for determining the oscillatory rheology of the compositions described herein. An oscillatory logarithmic strain sweep test may be performed in a rheometer (Anton Paar) from 0.001 to 100% strain within the linear viscoelastic frequency region (0.5 Hz). In this test the elastic modulus (G') and the viscous modulus (G") can be measured. From the results, the complex viscosity ($\eta^*$ at 0.01%), the yield strain (inflexion where G' and G" starts to decrease), and the G' and G" crossover strains can be calculated. The rheological assay is able to measure the resistance of the composition to deformation to measure the hardness or softness of the material. The complex viscosity is a measurement of the viscoelasticity of the material measured as a resistance to deformation considering both the solid like (G') and the liquid like components (G"). Because G' governs the beginning of the strain sweep in oleogels, the viscoelasticity values (complex viscosity) within this region can be referred to as an overall hardness.

Texture Analysis

Assays can be performed to assess or measure the texture of a composition of the disclosure (e.g., a sunscreen formulation). Properties of texture may include firmness, tackiness, and stickiness.

An assay is provided for determining the texture of the compositions described herein. The texture analysis can be performed with a texture analyzer TA.XTplus using a glass cone as a probe. The probe may be pushed into the sample at a speed of 2 mm/s until reaching 10 mm of penetration. Afterwards, the probe may be pulled up at the same speed. Two replicates of each sample can be measured, and the calculated properties are: firmness, tackiness, and stickiness.

Association of the Mechanical Properties with Skin Feel

A composition of the disclosure (e.g., a sunscreen formulation) can be assessed for a mechanical property, such as its skin feel. Skin feel-associated mechanical properties may include degree of hardness, degree of stiffness, sampling difficulty, resistance to oil release, and level of spreadability.

An assay is provided for determining the skin feel-associated mechanical properties of the compositions described herein. The mechanical properties measured can be associated with the skin feel. The associations for the sunscreens measured (also quantified in Table Ill) are classified as:

a) Degree of Hardness. The resistance to deformation will have an effect on the texture related to hardness or softness of the material. The complex viscosity in oleogels is used to describe the strength of the gel network and immobilization of the oil phase, therefore the higher the strength the harder the material will feel. The complex viscosity is a measurement of the viscoelasticity of the material measured as a resistance to deformation considering both the solid like (G') and the liquid like components (G"). Because G' governs the beginning of the strain sweep in oleogels, the viscoelasticity values (complex viscosity) within this region can be referred to as an overall hardness.

b) Degree of Stiffness. Stiffness is the inability to move (or penetrate) the composition easily, therefore the firmness obtained from the texture analysis can be used to describe it. As a quantifiable mechanical property, stiffness is measured as the amount of force required to penetrate the sample. Stiffness was measured as the maximum force required to penetrate 10 mm of the sample.

c) Sampling difficulty. The yield stress obtained with the strain sweep can be related to the first stress that needs to be applied to start spreading the product. If a higher force needs to be applied, then the difficulty increases.

d) Resistance to oil release. The crossover strain, also known as the flowing point, is where the material deforms plastically, meaning that the integrity of the structure is compromised. At this point, the tridimensional crystal structure is no longer capable of holding the liquid oil phase, and the composition starts to flow. Therefore, the crossover strain describes the amount of force or stress necessary to break the integrity of the structure and therefore release the oil from the gel network and as a result this is the moment when an oily feeling will be perceived. Therefore, the lower the force required to release the oil the sooner the oil sensation will be apparent and remain until the sunscreen is rubbed in completely. On the other hand, if the force required is too high the extent of the rubbing stage will start to become a challenge. Therefore, a balance between the high or low limits will improve the user experience where the resistance to release the oil should be long enough to last for most of the rubbing period and then release the oil where it is already in a thin layer improving the oil adsorption (e.g., reducing the oily feel).

e) Level of Spreadability. The degree of tackiness will influence the amount of grip necessary to continue to spread throughout the skin while the degree of stickiness will feel as a dragging feel that will remain until all the product has been spread out. If the spreadability level is high the user experience becomes very difficult and the stickiness feeling can linger after full application of the product. By sensation, spreadability is the level of grip, drag and after-feel. For the determination of tackiness and stickiness, the results depend on the degree of cohesive and adhesive forces of the sample. Tackiness is generally related more to the degree of cohesive forces (Noren et al., *Trends in Food Science & Technology*, 2019, ISSN 0924-2244.), that is the molecular forces that keep the material together (product to product bonds). A tacky material requires large forces to separate from the surface. During the texture analysis, the amount of force necessary to pull the probe from the sample is when the cohesive forces come to a failure and therefore it is related to the degree of tackiness. Stickiness can be defined as the ability of a material to adhere to a surface where the extent of adhesive forces plays a greater role here (Noren et al., *Trends in Food Science & Technology*, 2019, ISSN 0924-2244.). During the texture analysis, when the probe is being pulled from the product the amount of force and time required to go back to the baseline (0 gf) is related to how much the product sticks to the probe.

TABLE III

Categories of the associations of mechanical properties with skin feel.

| Category | Low/Easy | Medium/Moderate | High/Difficult |
| --- | --- | --- | --- |
| Degree of Hardness | $\eta^* <15000$ (Pa · s) | $15000 < \eta^* < 40000$ (Pa · s) | $\eta^* >40000$ (Pa · s) |
| Degree of Stiffness | Firmness <220 (gf) | $220 <$ Firmness $< 340$ (gf) | Firmness >340 (gf) |
| Sampling Difficulty | Yield strain <0.025 (%) | $0.03 <$ Yield strain $< 0.04$ (%) | Yield strain >0.04 (%) |
| Resistance to oil release | Crossover strain <8 (%) | $8 <$ Crossover strain $< 25$ (%) | Crossover strain >25 (%) |
| Level of spreadability | Tackiness <100 (gf) | $100 <$ Tackiness $< 200$ (gf) | Tackiness >200 (gf) |
| | Stickiness <2000 (gf · s) | $2000 <$ Stickiness $< 4000$ (gf · s) | Stickiness >4000 (gf · s) |

Methods of Using the Sunscreen Formulation

A sunscreen formulation as described herein can be applied to the skin in order to reduce the risk of sun damage. The sunscreen may be applied to the skin 15 minutes prior to exposure of the skin to sunlight. Roughly one ounce of sunscreen may be used to cover the body. The sunscreen may be applied to all skin not covered by clothing, including the neck, face, ears, tops of the feet, and legs. The sunscreen may be reapplied every forty minutes or immediately after swimming or sweating in order to provide sun protection when outdoors. The sunscreen should be applied such that there is 2 mg/cm$^2$ on the skin to provide adequate protection from the sun using an SPF30 sunscreen as determined by FDA testing for SPF30 sunscreen.

The following examples are intended to illustrate, rather than limit, the invention.

EXAMPLES

Example 1—Selection of Oil for Gel Based on Texture, Surface Area Coverage, and Absorption Time on Skin Different oils were screened for inclusion into the sunscreen composition. Candidate oils were identified (FIG. 1) and tested to determine the most satisfactory user experience upon application on skin. The oils' residual textures upon application, surface area coverage, and absorption time on skin were measured and compared. Oils with lighter residual texture, high surface area coverage, and low absorption time through the skin were determined to provide the most satisfactory experience and were selected as candidates for the final composition.

Oil dryness was tested using a visual and tactile assessment on skin. A drop of oil was applied on clean dry skin and rubbed evenly, and a score between 1 and 4 was assigned depending on how heavy the oil felt on the skin and how difficult residual oil was to remove from the skin. A score of 1 was assigned to an oil if the skin experienced a non-oily, light feeling accompanied by almost no visual residue once evenly rubbed onto the skin. A score of 4 was assigned to an oil if the skin experienced a heavy oily feeling and was very difficult to remove once evenly rubbed onto the skin. The oils were binned into the following scores: SFO, CAO, and GSO received a 4; RO and LSO received a 3; FCO, JJO, and APO received a 2; and SEO, BAO, ABO, and HEMP received a 1.

Oil surface area coverage was tested by placing a drop of oil on a sheet of paper and measuring the diameter of the oil stain after 5 minutes. The experiment was repeated thrice for each oil. The oil stains were measured to have diameters as shown in FIG. 1. The oils were scored between 1 and 3 based on increasing stain diameters, leading to the following scores: SFO, CAO, BAO, GSO, RO, HEO, ABO, and APO received a 3; LSO received a 2; and SEO, FCO, and JJO received a 1.

Oil absorption was tested by measuring the length of time it took for a drop of oil to be absorbed into the skin without any motion or rubbing, such that the initially visible layer of liquid defining the oil droplet was no longer observed regardless of the shine. The absorption times were plotted in FIG. 2. The oils were scored between 1 and 5 based on increasing absorption times, leading to the following scores: FCO, JJO, APO, HEO, ABO received a 1; BAO and LSO received a 2; GSO and SEO received a 3; RO received a 4; and SFO and CAO received a 5.

Figure 3:
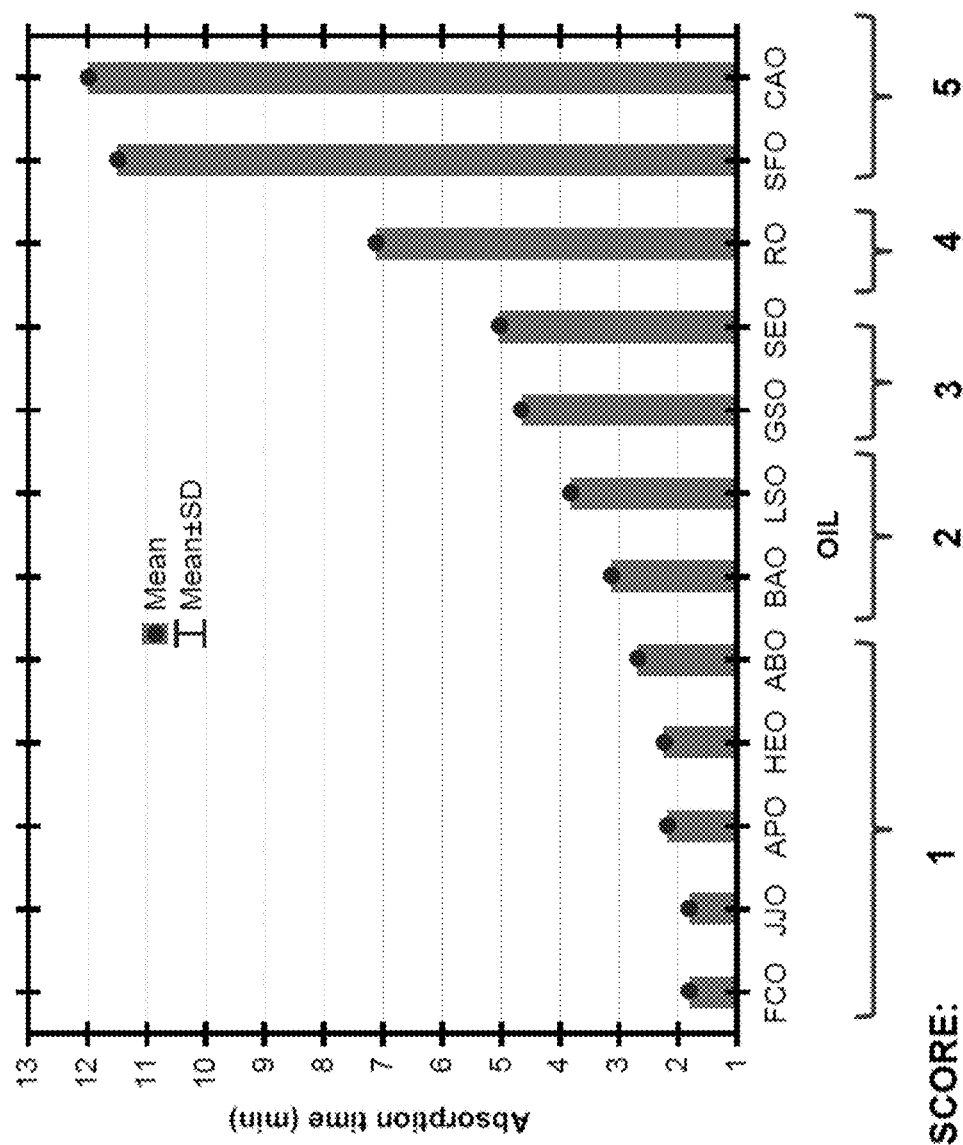
FIG. 3 is a plot showing the absorption time in minutes of each oil on skin and their corresponding numerical score.
Figure 4:
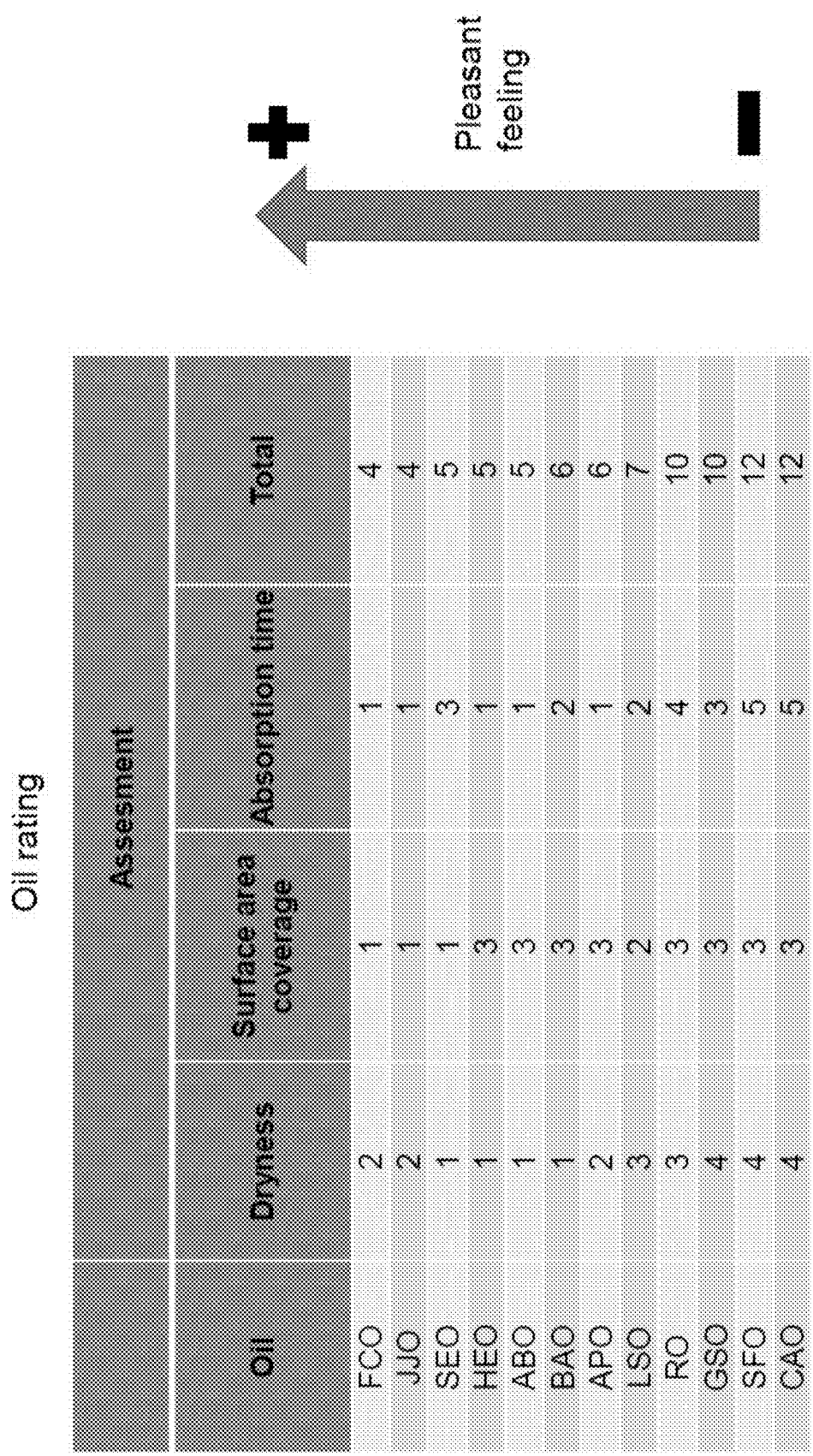
FIG. 4 is a table showing scores for dryness, surface area coverage, and absorption time for each oil along with their total scores.
Figure 5:
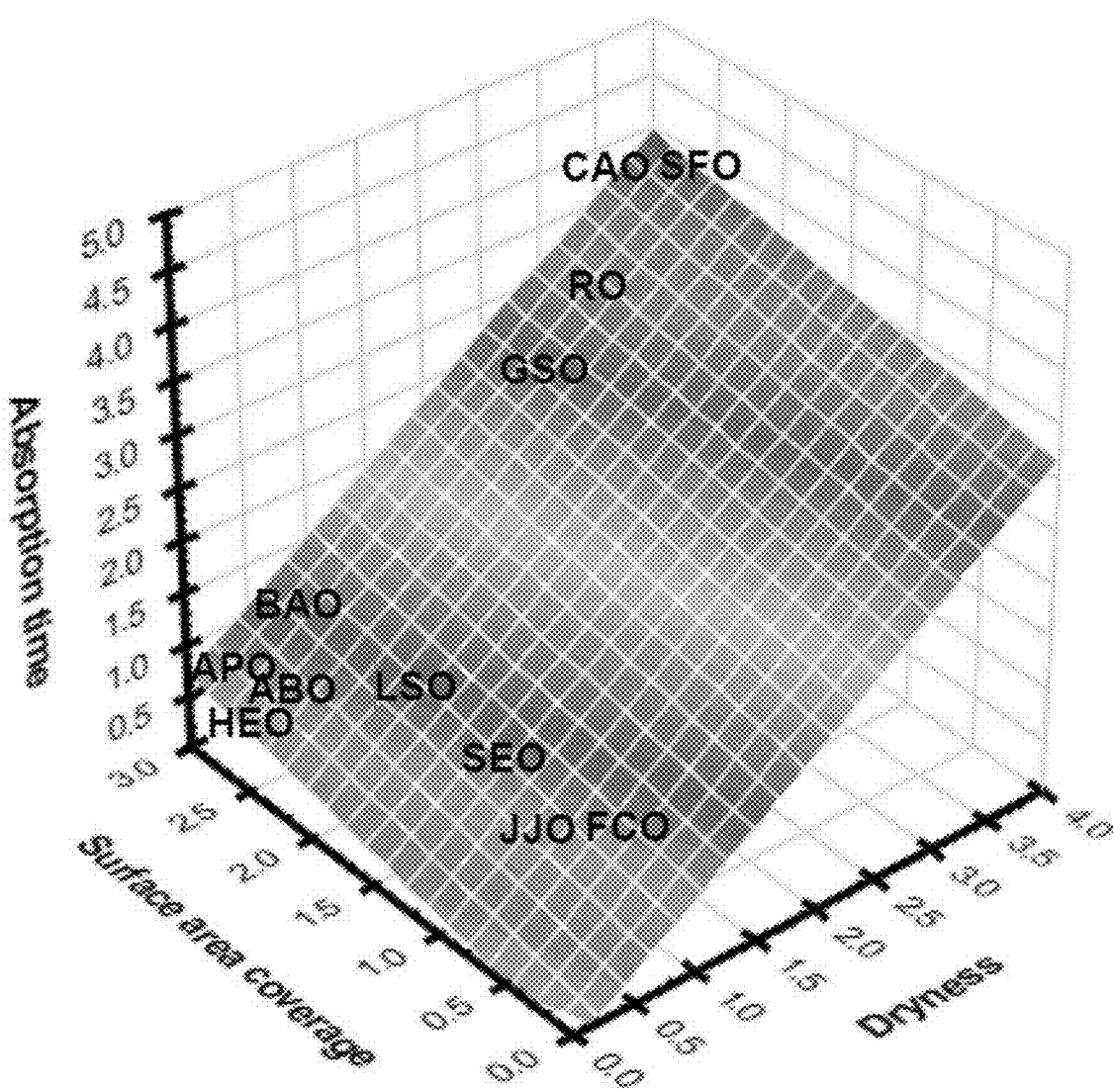
FIG. 5 is a plot showing the scores for dryness, surface area coverage, and absorption time plotted separately along three axis to show how the oils were grouped into three regimes, showing SEO, JJO, and FCO near the lowest dryness, surface area, and absorption time, BAO, APO, ABO, HEO, and LSO with low dryness and absorption time but high surface area coverage, and CAO, SFO, RO, and GSO with high dryness, absorption time, and surface area coverage.
Figure 6:
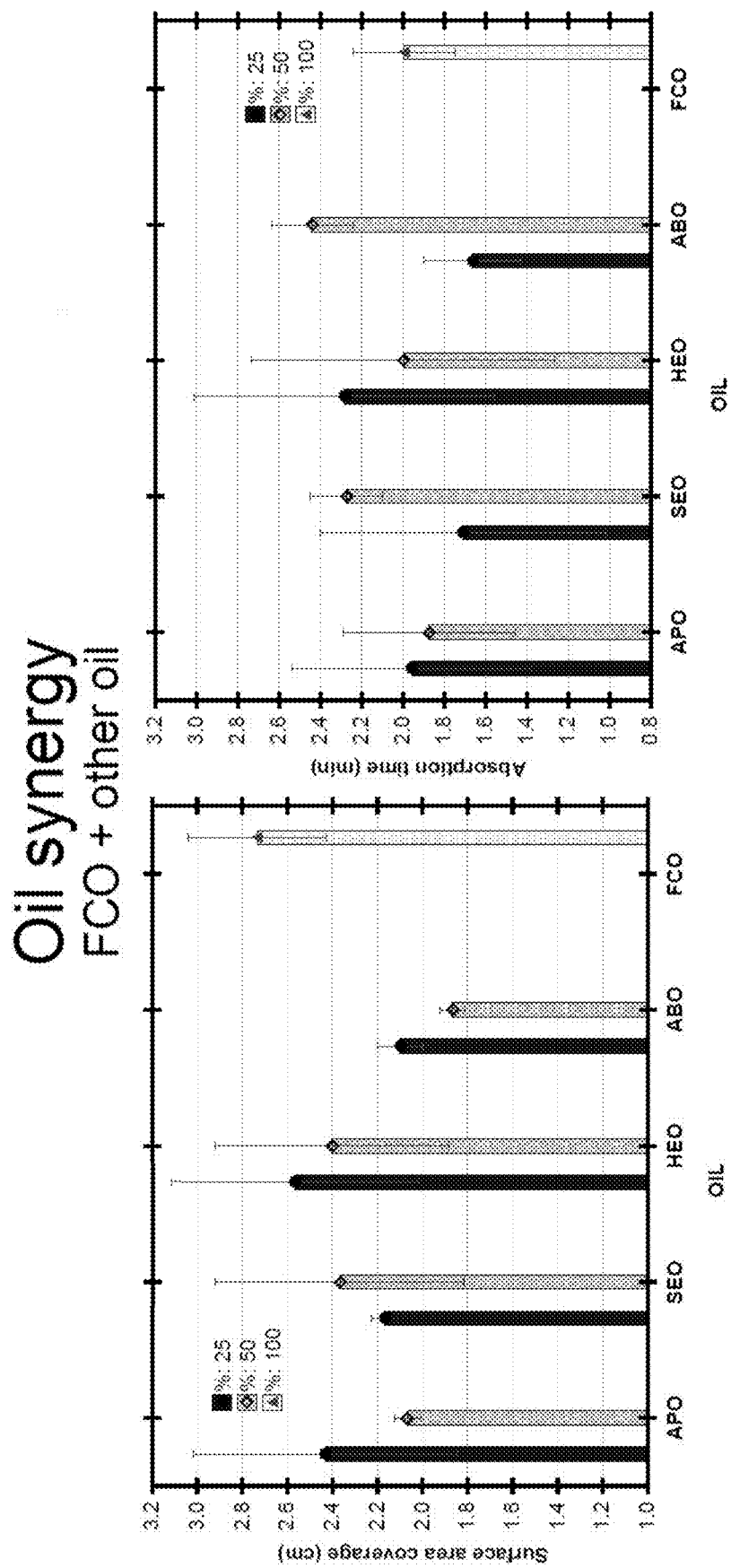
FIG. 6 is a plot showing the surface area coverage and absorption times for FCO compared with oil components comprising 1:1 or 3:1 FCO to APO, SEO, HEO, or HBO, demonstrating that there were few differences between the pure FCO's surface area coverage and absorption time compared with the two oil compositions.

Oils were rated by adding their scores across the three assessments and selecting oils were lower overall scores, as shown in FIG. 3. Based on these results, FCO and JJO were determined to have the most satisfactory tactile experience on skin among the oils tested. The values were plotted on a 3D plot comparing the oils' dryness, surface area coverage, and absorption to show how each oil's physical characteristics contributed to their overall score in FIG. 4. In FIG. 5, it was found that there were three qualitative groups into which the oils could be sorted as a function of overall score, with one group comprising SEO, JJO, and FCO, another group comprising LSO, ABO, APO, HEO, and BAO, and the last group comprising GSO, RO, CAO, and SFO, and few oils represented in between these groups.

Oil synergy was measured by conducting dryness, surface area coverage, and absorption tests using combinations of FCO with ABO, APO, SEO, or HEMP oil in 1:1 and 3:1 ratios, respectively. Statistically significant differences were not observed in the surface area coverage or absorption tests between FCO and combination oils. Oil combinations did not have an observed visible or tactile difference compared with pure FCO as shown in FIG. 5.

Example 2—Combination of Wax or Waxes with FCO to Determine Gelation Concentration, Syneresis, and Thixotropy Upon identification of suitable oils, it was next determined which one, or combination, of the suitable oils and a wax, or waxes, would form a stable gel. To do so, five candidate waxes, CUW, RW, SFW, BW, and CLW, (FIG. 7) were selected and combined with four oils, SFO, GSO, RO, and FCO, to determine the amount of wax, measured as a weight percent of the total composition, that was required to form a gel upon combination with an oil, defined as the critical gelation concentration. The critical gelation concentration was determined by combining a wax with an oil within a sealable vial at a low weight percent, e.g., 1 wt % (w/w), homogenizing the composition through heating and mixing until a solution was obtained, then left to cool at room temperature for two hours. Then the sealed vial was inverted and observed to see if the composition flowed. Flowing compositions indicated an insufficient amount of wax to form a gel, or that the wax weight percentage was below the critical gelation concentration. The test was repeated with incrementally increased wax loadings until the inverted vial test succeeded, at which point the critical gelation concentration was measured to be the wax weight percent utilized to prevent the composition from flowing. The weight percent of wax required to reach the critical gelation concentration for each oil and wax pair was aggregated in FIG. 8. Once a critical gelation concentration was determined for each pairing, gels containing one weight percent more wax than the critical gelation concentration were made and their oil release rates were determined by placing a small amount of each gel on a sheet of paper. The diameter of the oil stain made by the gel was measured after five minutes and after two hours. The rate at which the oil was released from the gel was calculated by comparing the diameters of the oil stains at the two time points, and the oil release rates were plotted in FIG. 9. It was shown in FIG. 9 that compositions containing SFW and SFO or SFW and GSO had the slowest oil release rates while compositions containing RW and FCO or CUW and FCO had the fastest oil release rates.

A thixotropy test was conducted on the gels to determine if the gel recovered into its original gel form (non-flowing material after inverting the vial) after scooping from the bulk or after shearing vigorously for 10 s with a spatula, then waiting for two hours without disturbance. It was found that gels made with CUW, RW, and SFW with any oil either did not recover or only partially recovered upon shearing and waiting, while gels made from CW combined with SFO or GSO and BW combined with GSO, FCO, or RO reformed into gels after shearing and allowing to rest. Furthermore, gels made from CW combined with SFO, GSO, or RO, BW combined with FCO, and SFW combined with FCO or RO formed gels whose scooped samples showed no signs of oil separating out, also known as syneresis. These results are summarized in FIG. 10.

Figure 11:
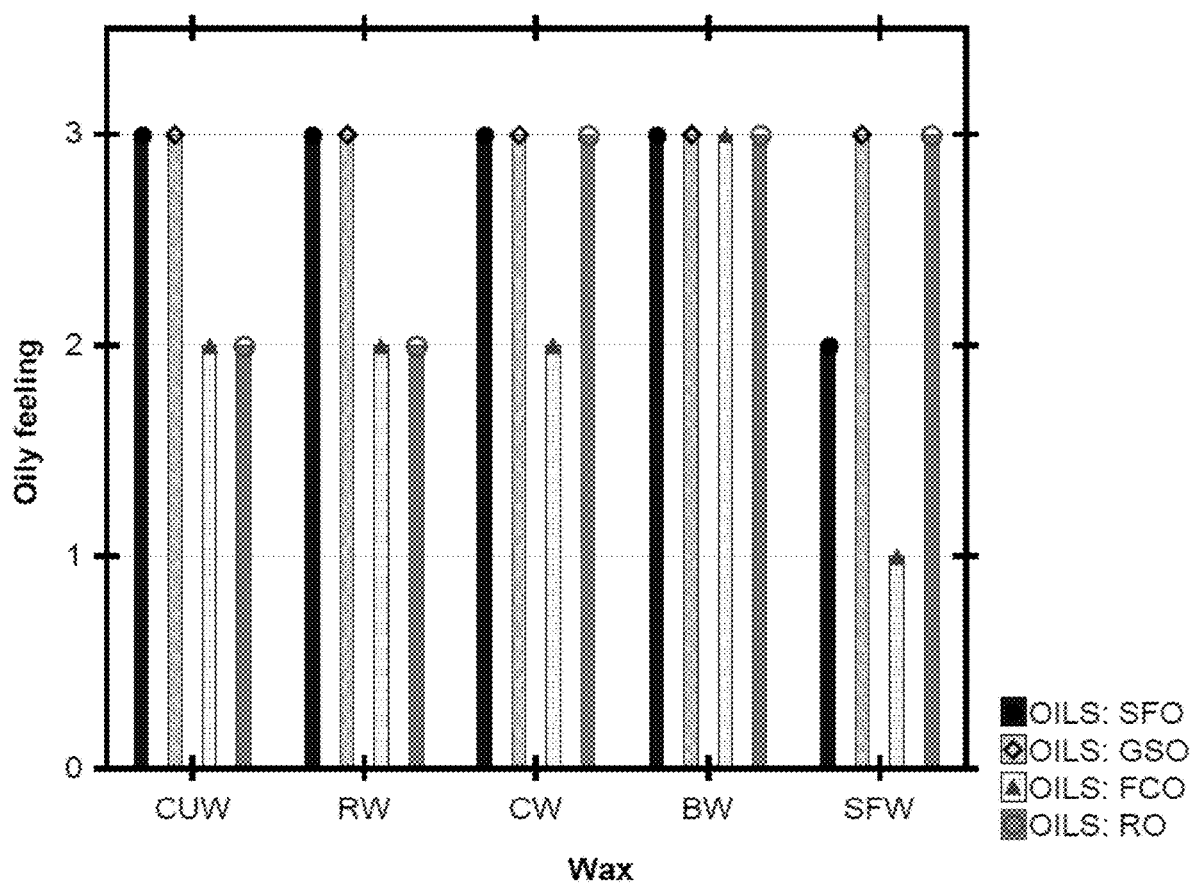
FIG. 11 is a plot showing the results of the skin feel test, where oily feeling gels were scored higher on a 0-3 scale.

Gel skin feel was tested using a visual and tactile assessment on skin as was done to test the oil dryness. It was found that gels made from SFW and FCO produced the best skin feel, as shown in FIG. 11.

Further tests were conducted to determine if combinations of waxes combined with a single oil produced a gel. It was found that combinations of BW and CW produced gels with SFO and FCO as shown in FIG. 12. Further tests revealed that while gelation occurred for HEMP, SEO, APO, FCO, and ABO oils with 1% SFW, gelation only occurred for specific combinations of BW and CW with pairings of the aforementioned oils, as shown in FIG. 13. More specifically, 0.5 wt % BW+0.5 wt % CW only formed gels with APO, FCO, and ABO, 1.0 wt % BW+0.5 wt % CW only formed gels with HEMP, FCO, and ABO, 1.0 wt % BW+1 wt % CW only formed gels with SEO, FCO, and ABO, and 0.5 wt % SFW+0.5 wt % BW did not form gels with any oils.

Example 3—Voluntary Human Sensorial Testing of Ten Sunscreen Formulations and Gel Texture Optimization With oleogel formulas determined, it was necessary to find a sunscreen that provided users with the most satisfactory experience. To do so, ten compositions (e.g., sunscreen formulations; e.g., F1-F10) of interest were produced, based on the prior Examples to determine a suitable oil or combination of oils, oleogels formed from a suitable oil and one or more waxes, and zinc oxide particles, as listed in Table Ill.

Figure 14:
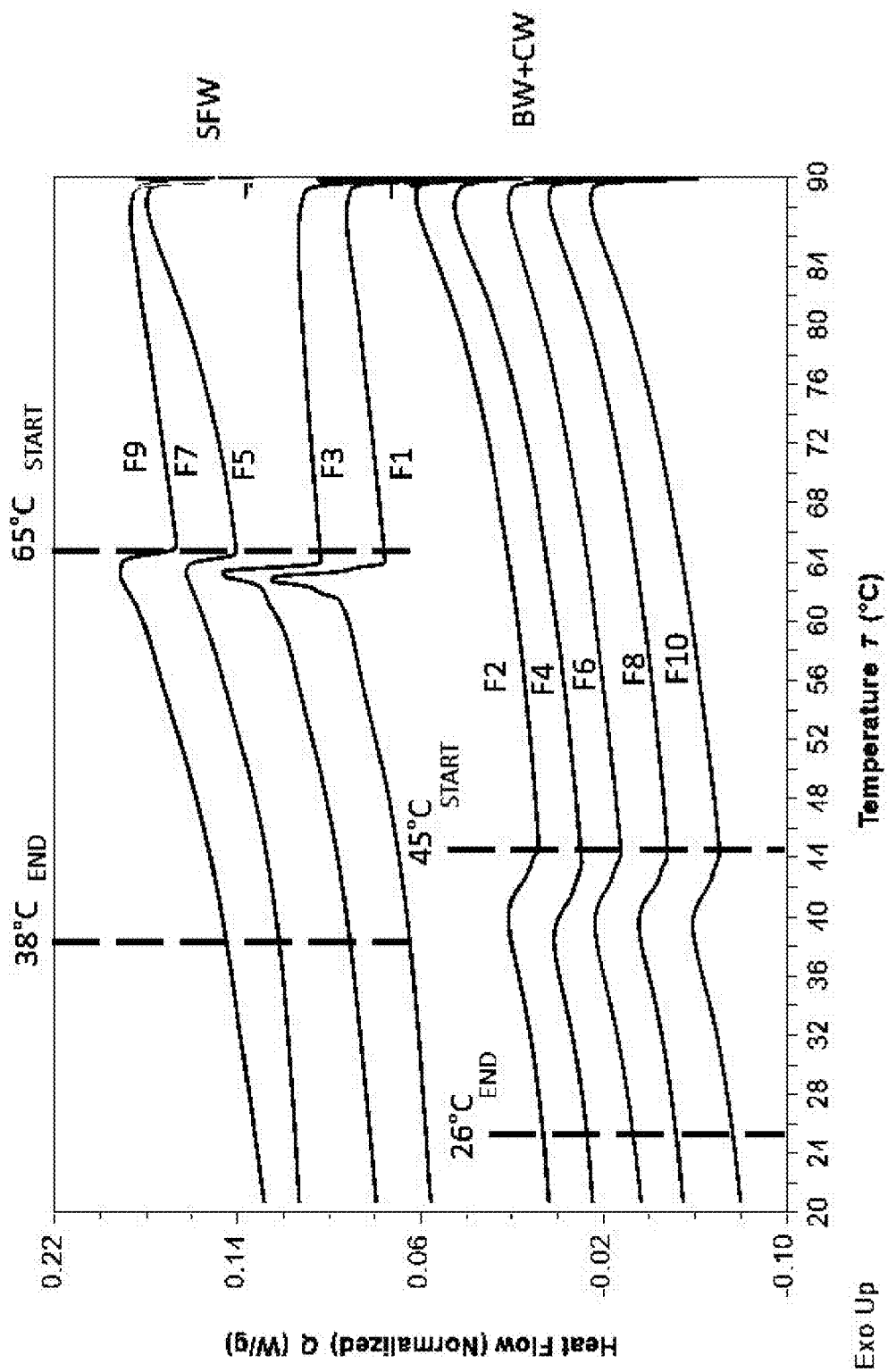
FIG. 14 is a plot showing the crystallization differential scanning calorimetry results for compositions F1-F10 with dashed lines to indicate onset and end temperatures of the liquid to solid phase transition. As shown in the top half of the graph, SFW was cooled from 90° C. to 20° C., and the crystallization began at 65° C. and ended at 38° C. As shown in the bottom half of the graph, the 1:1 BW:CW combination wax was cooled from 90° C. to 20° C., and the crystallization began at 45° C. and ended at 26° C.
Figure 15:
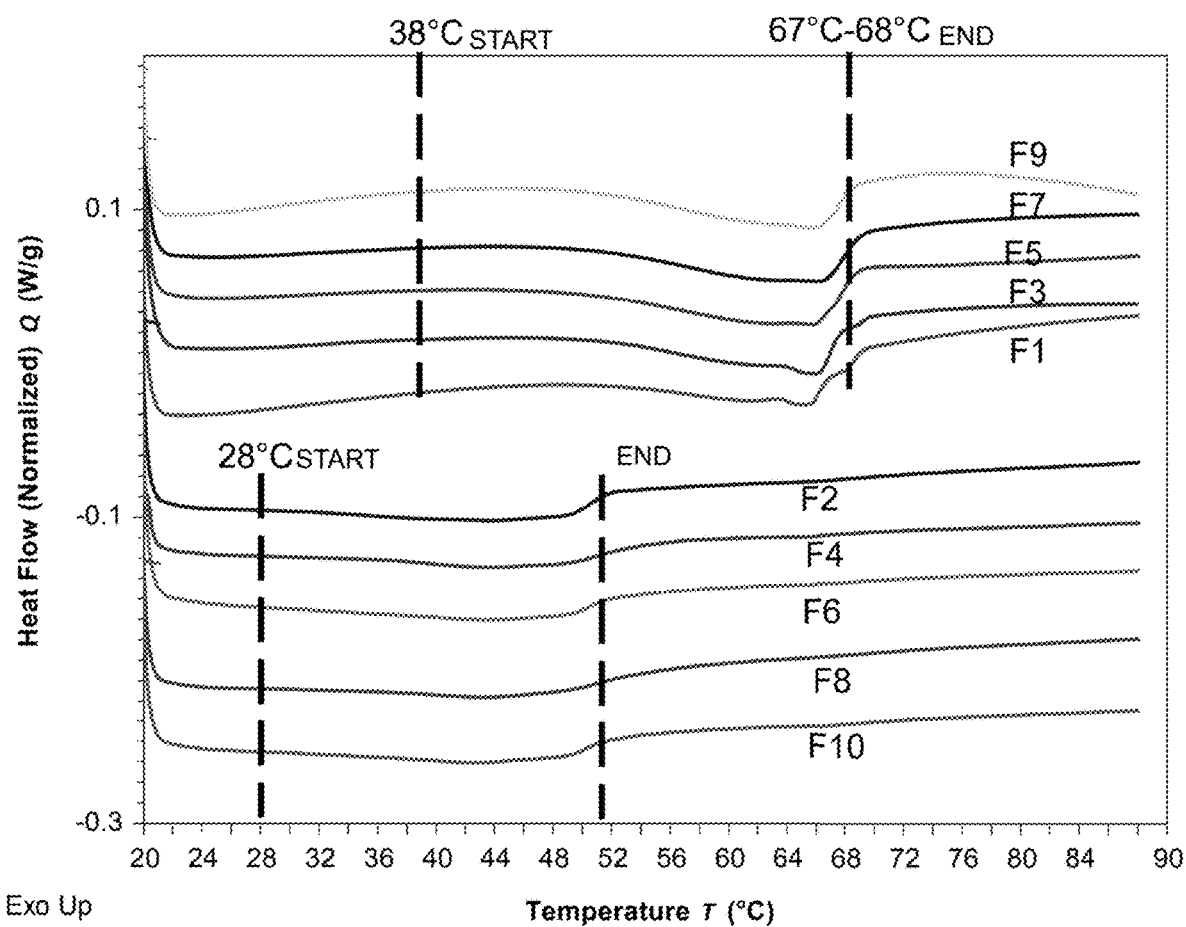
FIG. 15 is a plot showing the melting differential scanning calorimetry results for compositions F1-F10 with dashed lines to indicate start and end temperatures of the solid to liquid phase transition. In the top half of the graph, SFW was heated from 20° C. to 90° C., and the melting begins at 38° C. and ends between 67-68° C. In the bottom half of the graph, the 1:1 BW:CW combination wax was heated from 20° C. to 90° C., and the melting begins at 28° C. and ends at 49° C.
Figure 16:
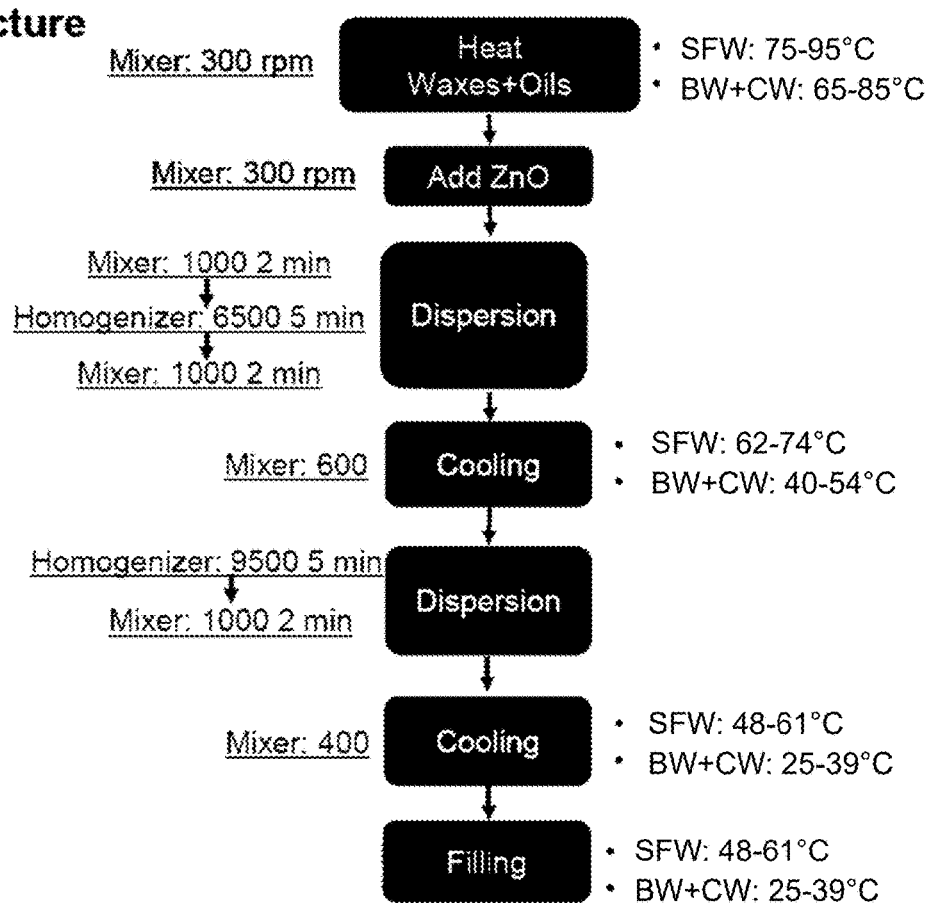
FIG. 16 is a schematic showing a manufacturing process, listing the mixing speed, step duration, and/or composition melting temperature for each process step. First, waxes and oils are heated to form a homogeneous liquid composition and mixed. Next, ZnO particles are added, dispersed, cooled, further dispersed, cooled, then unloaded into a container. The temperatures are different between the SFW and BW+CW compositions, but the mixing speeds and hold times remain the same.

Currently commercialized SPF30 BADGER® (TX, USA) cream was included as formulation F11. Based on measurements of crystallizing and melting temperatures made on the waxes using differential scanning calorimetry as shown in FIGS. 14 and 15, respectively, a manufacturing process was made to combine the oil component, wax component, and zinc oxide particles to form a stable gel. This process is illustrated in FIG. 16.

Figure 21:
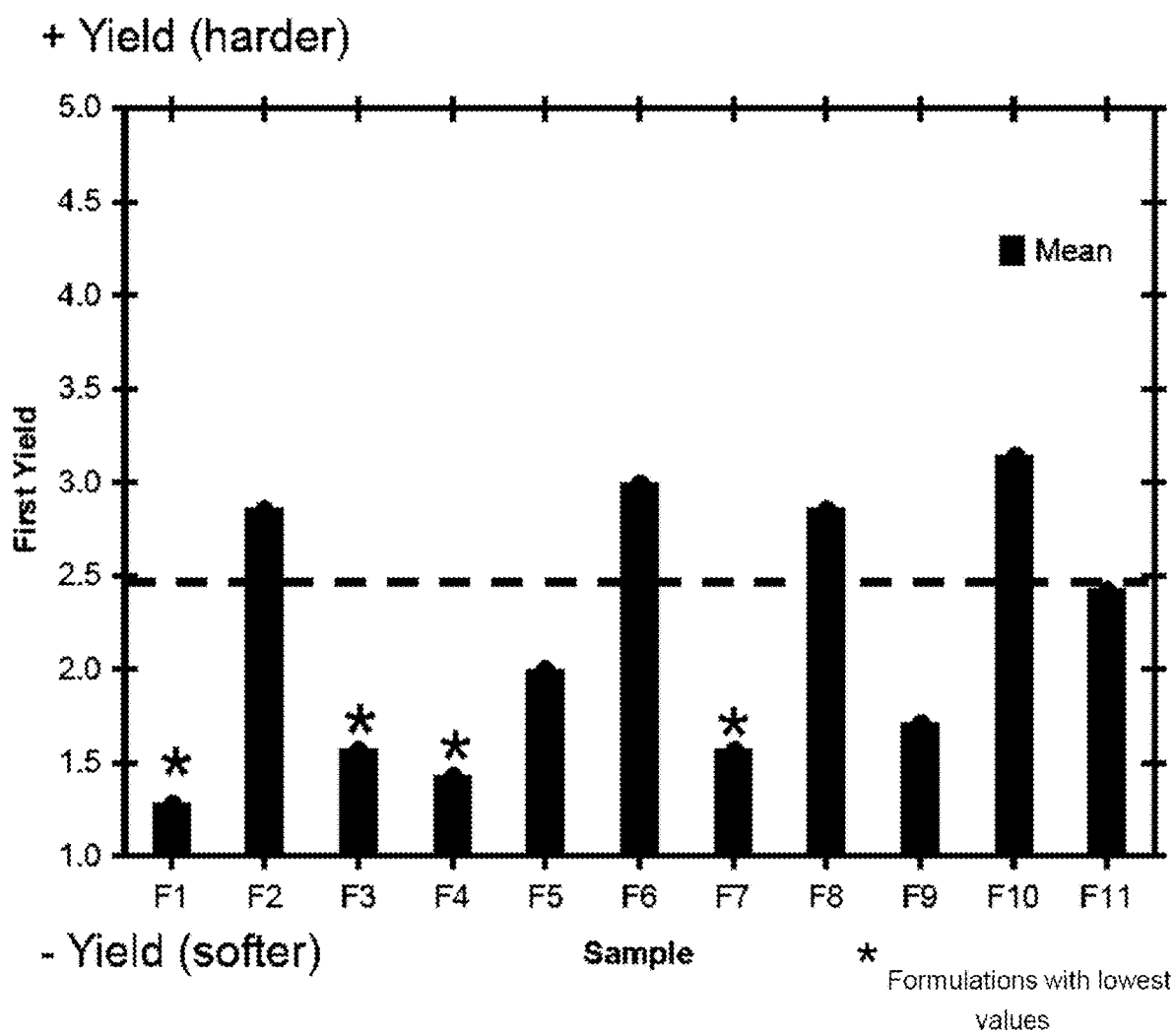
FIG. 21 is a plot showing the results from a sensorial test including nine participants who were asked to rate, between 1 (low) and 5 (high), how much force was necessary to cause compositions F1-F11 to move upon contact.
Figure 22:
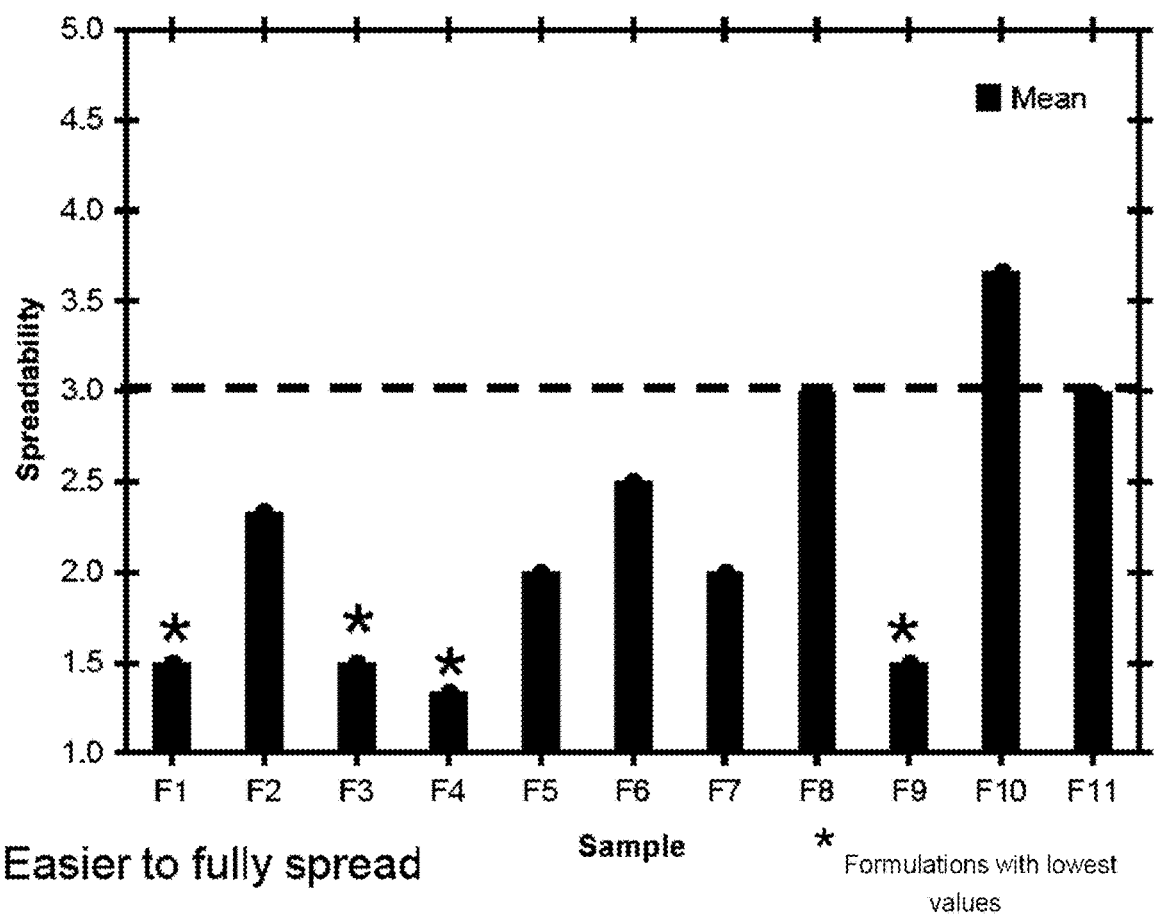
FIG. 22 is a plot showing the results from a sensorial test including nine participants who were asked to rate, subjectively, between 1 (low) and 5 (high), how challenging it was to spread compositions F1-F11 after the first yield.

The compositions, once made, were subjected to a sensorial test including nine participants who were asked to rate, between 1 (low) and 5 (high) how oily the composition felt during application (FIG. 17), how oily the composition felt once fully spread on their skin (FIG. 18), how grainy the composition appeared (FIG. 19), how rough the composition felt on their skin (FIG. 60), how much force was necessary to cause the sunscreen to yield at first contact (FIG. 21) and how challenging it was to spread the composition (FIG. 7). The results were summarized in FIG. 8, wherein it was determined that F1 had the most satisfactory user experience with a sensorial result of 20 and F9 had the second most satisfactory user experience with a sensorial result of 17. Formulations F2, F5, and F6 had the least satisfactory user experience with a sensorial result of 0, and formulations F4 and F6 displayed undesirable syneresis.

As a result of this study, it was determined that a suitable base formula for prototyping was a composition containing 4.30 wt % SFW, 76.75 wt % FCO, 0.20 wt % vitamin E, and 18.75 wt % ZnO, identified as F1, hereafter referred to as the formulation F34.

Figure 9:
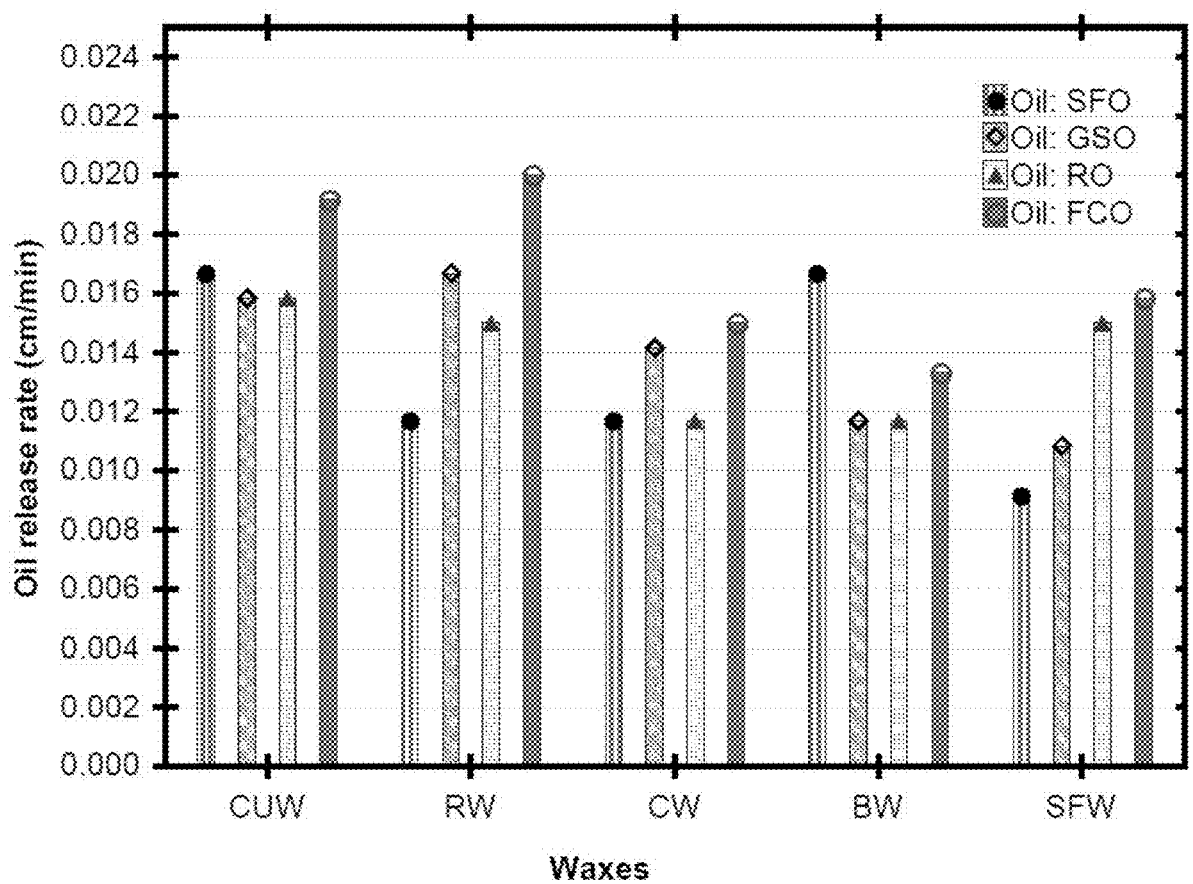
FIG. 9 is a plot showing the oil release rate in centimeters per minute for each gel composition made with one wax and one oil, which was measured by measuring the diameter of the oil from a drop of gel on paper at 5 minutes and 2 hours, subtracting the diameter measured at 2 hours from the diameter measured at 5 minutes, then dividing the difference in centimeters by the time in minutes.
Figure 27:
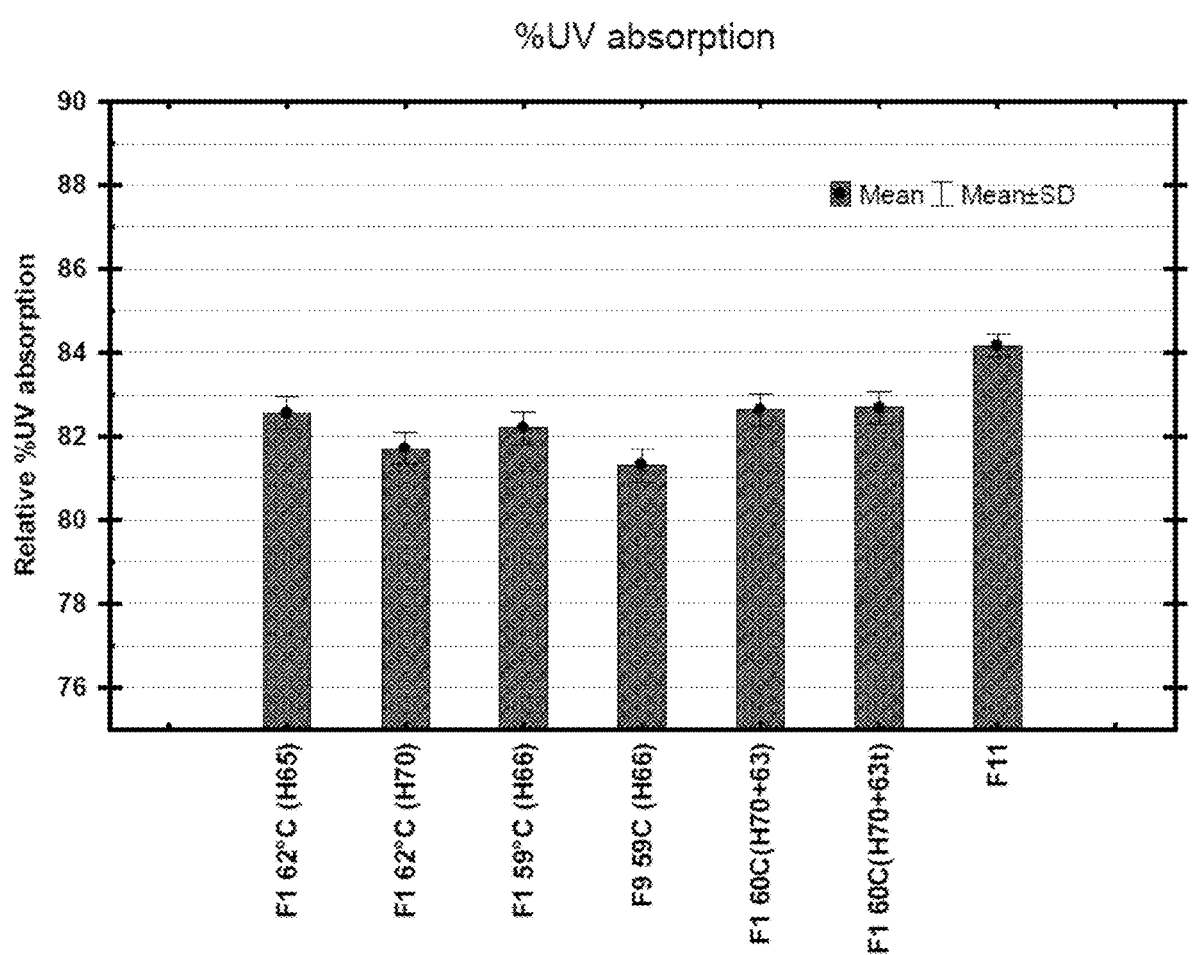
FIG. 27 is a plot showing the relative % UV absorption for various formulations with various processing conditions. The relative % UV absorption did not vary significantly as a function of formulation or processing condition. This result aligned with the relatively unchanged ZnO particle loading wt %, as ZnO was the ingredient primarily responsible for reducing skin damage.
Figure 28:
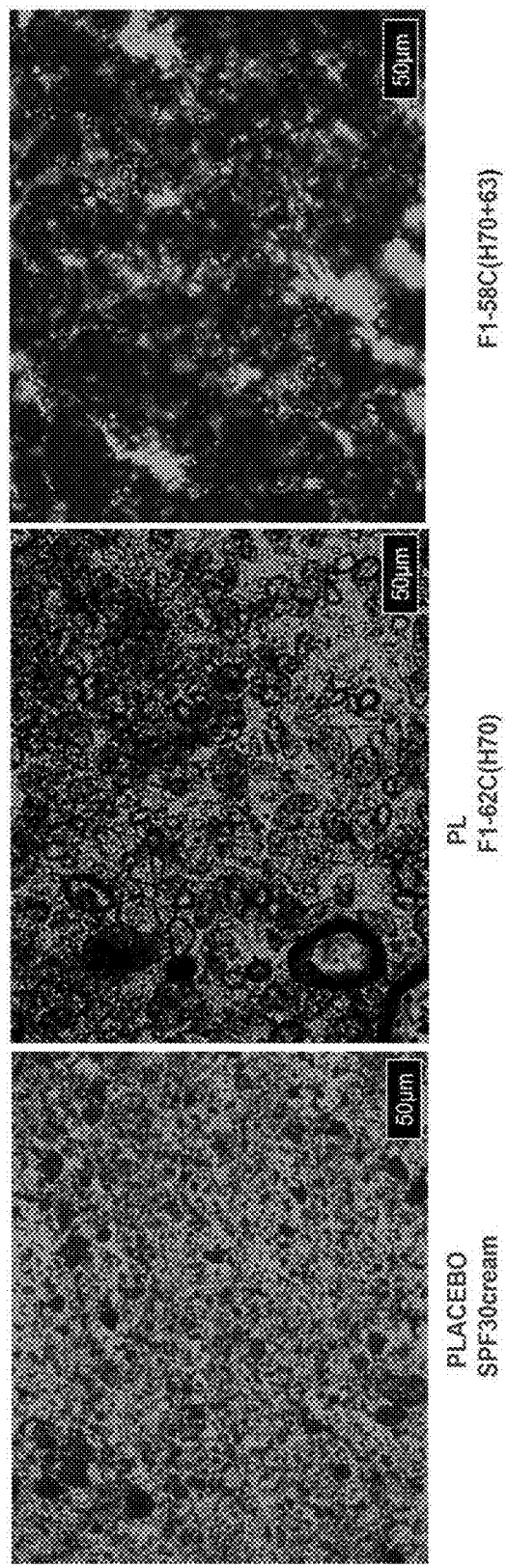
FIG. 28 is a set of images showing polarized micrographs of a placebo BADGER® SPF30 cream (TX, USA) and F1 creams made using different processing conditions. Qualitatively, the polarized micrographs of the three samples were very similar to each other, indicating that similar amounts of light were blocked by all three compositions although some morphological differences are observed from the crystal structures specially between the BADGER® SPF30 cream (TX, USA) and the F1 formulations. A polarizer shows where crystalline material was located in contrast with where noncrystalline, or amorphous material, was located, as the crystalline material should refract and reflect the light while the amorphous material should not. As a result, as the polarizer was turned, the crystalline material should darken and brighten while the amorphous material should stay uniformly transparent. Comparably dark micrographs taken of the three compositions indicated that the three compositions blocked similar amounts of light.
Figure 29:
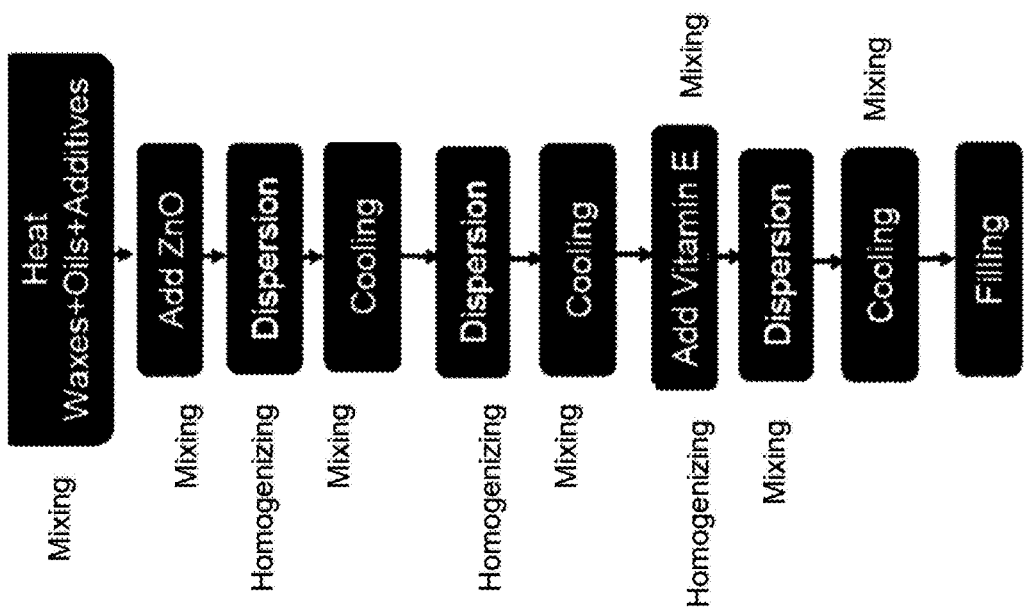
FIG. 29 is a scheme showing a manufacturing process that includes the addition of vitamin E. First, waxes and oils were heated to form a homogeneous liquid composition and mixed. Next, ZnO particles were added, disperse, cooled, further dispersed, and cooled, before vitamin E was added. The composition was mixed to disperse the vitamin E, mixed to disperse further, cooled further, and transferred. The temperatures were different between the SFW and BW+CW compositions, but the mixing speeds and hold times remained the same.
Figure 30:
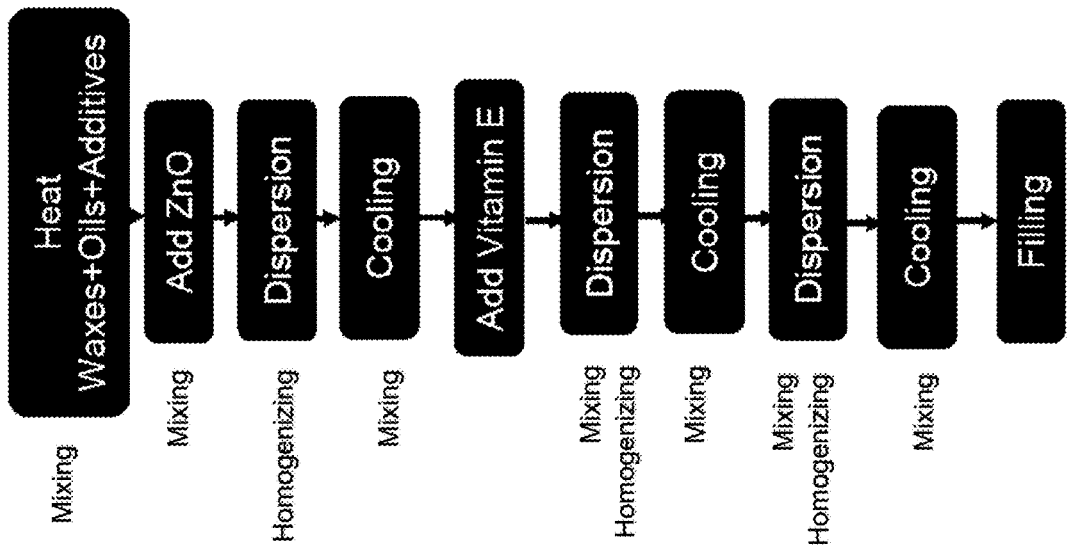
FIG. 30 is a scheme showing a manufacturing process that includes the addition of vitamin E. First, waxes and oils were heated to form a homogeneous liquid composition and mixed. Next, ZnO particles were added, disperse, cooled, further dispersed, and cooled, before vitamin E was added. The composition was mixed to disperse the vitamin E, mixed to disperse further, cooled further, and transferred.
Figure 31:
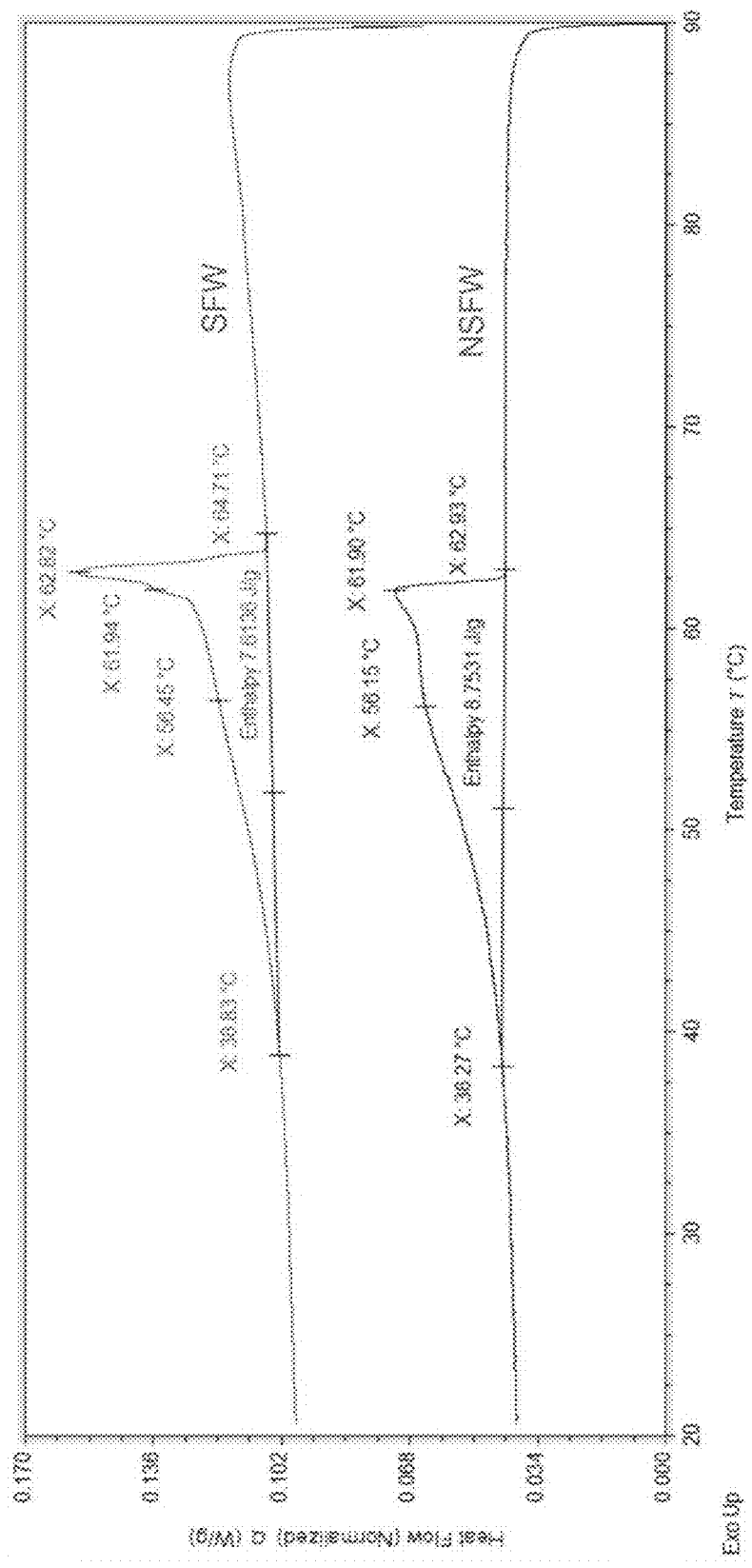
FIG. 31 is a plot showing a high resolution crystallization DSC of F1 with two SFWs from two different providers to determine all intermediate crystallization temperatures between onset of and completion of the crystallization manifold. The new sunflower wax (NSFW) was from a natural source and has measurably different crystallization behavior compared to the previous SFW.
Figure 32:
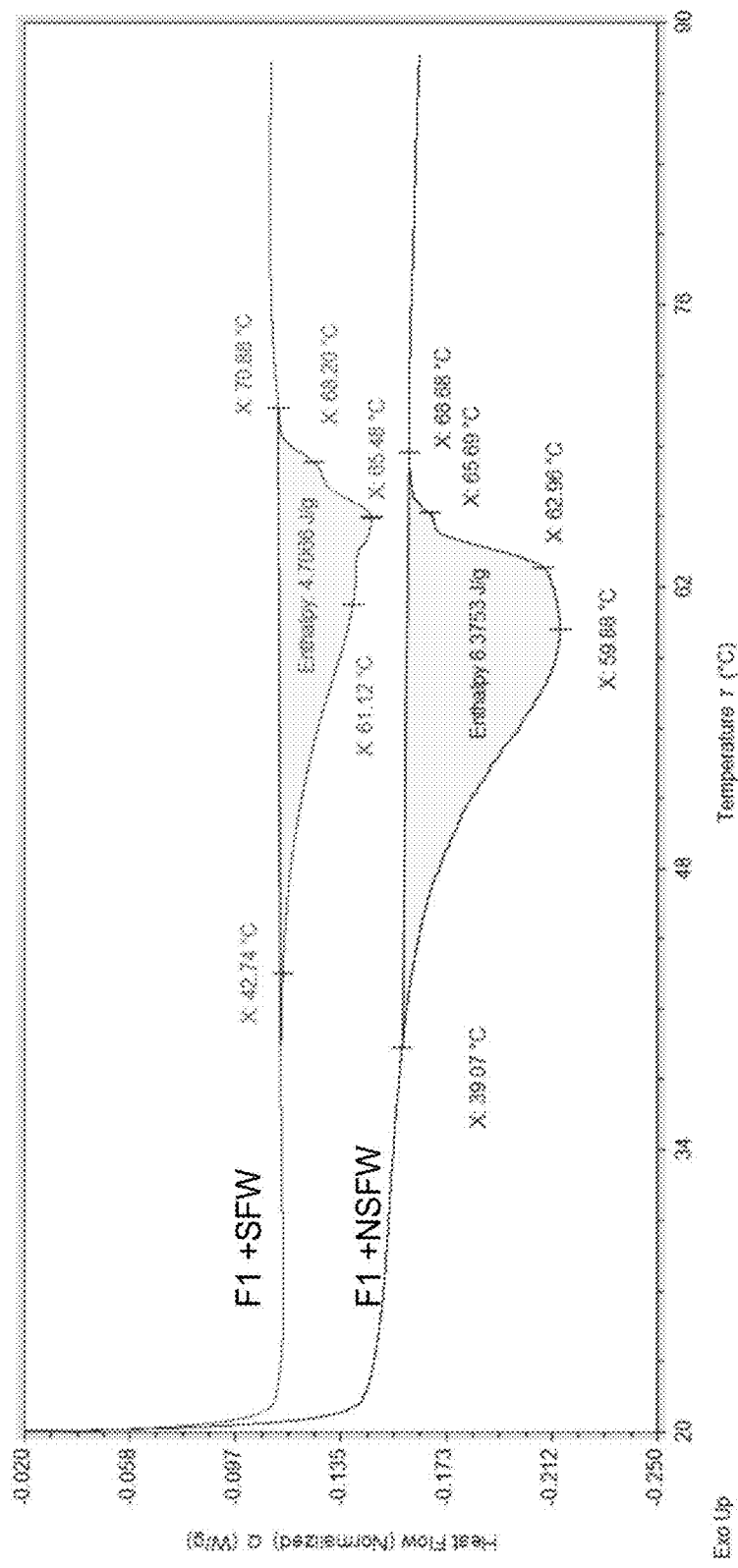
FIG. 32 is a plot showing a high resolution melting DSC of F1 with two SFWs from two different providers to determine all intermediate melting temperatures between the start of and completion of the melting manifold. The new sunflower wax (NSFW) was from a natural source and had measurably different melting behavior compared to the previous SFW.

To ensure proper ZnO dispersion and explore softer and more pleasant tactile experiences upon application on skin, the process by which the formulation F34 was combined was modified as shown in FIG. 9. Changes to the combination process were informed using high resolution DSC scans of the crystallization and melting processes of the formulation F34, shown in FIGS. 10 and 11, respectively, that showed different temperatures at which the composition or constituents melted or crystallized. The relative % UV absorption of the compositions that resulted from the modified processes was measured and plotted in FIG. 27, and polarized photomicrographs were taken to compare compositions with a SPF 30 sunscreen, as shown in FIG. 28. A schematic of the manufacturing processes to produce the optimal texture and experience are illustrated in FIGS. 29 and 12, respectively. A modification was made using a different SFW with different crystallization and melting behavior shown in FIGS. 13, 14, and 15, and the manufacturing process was robust enough to be adjusted to accommodate the physical properties of the changed SFW as illustrated in FIG. 16.

Figure 35:
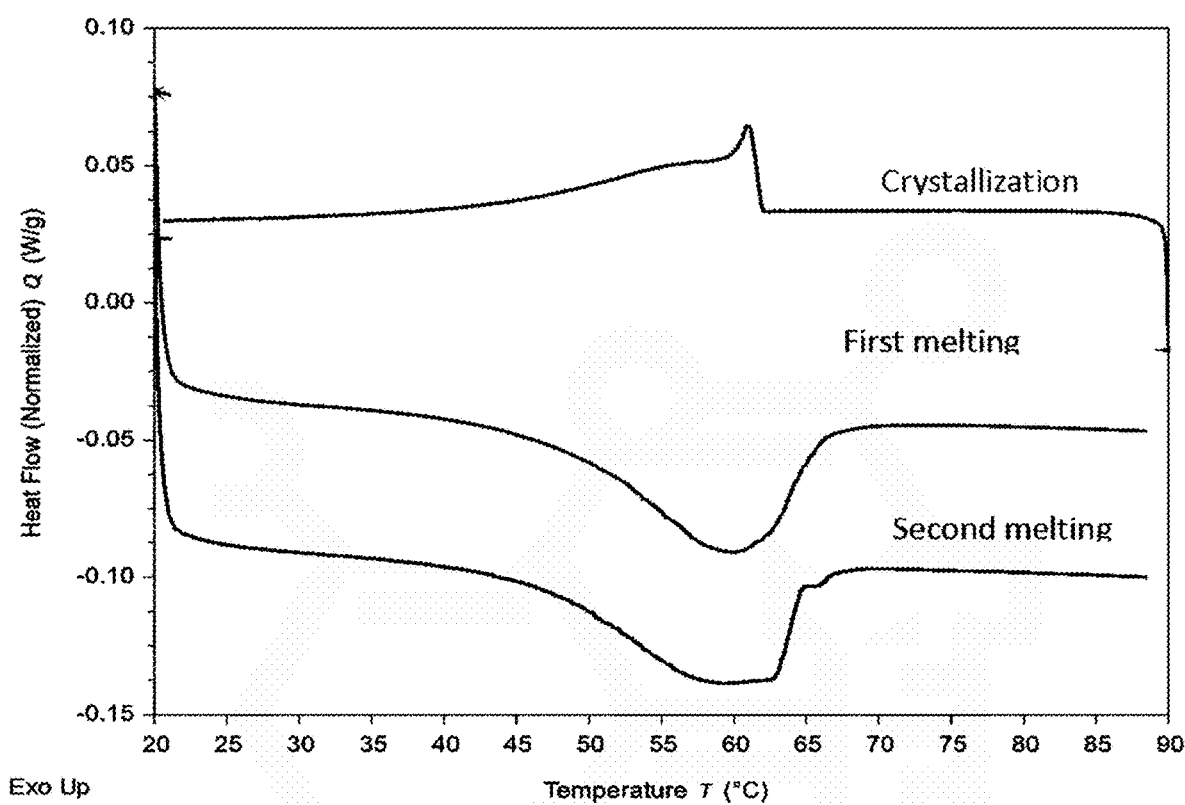
FIG. 35 is a plot showing the thermodynamic properties of the formulation F34. The composition was characterized through differential scanning calorimetry in three different cycles, wherein the heat flow (Q, W/g) in or out of the sample was measured by first melting the composition following the "First melting" trace, crystallizing the composition as shown in the "Crystallization" trace, and remelting the composition as shown in the "Second melting" trace.

An optimal process for producing the formulation F34 was determined in a reactor. The thermodynamic properties of the composition were characterized through differential scanning calorimetry in three different cycles, wherein the heat flow (Q, W/g) in or out of the sample was measured (FIG. 35):
  First melting: Melting from 20° C. to 90° C. at 5° C./min of the product as manufactured.
  Crystallization: Cooling from 90 to 20° C. at 2° C./min.
  Second melting: Melting from 20° C. to 90° C. where the effect of processing is revealed.

Furthermore, mechanical characterization was performed. Oscillatory rheological assays were performed on the batches under three conditions:

Melting. Assay performed while heating from 25° C. to 90° C. at 5° C./min (similar conditions as for the first melting from the thermal characterization).

Crystallization. Assay performed while cooling from 90° C. to 25° C. simulating the shearing conditions that are applied during manufacture without any holding time (e.g., not overnight).

Overnight effect. Assay performed while cooling from 90° C. to 25° C. including a simulated overnight high shear step (10 min at 700 rpm at 70° C.) within the optimal conditions established.

The elastic modulus (G', Pa) and viscous modulus (G", Pa) were measured to determine the hardness of the sample and resistance to flow of the liquid part of the sample, respectively. The measurements were conducted within the linear viscoelastic region (intrinsic properties of the organogel itself independent from the frequency or strain used in the test). During the full characterization G' remained above G" due to the amount of solids of ZnO present, therefore for practical purposes only G' was reported.

Figure 36:
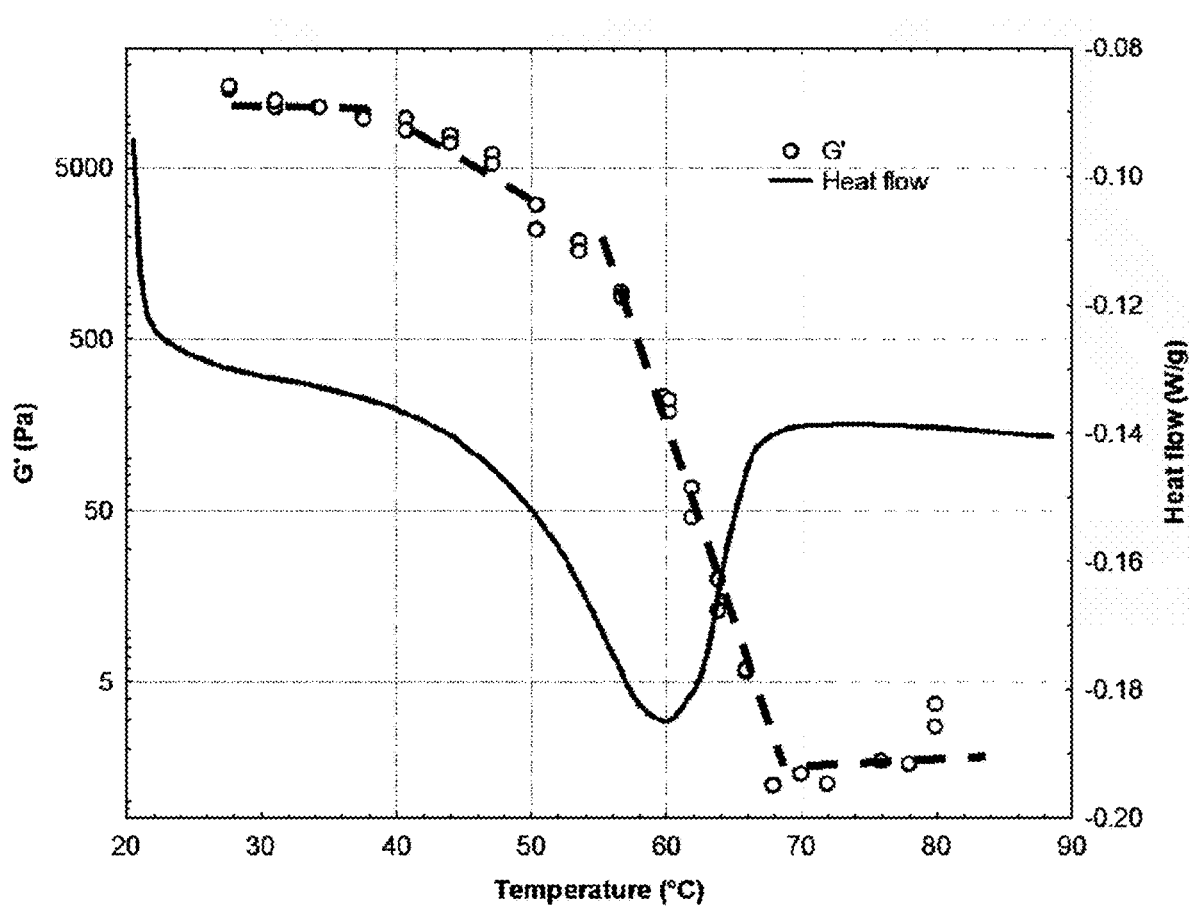
FIG. 36 is a plot showing the DSC melting trace of the composition with the elastic modulus of the composition. The plot shows the elastic modulus, also described as the structure of the solid, remained the same up to 40° C., then the product became softer as temperature increased because the sunflower wax started to melt at 39° C. The rate of structure loss increased after 50° C. where additional melting happened, and finally at 66° C. no structure remained because all the sunflower wax melted.
Figure 37:
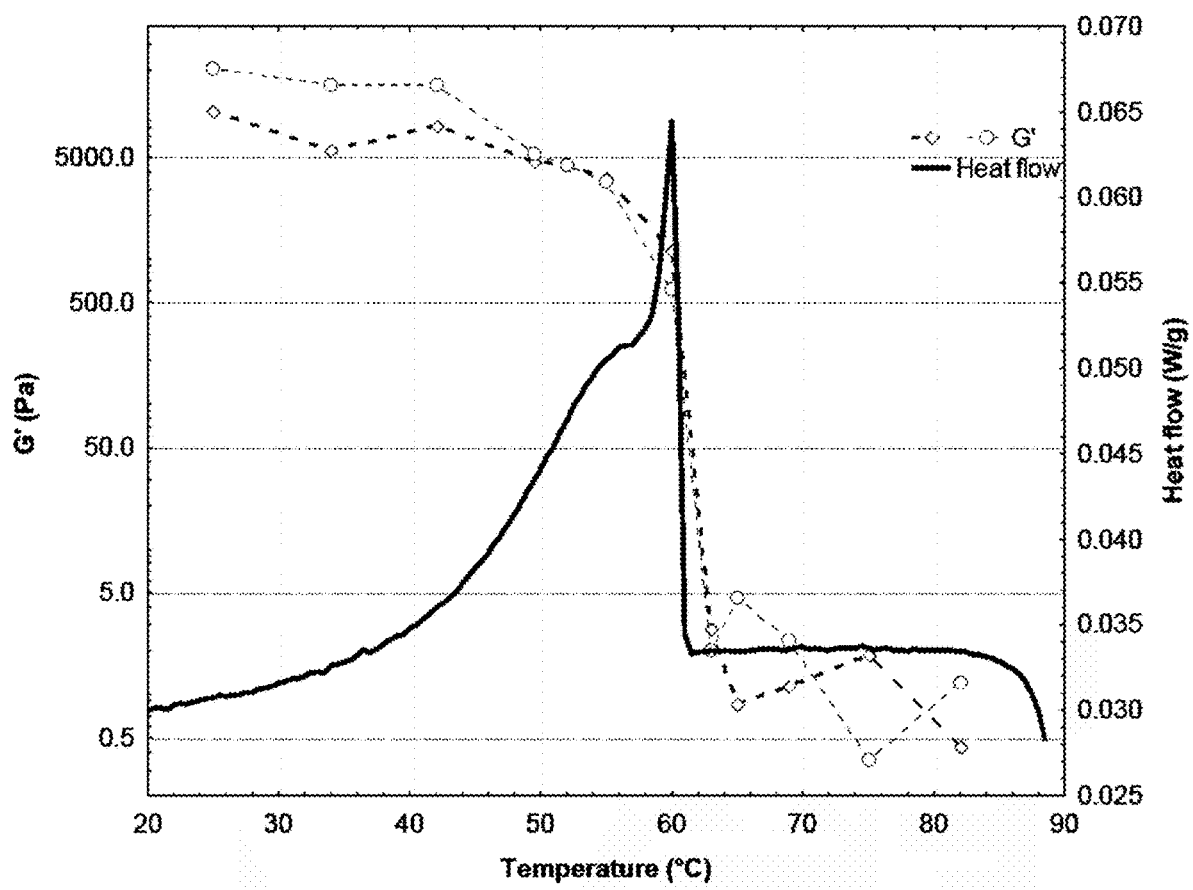
FIG. 37 is a plot showing the DSC crystallization trace of the composition with the elastic modulus of the composition. The plot shows that changes in the elastic modulus after 60° C. were similar regardless of whether the composition was melted or cooled.
Figure 38:
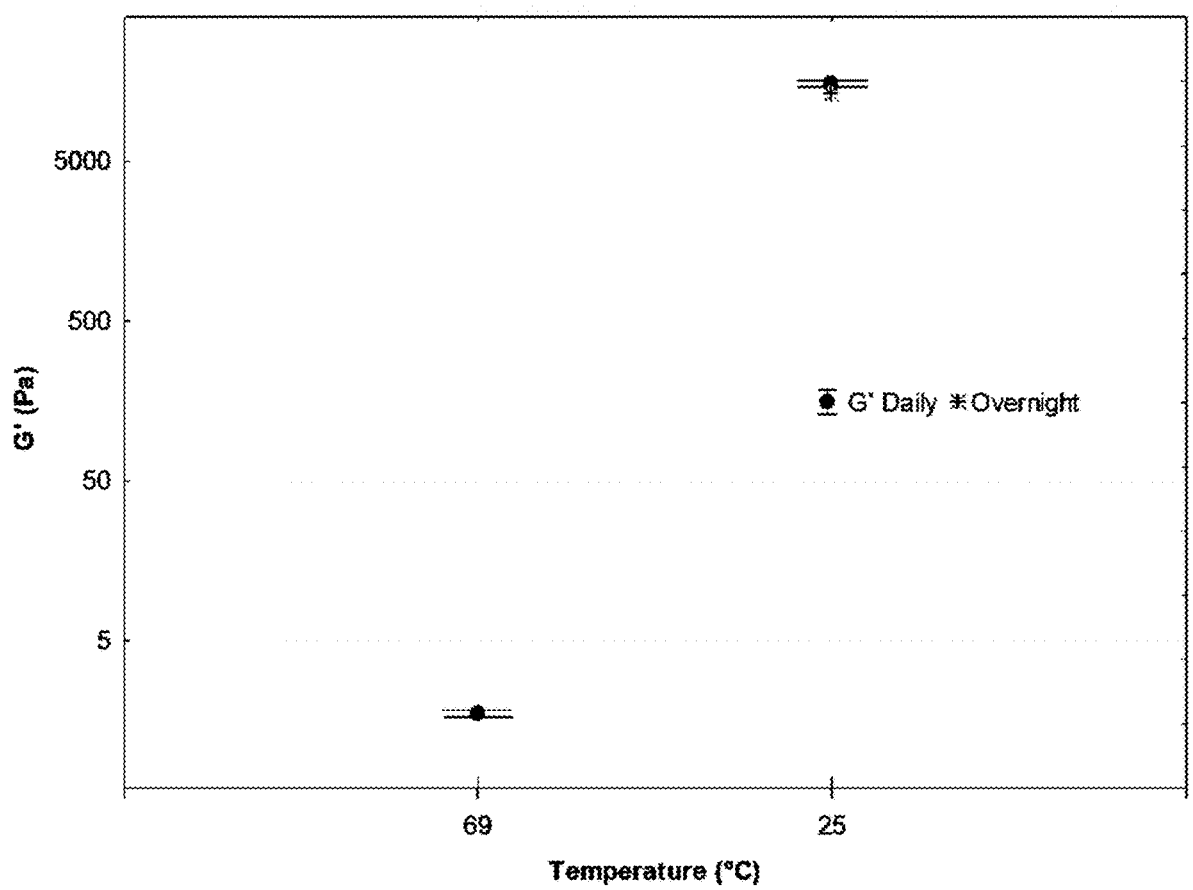
FIG. 38 is a plot showing the elastic modulus of the formulation F34 product with or without an overnight holding step. The plot shows there was no significant difference between the final G' value (hardness) between the sample crystallized in the rheometer with no overnight holding and with the overnight holding.

As observed in FIG. 36, the structure remained the same up to 40° C., then the product became softer as temperature increased since the sunflower wax started to melt at 39° C. The rate of structure loss increased after 50° C. where additional melting happened, and finally at 66° C. no structure remained since all the sunflower wax melted. The plot of G', while heating or cooling, presented slight changes concomitant with their differences observed in their corresponding thermograms. As observed in FIG. 37, when the sample was cooled at 5° C./min, there was no structural change detected from 90° C. to right before 60° C. Beyond 60° C., further cooling caused G' to increase suddenly, right where the SFW was known to have maximum crystallization. The thermal and mechanical results indicated that the formulation F34 product thermal stability was below 50° C. If the product were to be stored below this temperature, the slight structural changes would not affect the stability of the product. As observed in FIG. 38, there was no significant difference between the final G' value (hardness) between the sample crystallized in the rheometer with no overnight holding and with the overnight holding.

Figure 39:
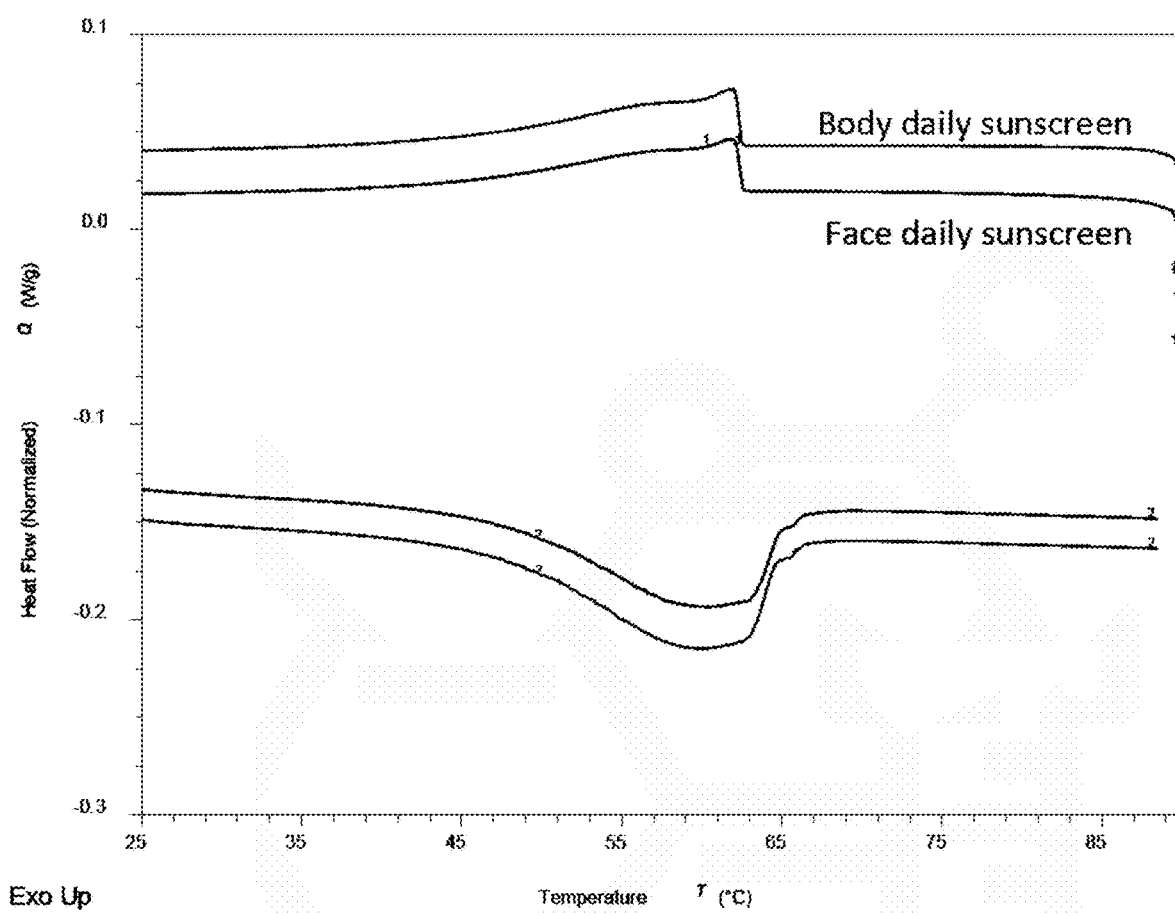
FIG. 39 is a plot showing the high resolution DSC melting and crystallization curves of the formulation F34 and formulation F26.

Similarly, an optimal process for producing a formulation F26 was determined while manufacturing in a reactor. The formulation F26 included 4.3 wt % SFW, 71.25 wt % FCO, 0.2 wt % vitamin E, 2.0 wt % ANTILEUKINE™ 6 also known as seaweed extract, 3.5 wt % SEPIFINE™ also known as babassu starch, and 18.75 wt % ZnO. The thermodynamic properties of the composition were characterized through differential scanning calorimetry in two cycles, wherein the heat flow (Q, W/g) in or out of the sample was measured (FIG. 39):

Crystallization: After completely melting the sample at 90° C. then it was cooled from 90 to 20° C. at 2° C./min.

Melting: Melting from 20° C. to 90° C. where the effect of processing is revealed.

Only two cycles were made in order to determine the optimal processing conditions and the differences between the formulation F34. Furthermore, mechanical characterization was performed. Oscillatory rheological assays were performed on the batches under only the crystallization condition to see if there was a difference in the organogelation mechanism in order to design the manufacture process.

After the results on the thermodynamics and the rheological properties of the formulation F26 did not present any differences with the formulation F34, the manufacturing process remained the same at first.

Example 4—Comparison of Sunscreens Made from Base Formula to Categorically Similar, Commercially Available Oleogel Sunscreens From the base formulation developed in Example 3 (e.g., F1-F10), two product sunscreens, for daily use (formulation F34) and for face use (formulation F26), were developed. Differences in the mechanical properties of these sunscreen formulations relative to sunscreens already on the market, including the BADGER® SPF30 active sunscreen (TX, USA), RAW ELEMENTS® sunscreen (CA, USA), TWO PEAS ORGANICS® sunscreen (CA, USA), EARTH MAMA® sunscreen (OR, USA), and OLITA® sunscreen (Mayagüez, Puerto Rico) were determined using various assays to determine their degrees of hardness and stiffness, sampling difficulty, resistance to oil release, and level of spreadability. Samples tested included all products within the mineral sunscreen category that corresponded to the same type of material known as "oleogels".

Oleogels are waterless formulations (e.g., anhydrous and/or with no added water (e.g., other than water naturally present in one or more of the raw components)), with Aw<0.7, or with less than 0.1% wt/wt). where a tridimensional crystal network (e.g., waxes) entraps a vegetable oil in a liquid state resulting in a non-flowing viscoelastic material. The products and their characteristics were summarized in Table III, and the manner in which the differences between these characteristics are determined are described as follows.

To evaluate the products within these categories the following degrees and levels were divided based on the mechanical properties results.

Figure 40:
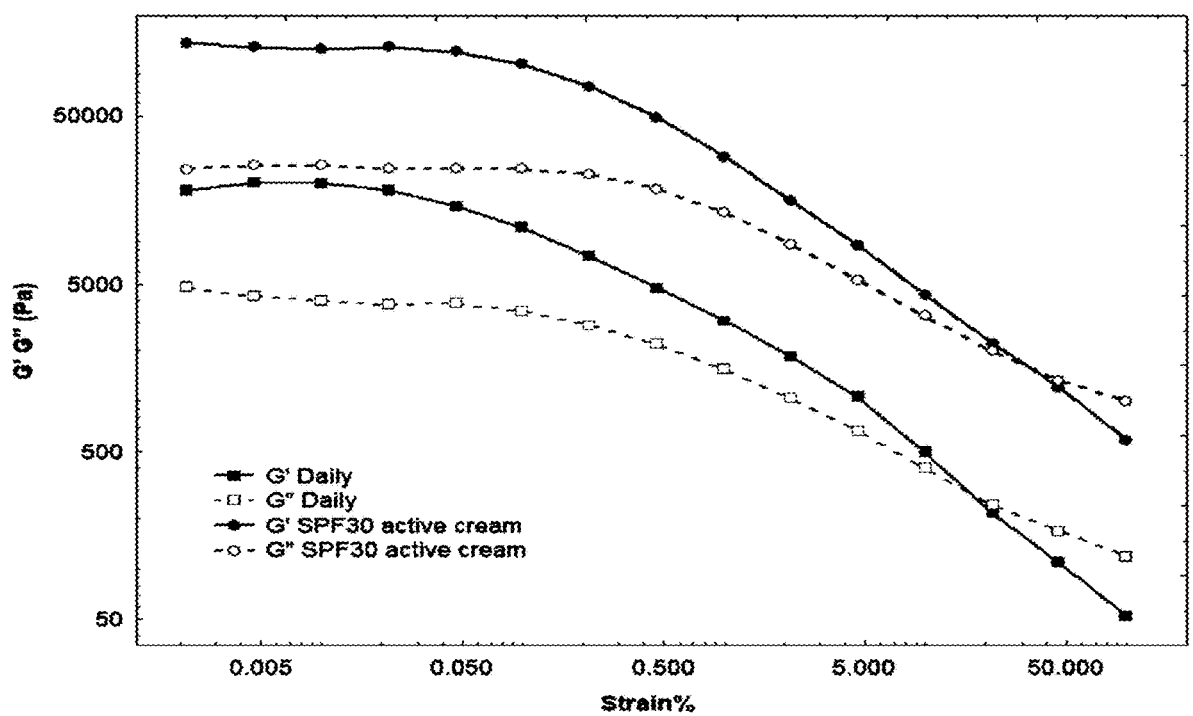
FIG. 40 is a plot showing an example of the resulting evolution of G' and G", where all of the products measured, including the new formulation F34, resulted with G' above G" at the lower strains, which is a characteristic of an oleogel.

An example of the resulting evolution of G' and G" is shown in FIG. 40 where all of the products measured resulted with G' above G" at the lower strains, which is a characteristic of an oleogel.

Figure 41:
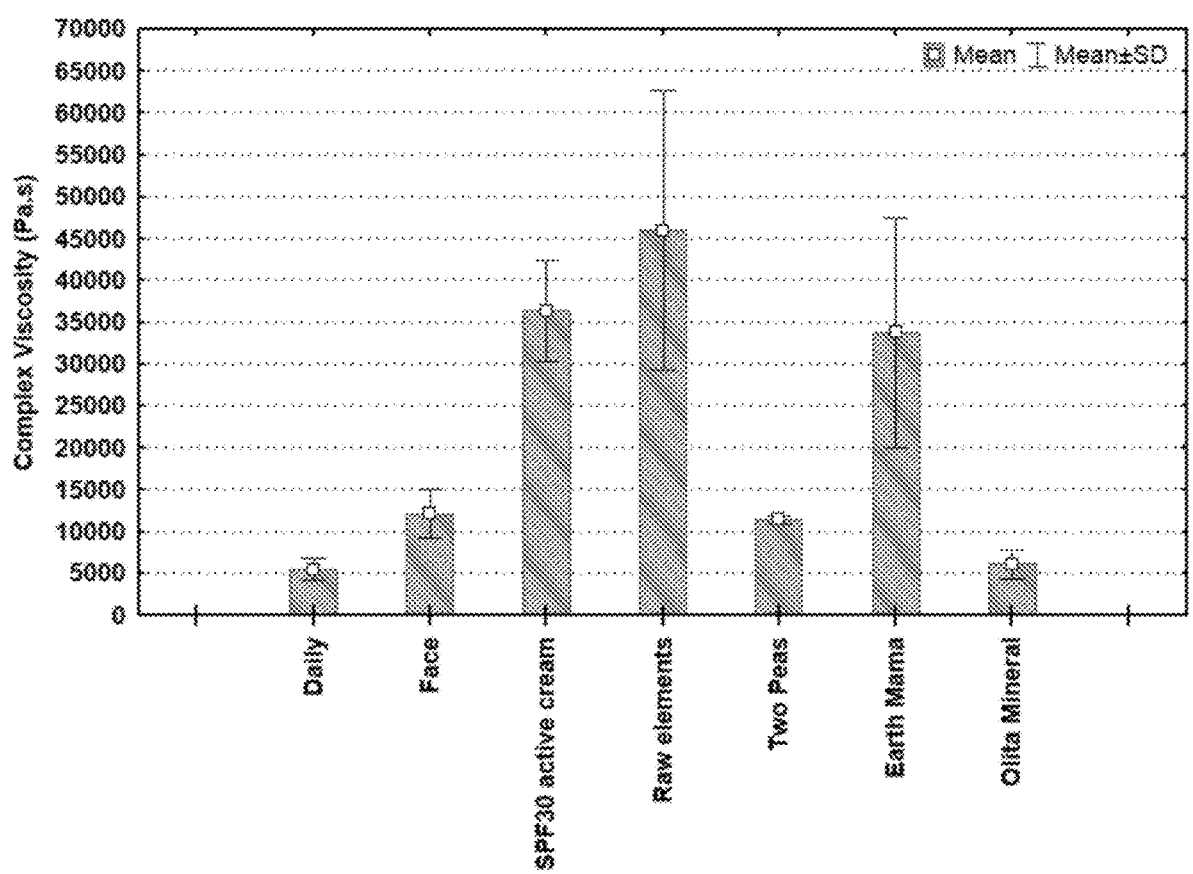
FIG. 41 is a plot showing the measured degree of hardness, or complex viscosity, in Pa-s, of the formulation F34 and formulation F26 described in the application, along with other product sunscreens, including the BADGER® SPF30 active sunscreen (TX, USA), RAW ELEMENTS® sunscreen (CA, USA), TWO PEAS ORGANICS® sunscreen (CA, USA), EARTH MAMA® sunscreen (OR, USA), and OLITA® sunscreen (Mayagüez, Puerto Rico).

The complex viscosity is a measurement of the viscoelasticity of the material measured as a resistance to deformation considering both the solid like (G') and the liquid like components (G"). Because G' governs the beginning of the strain sweep in oleogels, the viscoelasticity values (complex viscosity) within this region can be referred to as an overall hardness. As shown in FIG. 41, the formulation F34, formulation F26, TWO PEAS ORGANICS® (CA, USA) and OLITA® (Mayagüez, Puerto Rico) sunscreens resulted with the lowest hardness.

Figure 42:
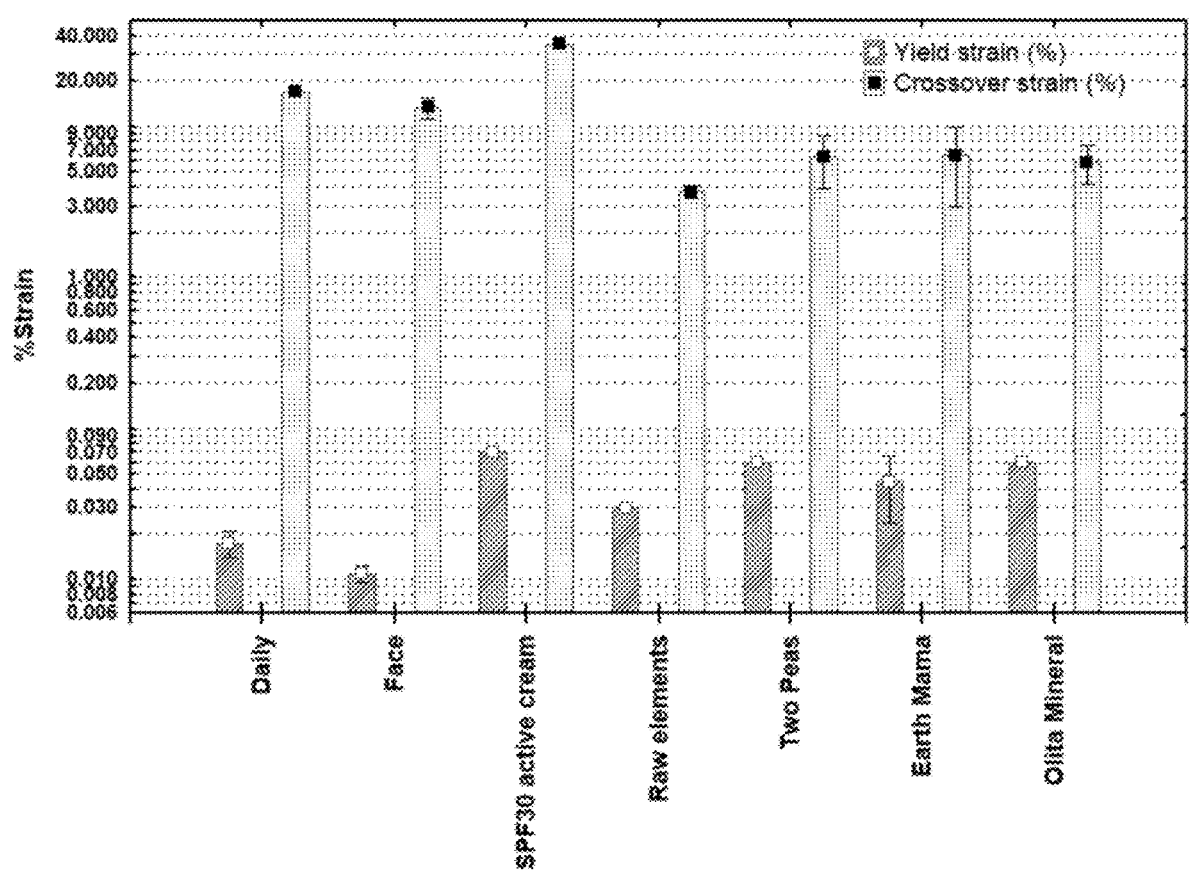
FIG. 42 is a plot showing the values of % strain of the formulations F34 and F26 described in the application, along with other product sunscreens, including the BADGER® SPF30 active sunscreen (TX, USA), RAW ELEMENTS® sunscreen (CA, USA), TWO PEAS ORGANICS® sunscreen (CA, USA), EARTH MAMA® sunscreen (OR, USA), and OLITA® sunscreen (Mayagüez, Puerto Rico).

The yield strain is the value where the viscoelasticity is no longer independent from deformation applied (e.g., % strain), this point is where the sample starts to deform elastically without breaking the integrity of the structure where it remains as an oleogel. The formulations F34 and F26 resulted in the lowest values of yield strain compared to all the others as shown in FIG. 42.

The crossover strain or also known as the flowing point is where the material deforms plastically which means that the integrity of the structure is compromised, therefore the tridimensional crystal structure is no longer capable of holding the liquid oil phase and it starts to flow. The formulation F34 and formulation F26 resulted with values lower than the SPF 30 active cream but higher than all the others.

Figure 43:
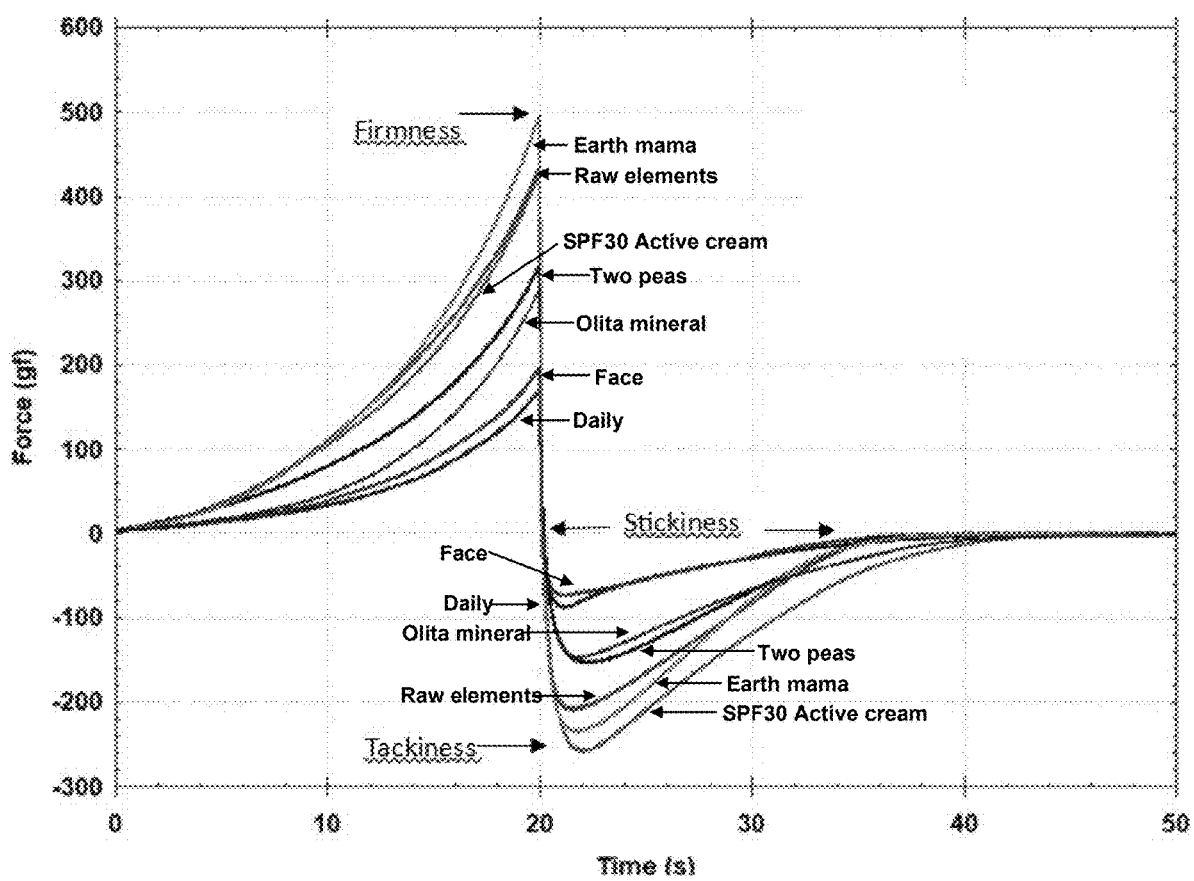
FIG. 43 is a plot showing the texture profile of the tested sunscreen products, where the evolution of the force used to push into the sample and lift the probe during the length of the test was recorded.
Figure 44:
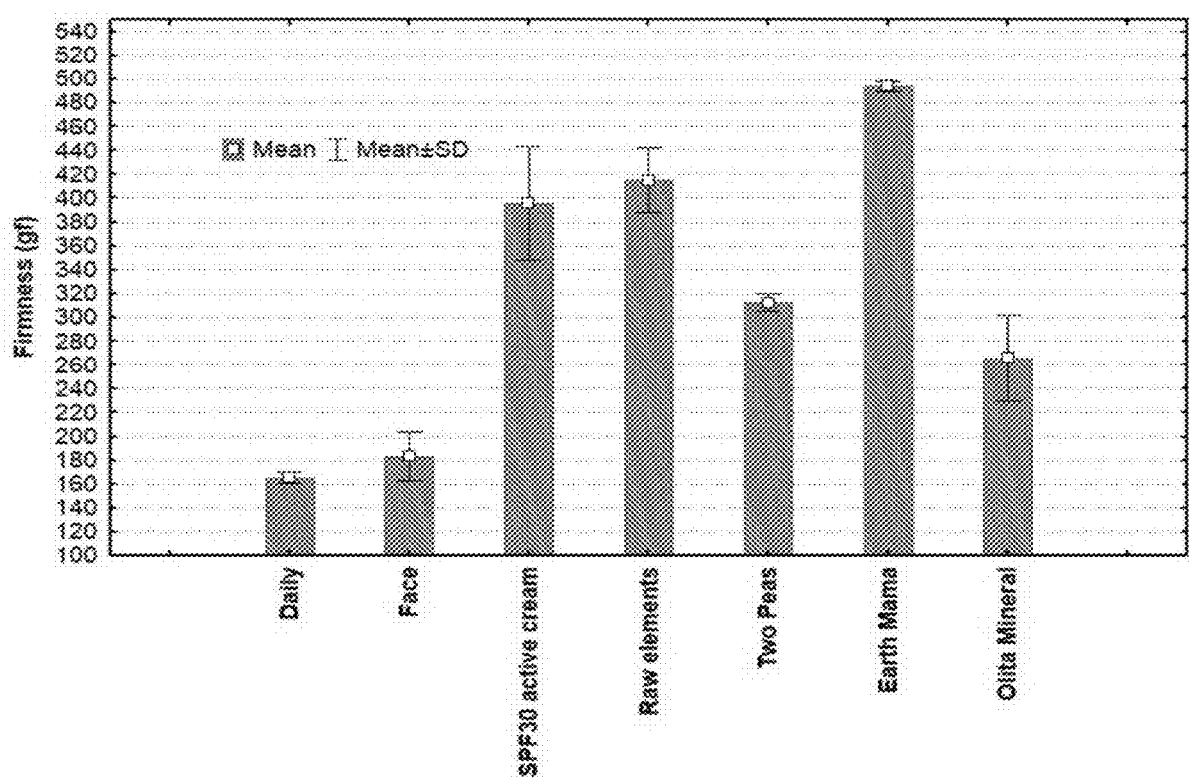
FIG. 44 is a plot showing firmness of the tested sunscreen products, determined from the maximum force required to penetrate 10 mm of the sample, which represents the mechanical resistance to deformation. The formulations F34 and F26 resulted with the lower values of firmness which was concomitant with the results of complex viscosity obtained from the rheology test.
Figure 45:
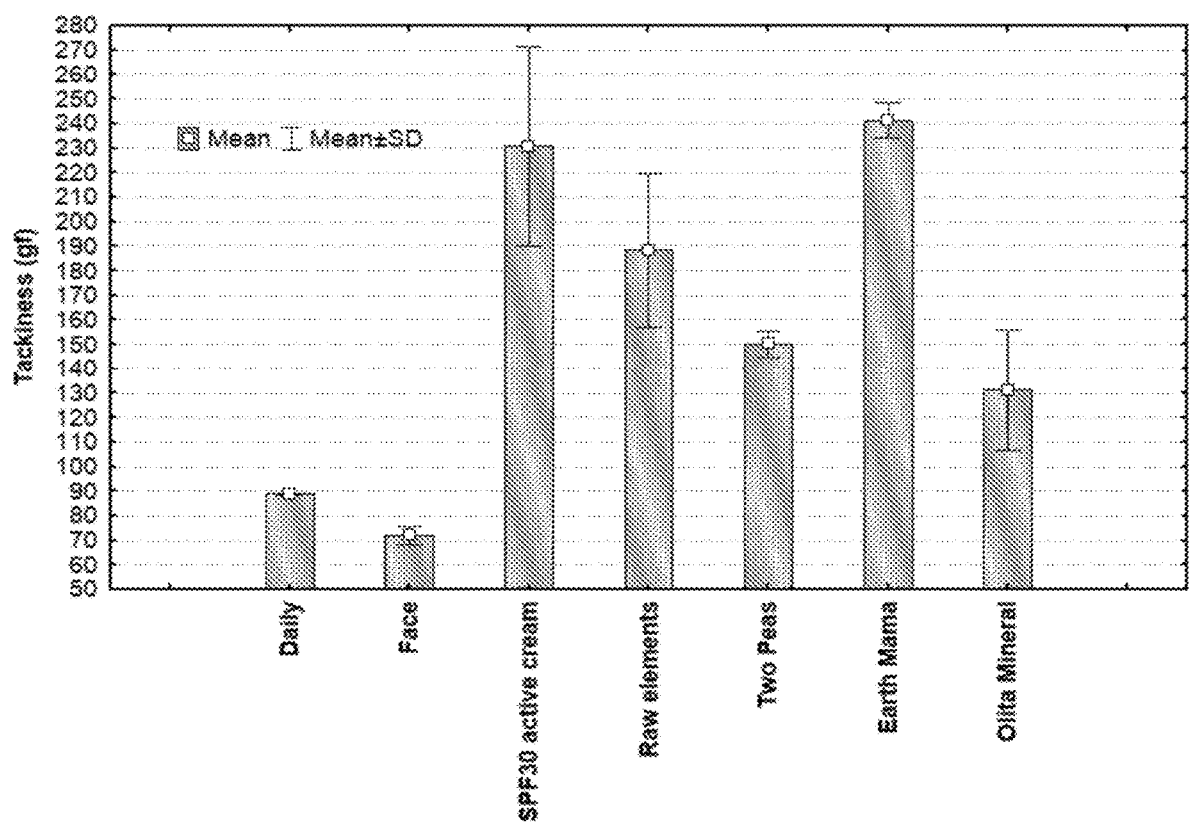
FIG. 45 is a plot showing the measured tackiness of the formulations F34 and F26 described in the application, along with other product sunscreens, including the BADGER® SPF30 active sunscreen (TX, USA), RAW ELEMENTS® sunscreen (CA, USA), TWO PEAS ORGANICS® sunscreen (CA, USA), EARTH MAMA® sunscreen (OR, USA), and OLITA® sunscreen (Mayagüez, Puerto Rico).
Figure 46:
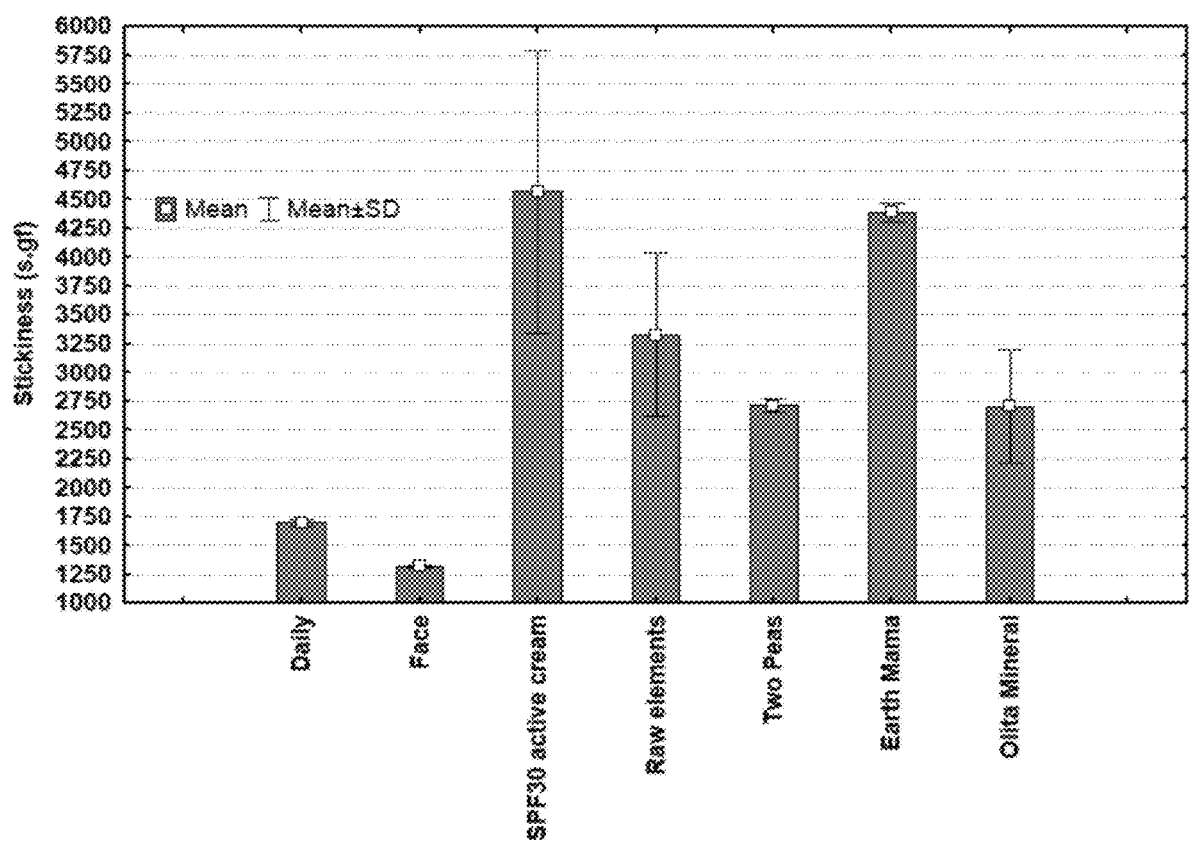
FIG. 46 is a plot showing the measured stickiness of the formulations F34 and F26 described in the application, along with other product sunscreens, including the BADGER® SPF30 active sunscreen (TX, USA), RAW ELEMENTS® sunscreen (CA, USA), TWO PEAS ORGANICS® sunscreen (CA, USA), EARTH MAMA® sunscreen (OR, USA), and OLITA® sunscreen (Mayagüez, Puerto Rico).

The texture profile is shown in FIG. 43 where the evolution of the force used to push and lift the probe during the length of the test was recorded. Firmness was determined from the maximum force required to penetrate 10 mm of the sample and therefore represents the mechanical resistance to deformation. As observed in FIG. 44, the formulations F34 and F26 resulted with the lower values of firmness which is concomitant with the results of complex viscosity obtained from the rheology test.

For the determination of tackiness and stickiness, the results depend on the degree of cohesive and adhesive forces of the sample. Tackiness is generally related more to the degree of cohesive forces (Noren et al., *Trends in Food Science & Technology*, 2019, ISSN 0924-2244.), that is the molecular forces that keep the material together (product to product bonds). A tacky material requires large forces to separate from the surface. During the texture analysis, the amount of force necessary to pull the probe from the sample is when the cohesive forces come to a failure and therefore it is related to the degree of tackiness.

Stickiness can be defined as the ability of a material to adhere to a surface where the extent of adhesive forces plays a greater role here (Noren et al., *Trends in Food Science & Technology*, 2019, ISSN 0924-2244.). During the texture analysis, when the probe is being pulled from the product the amount of force and time required to go back to the baseline (0 gf) is related to how much the product sticks to the probe. Therefore, the stickiness can be measured through the area under the curve as observed in FIG.

Figure 17:
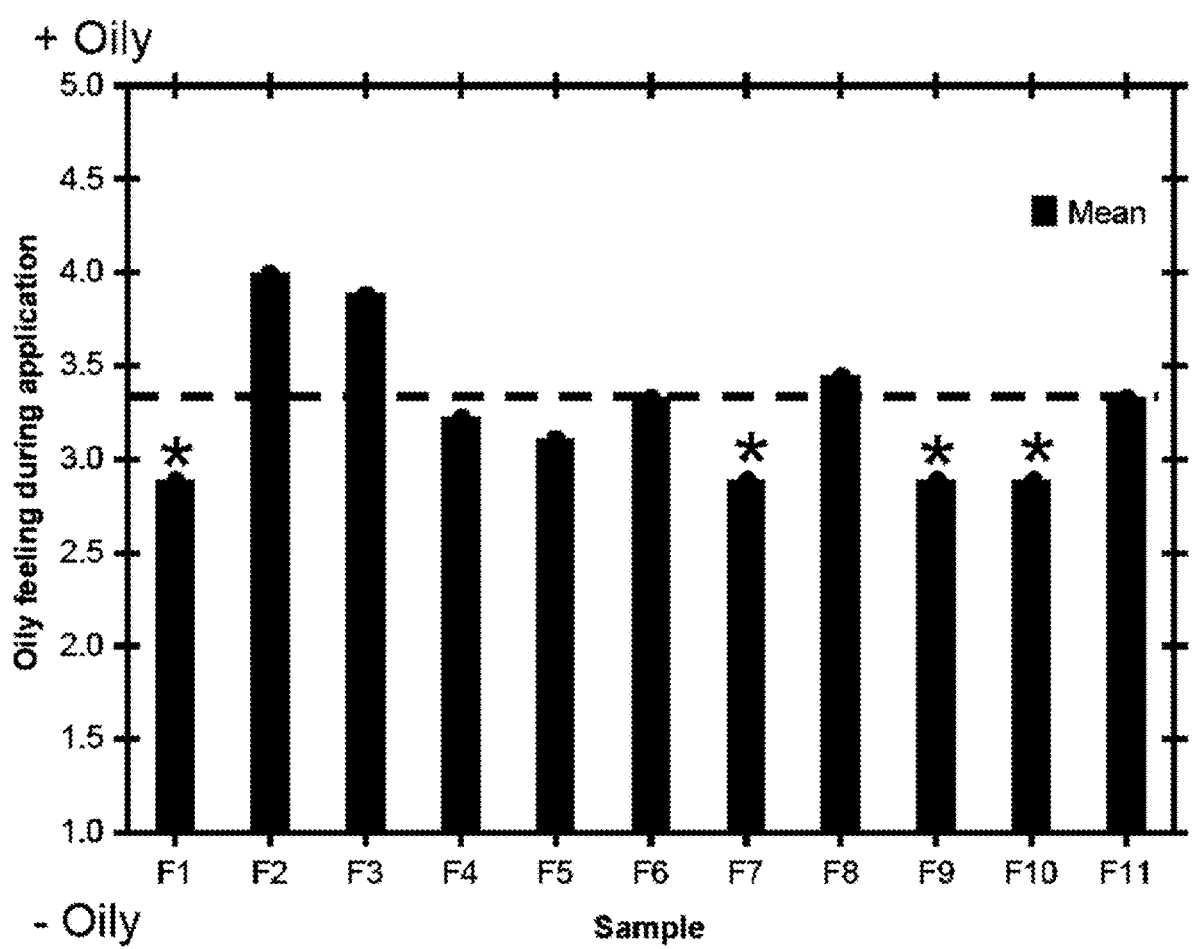
FIG. 17 is a plot showing the results from a sensorial test including nine participants who were asked to rate, between 1 (low) and 5 (high), how oily compositions F1-F11 felt during application.
Figure 18:
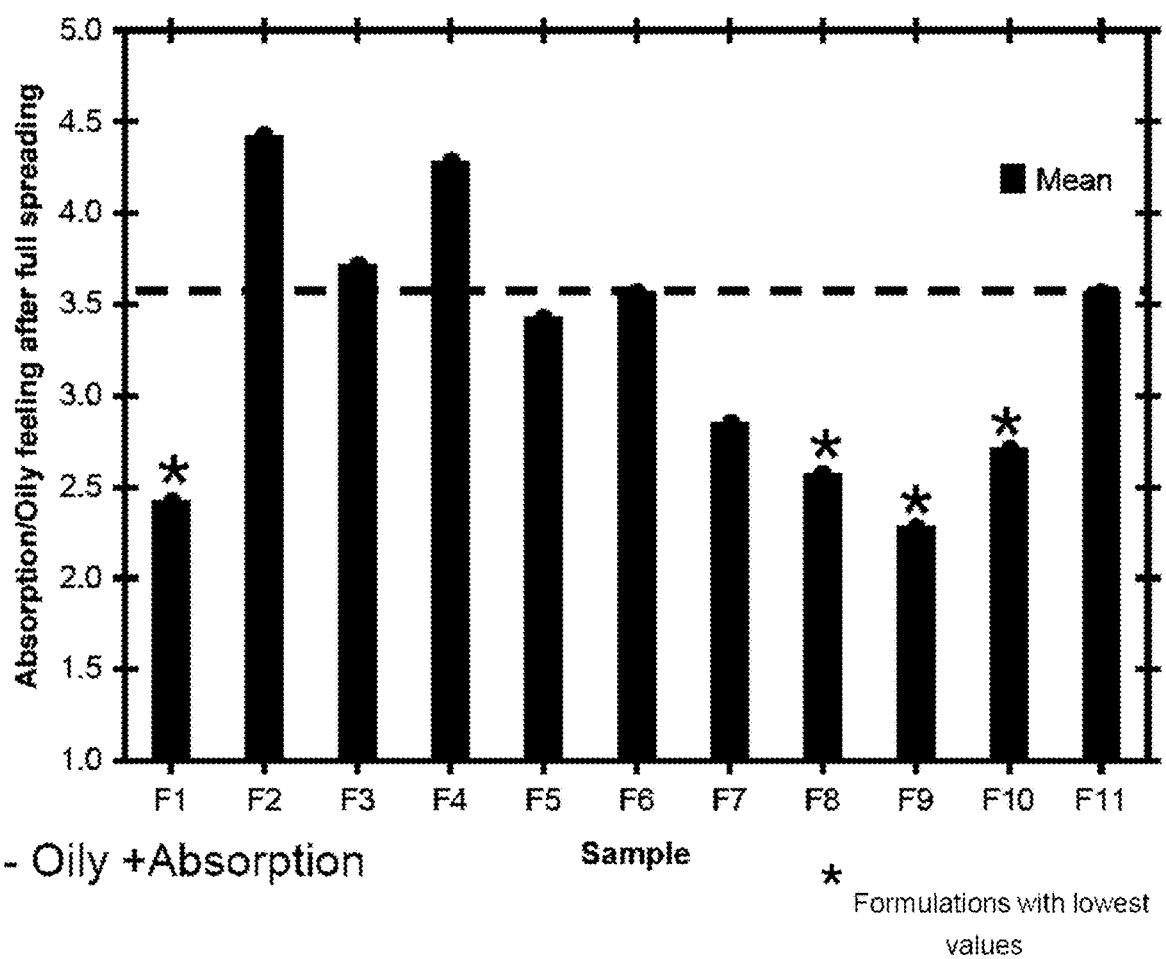
FIG. 18 is a plot showing the results from a sensorial test including nine participants who were asked to rate, between 1 (low) and 5 (high), how oily compositions F1-F11 felt once fully spread on their skin.
Figure 19:
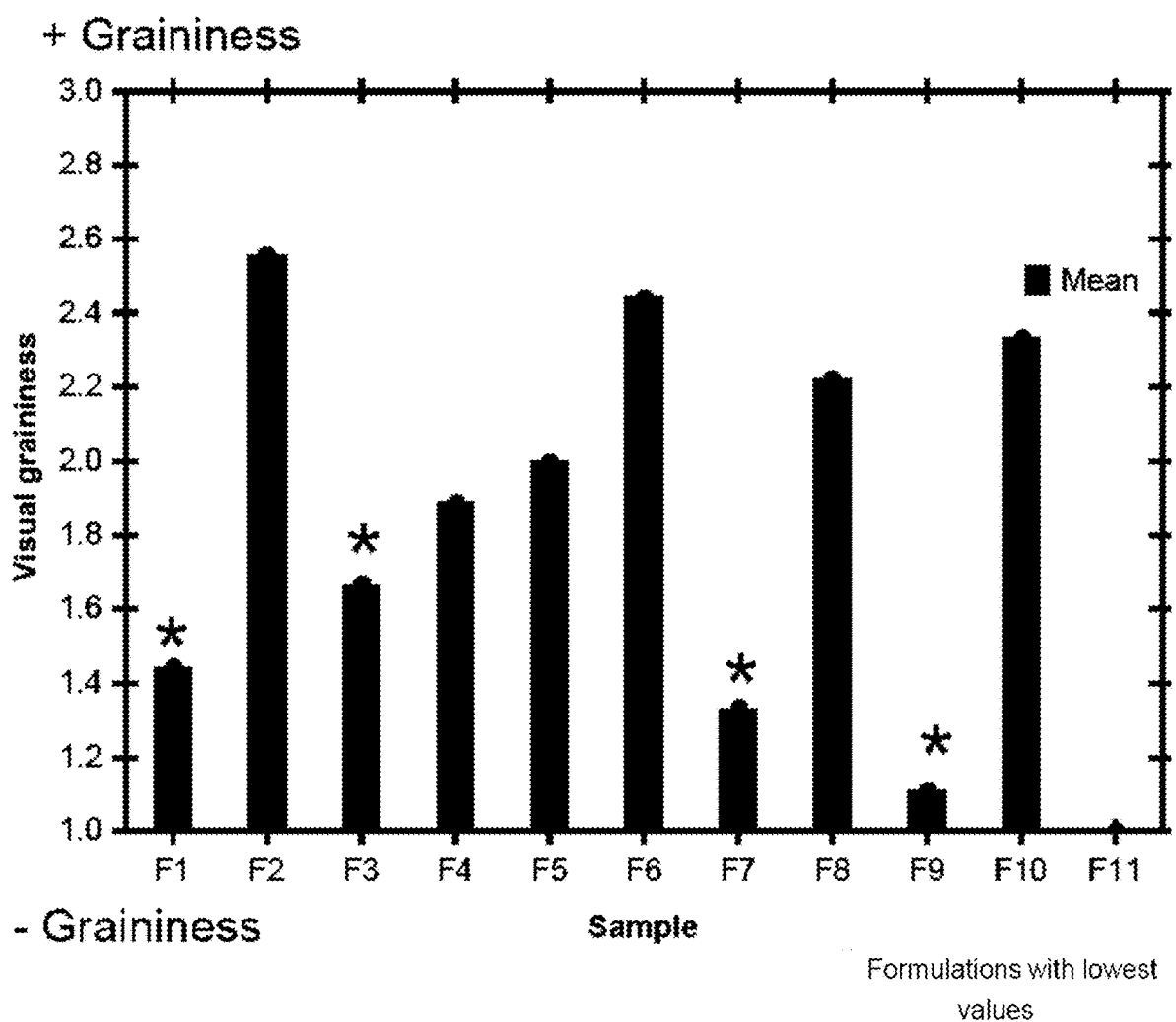
FIG. 19 is a plot showing the results from a sensorial test including nine participants who were asked to rate, between 1 (low) and 5 (high), how grainy compositions F1-F11 appeared.
Figure 20:
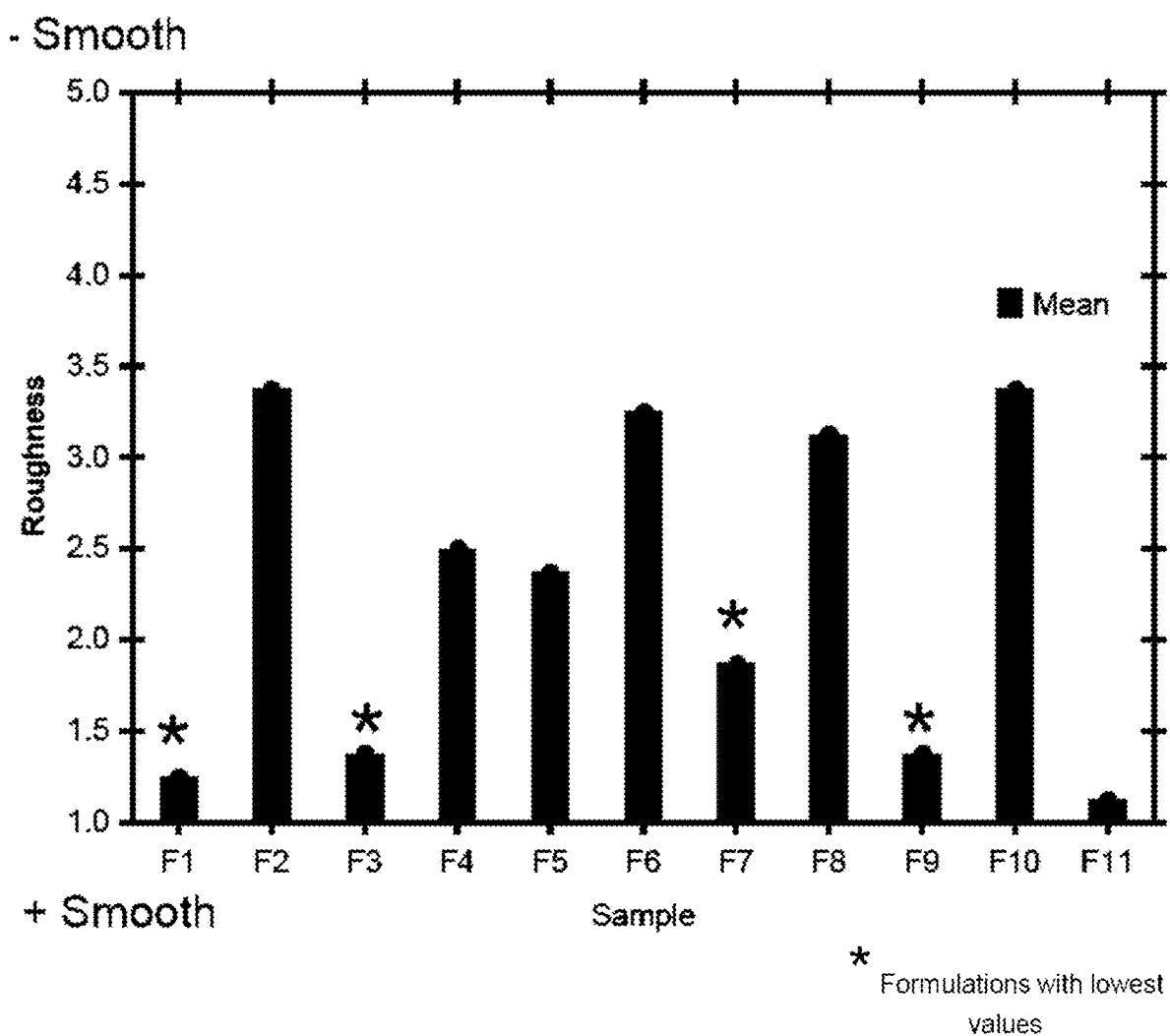
FIG. 20 is a plot showing the results from a sensorial test including nine participants who were asked to rate, between 1 (low) and 5 (high), how rough compositions F1-F11 felt on their skin.

The texture profile is shown in. For both the tackiness and stickiness measurements, the formulations F34 and F26 resulted with the lowest values as shown in FIGS. 17 and 18. The categories and associations of mechanical properties related to skin feel are shown in Table III.

As shown in Table IV below, the formulations F34 and F26 resulted in the lowest values of all the categories except for the resistance to oil release (medium). Therefore, the formulations F34 and F26 can be described as a flexible soft product easy to apply evenly throughout the skin with a dry sensation and smooth after-feel. Inactive ingredients for each of the sunscreens in Table IV are listed as follows: BADGER® SPF30 (TX, USA) formulation F34 includes the following inactive ingredients: caprylic/capric triglyceride (organic steam distilled coconut oil), *Helianthus annus* (sunflower) wax, and tocopherol (sunflower vitamin e). BADGER®, SPF30 (TX, USA) formulation F26 includes the following inactive ingredients: organic steam distilled coconut oil, sunflower wax, babassu starch, fractionated coconut oil, golden seaweed extract, and sunflower vitamin E.

BADGER® SPF30 active sunscreen (TX, USA) cream includes the following inactive ingredients: *Helianthus annuus* (sunflower) seed oil, *cera alba* (beeswax), tocopherol (sunflower vitamin e), and *Hippophae rhamnoides* (sea buckthorn) fruit extract.

RAW ELEMENTS® SPF30 Face+Body sunscreen (CA, USA) includes the following inactive ingredients: *sinensis* leaf extract (organic green tea), *Camellia sinensis* leaf extract (organic black tea), *Cannabis sativa* seed oil (organic hemp seed oil), *cera alba* (organic beeswax), *Coffea arabica* seed extract (organic coffee bean), *Helianthus annuus* seed oil (organic sunflower oil), *Mangifera indica* seed butter (natural mango butter), *Rosmarinus officinalis* leaf oil (natural rosemary), *Theobroma cacao* seed butter (cocoa butter), and tocopherol.

TWO PEAS ORGANICS® SPF30 sunscreen (CA, USA) includes the following inactive ingredients: *Ricinus communis* (castor) oil, beeswax, *Cocos nucifera* (coconut) oil, *Olea europaea* (olive) fruit oil, *Simmondsia chinensis* (jojoba) oil, *Butyrospermum parkii* (shea) butter, *Helianthus annuus* (sunflower) seed oil, and tocopherol (vitamin E).

EARTH MAMA® (OR, USA) SPF25 Tinted sunscreen lotion includes the following inactive ingredients: caprylic/capric triglyceride, *Cocos nucifera* (coconut) oil, *Olea europaea* (olive) fruit oil, beeswax, *Helianthus annuus* (sunflower seed oil, *Simmondsia chinensis* (jojoba) oil, *Butyrospermum parkii* (shea) butter, *Rubus idaeus* (raspberry) seed oil, *Argania spinosa* kerner oil, tocopherol, *Rosa canina* (rosehip) seed oil, *Calendula officinalis* flower extract, iron oxides, and mica.

OLITA® (Mayagüez, Puerto Rico) Mineral SPF30 mineral sunscreen includes the following inactive ingredients: *Helianthus annuus* (sunflower) seed oil, beeswax, *Ricinus communis* (castor) seed oil, *Cocos nucifera* (coconut) oil, *Olea europaea* (olive) fruit oil, *Simmondsia chinensis* (jojoba) seed oil, *Butyrospermum parkii* (shea) butter, and tocopherol.

TABLE IV

Analyzed products, active ingredient quantities, and their scores on degree of hardness, degree of stiffness, sampling difficulty, resistance to oil release, and level of spreadability.

| Brand | Formulation F34 | Formulation F26 | BADGER® (TX, USA) | RAW ELEMENTS® (CA, USA) | TWO PEAS ORGANICS® (CA, USA) | EARTH MAMA® (OR, USA) | OLITA® (Mayagüez, Puerto Rico) |
|---|---|---|---|---|---|---|---|
| Product | SPF30 Formulation F34 | SPF30 Formulation F26 | SPF 30 Active sunscreen cream | SPF30 Face + Body sunscreen | SPF30 sunscreen | SPF25 Tinted sunscreen lotion | SPF30 mineral sunscreen |
| Listed active ingredients (wt %) | ZnO 18.75% | ZnO 18.75% | uncoated ZnO 18.75% | ZnO 23% | ZnO 20% | ZnO 20% | ZnO 20% |
| Degree of hardness.[a] | Low | Low | Medium | High | Low | Medium | Low |
| Degree of Stiffness.[b] | Low | Low | High | High | Medium | High | Medium |
| Sampling difficulty.[c] | Easy | Easy | Difficult | Moderate | Difficult | Difficult | Difficult |
| Resistance to oil release.[d] | Medium | Medium | High | Low | Low | Low | Low |
| Level of spreadability.[e] | Easy | Easy | Difficult | Moderate | Moderate | Difficult | Moderate |

TABLE IV-continued

Analyzed products, active ingredient quantities, and their scores on degree of hardness, degree of stiffness, sampling difficulty, resistance to oil release, and level of spreadability.

| Brand | Formulation F34 | Formulation F26 | BADGER ® (TX, USA) | RAW ELEMENTS ® (CA, USA) | TWO PEAS ORGANICS ® (CA, USA) | EARTH MAMA ® (OR, USA) | OLITA ® (Mayagüez, Puerto Rico) |
|---|---|---|---|---|---|---|---|

[a]Sensation: Soft or hard; Mechanical property: complex viscosity
[b]Sensation: difficulty to move. Mechanical property: firmness
[c]Sensation: amount of force necessary to start spreading. Mechanical property: yield strain
[d]Sensation: amount of force necessary to start to feel the oil. Mechanical property: crossover strain
[e]Sensation: level of grip, drag and after-feel. Mechanical property: tackiness and stickiness.

Example 5—Processing Conditions for the Manufacture of Sunscreen Formulations

Processing conditions were explored for generating sunscreen formulations containing different oils and waxes. These processing conditions were further optimized for the sunscreen formulations with beneficial properties identified in the Examples above.

General Processing Conditions

Mixing speeds and mixing times depended on the size of the equipment used and batch size. The temperatures also depended on the type of wax and additives used but could be broken down into two different groups as follows:
1. For samples containing one or more waxes with high melting point (above 65° C., e.g., Sunflower wax):
The oil and wax components were combined and heated to about 75-95° C. while mixing. Then, zinc oxide was added while mixing. The zinc oxide was dispersed with or without vacuum and with or without a high shear mixing for about 1-800 minutes. The components were then cooled with or without vacuum to about 62-74° C. while mixing with or without a high shear mixer. Then additives (e.g., tocopherol for formulation 34 and the combination of tocopherol, SEPIFINE™ (babassu starch), and ANTILEUKINE™ 6 for formulation 26) were added and dispersed into the mix with or without while mixing for about 1-800 minutes. The composition was held at about 62-74° C. for about 0-800 min while mixing. The components were cooled to about 48-61° C. while mixing. The components were transferred from the main vessel to a side vessel for filling or filled directly from main vessel with or without mixing with optional use of recirculation of the composition with control of the temperature from 48-61° C. The composition was filled in the final containers with or without mixing.
2. For samples containing only low melting point waxes (lower than 65° C., e.g., Beeswax or Candelilla wax):
The oil and wax components were combined and heated to about 55-95° C. while mixing. Then, zinc oxide was added while mixing. The zinc oxide was dispersed with or without vacuum and with or without a high shear mixing for about 1-800 minutes. The components were then cooled with or without vacuum to about 40-68° C. while mixing with or without a high shear mixer. Then additives were added and dispersed into the mix with or without while mixing for about 1-800 minutes. The composition was held at about 40-68° C. for about 0-800 min while mixing. The components were cooled to about 25-48° C. while mixing. The components were transferred from the main vessel to a side vessel for filling or filled directly from main vessel with or without mixing with optional use of recirculation of the composition with control of the temperature from 25-48° C. The composition was filled in the final containers with or without mixing.

Small Batch Processing Conditions

To determine how to scale sunscreen formulations of the disclosure, such as formulation F34, and to optimize processing conditions, the following engineering process was determined for the formulations disclosed such as formulation F34 in a reactor: The waxes were melted to a temperature high enough to melt completely the wax components. Afterwards, the mixing speeds were set to effectively move the entire product to ensure a homogeneous temperature and to disperse properly all the components (e.g., zinc oxide). Then, while cooling the mixing speeds were set where they didn't interfere with the formation of the desired crystal network that led to the ideal texture. Finally, a filling temperature was also set based on the final desired texture and stability of the organogel.

Product Processing Conditions

The formulation for F34 and F26 is shown in Table V.

TABLE V

Production of Formulation F34 and Formulation F26.

| | Formulation F34 (wt %) | Formulation F26 (wt %) |
|---|---|---|
| Sunflower wax | 4.3 | 4.3 |
| Beeswax | 0 | 0 |
| Fractionated coconut oil | 76.75 | 71.25 |
| vitamin e (tocopherol) | 0.2 | 0.2 |
| babassu starch | 0 | 3.5 |
| seaweed extract | 0 | 2 |
| ZnO | 18.75 | 18.75 |
| % TOTAL | 100 | 100 |

Fractionated coconut oil and sunflower wax were added to the main vessel and heated under vacuum of about 0.4 below atmospheric pressure to about 75-85° C. (e.g., 80° C., 82° C., or 83° C.) with the central mixer at about 0.85-1.05 s$^{-1}$ (e.g., 0.93, 0.95, or 0.97 s$^{-1}$) and the anchor mixer at about 0.80-1.00 s$^{-1}$ (e.g., 0.87, 0.90, or 0.93 s$^{-1}$). Once the mix reached about 75-85° C. (e.g., 80° C., 82° C., or 83° C.), the zinc oxide was inducted while mixing with the central mixer at about 0.85-1.05 s$^{-1}$ (e.g., 0.93, 0.95, or 0.97 s$^{-1}$), the anchor mixer at about 0.80-1.00 s$^{-1}$ (e.g., 0.87, 0.90, or 0.93 s$^{-1}$) and the rotor stator at about 9.50-11.50 s$^{-1}$ (e.g., 9.85, 10.47, or 11.03 s$^{-1}$). Then the zinc oxide was dispersed under vacuum about 0.4 below atmospheric pressure with the central mixer at about 1.50-1.70 s$^{-1}$ (e.g., 1.52, 1.58, or 1.61 s$^{-1}$), the anchor mixer at about 1.50-1.60 s$^{-1}$ (e.g., 1.50, 1.51, or 1.54 s$^{-1}$) and the rotor stator at about 12.00-13.50 s$^{-1}$ (e.g., 12.57, 12.83, or 13.06 s$^{-1}$) for about 275-300 minutes (e.g., 284, 290, or 292 minutes) for formulation F34 and about 160-190 minutes (e.g., 165, 174, or 189 minutes) for formulation F26. Afterwards, the mixture was cooled under vacuum about 0.4 below atmospheric pressure to about 69-75° C. (e.g., 69° C., 70° C., or 72° C.) with the central mixer at about 0.85-1.05 s$^{-1}$ (e.g., 0.93, 0.95, or 0.97 s$^{-1}$), the anchor mixer at about 0.80-1.00 s$^{-1}$ (e.g., 0.87, 0.90, or 0.93 s$^{-1}$) and the rotor stator at about 12.00-13.50 s$^{-1}$ (e.g., 12.57, 12.83, or 13.06 s$^{-1}$). Then the tocopherol (vitamin E) was added for formulation F34 and the additives were added for formulation F26 (seaweed extract and babassu starch) while maintaining the same mixing rates and afterwards was dispersed into the mix under vacuum about 0.4 below atmospheric pressure with the central mixer at about 1.50-1.70 s$^{-1}$ (e.g., 1.52, 1.58, or 1.61 s$^{-1}$), the anchor mixer at about 1.50-1.60 s$^{-1}$ (e.g., 1.50, 1.51, or 1.54 s$^{-1}$) and the rotor stator at about 12.00-13.50 s$^{-1}$ (e.g., 12.57, 12.83, or 13.06 s$^{-1}$) for about 500-600 minutes (e.g., 543, 554, or 570 minutes) for formulation F34 and about 300-360 minutes (e.g., 305, 332, or 345 minutes) for formulation F26. Then the rotor stator was turned off and left at about 69-75° C. (e.g., 69° C., 70° C., or 72° C.) with the central mixer at about 1.50-1.70 s$^{-1}$ (e.g., 1.52, 1.58, or 1.61 s$^{-1}$) and the anchor mixer at about 1.50-1.60 s$^{-1}$ (e.g., 1.50, 1.51, or 1.54 s$^{-1}$) for about 720-800 minutes (e.g., 725, 750, or 800 minutes). Afterwards, the mix was cooled to about 62-68° C. (66° C., 67° C., or 68° C.) with the central mixer at about 1.50-1.70 s$^{-1}$ (e.g., 1.52, 1.58, or 1.61 s$^{-1}$) and the anchor mixer at about 1.50-1.60 s$^{-1}$ (e.g., 1.50, 1.51, or 1.54 s$^{-1}$). The cooling then proceeded to about 51-61° C. (e.g., 54° C., 56° C., or 57° C.) for formulation F34 and about 51-61° C. (e.g., 54° C., 56° C., or 58° C.) for formulation F26 with the central mixer at 0.92 s$^{-1}$ and the anchor mixer at about 0.80-1.00 s$^{-1}$ (e.g., 0.87, 0.90, or 0.93 s$^{-1}$). The mix then was transferred from the main vessel to a side vessel for filling where the product was mixed and recirculated while maintaining the last temperature of the main vessel (about 51-61° C. (e.g., 54° C., 56° C., or 57° C.)) for formulation F34 and about 51-61° C. (e.g., 54° C., 56° C., or 58° C. for formulation F26) while mixing at about 0.14-0.16 s$^{-1}$ (e.g., 0.14, 0.15, 0.16 s$^{-1}$) until all the product was filled. From this transfer vessel, the product was placed into a hopper for filling where the hopper was mixed constantly until all of the product was filled.

Example 6—Use of the Sunscreen Formulations on Skin

Sunscreen formulations described herein (e.g., formulation F34 formulation or formulation F26 formulation, among others) may be used to prevent or reduce the risk of skin damage, e.g., by blocking UV light from sun exposure. The composition can be applied to the skin, spread evenly, and allowed to dry or absorb. The composition is then reapplied as needed in intervals to replenish the sunlight blocking components, e.g., as the composition is washed or worn off of the skin. The sunscreen may be applied to the skin 15 minutes prior to exposure of the skin to sunlight. Roughly one ounce of sunscreen may be used to cover the body. The sunscreen may be applied to all skin not covered by clothing, including the neck, face, ears, tops of the feet, and legs. The sunscreen may be reapplied every forty minutes or immediately after swimming or sweating in order to provide sun protection when outdoors. The sunscreen should be applied such that there is 2 mg/cm$^2$ on the skin to provide adequate protection from the sun using an SPF30 sunscreen as determined by FDA testing for SPF30 sunscreen.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Although specific compositions and methods have been disclosed, a number of other embodiments and modifications may be made without departing from the spirit and scope of the invention. It should be apparent, however, to those skilled in the art that many more modifications besides those already described are possible without departing from the inventive concepts described herein. The inventive subject matter, therefore, is not to be restricted except in the spirit of the disclosure.

All patents, patent publications and publications mentioned herein are incorporated herein by reference in their entirety to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

The invention claimed is:

1. A composition comprising an oil component, a wax component, a broad spectrum UV absorber component, and an additive component, wherein the oil component comprises between 50 wt % and 90 wt % of the composition, the wax component comprises between 0.1 wt % and 10 wt % of the composition, the additive component comprises between 0 wt % and 20 wt % of the composition, and the broad spectrum UV absorber component comprises between 10 wt % and 30 wt % of the composition, wherein the composition lacks an emulsifier, and wherein the composition exhibits a crossover strain >8%.

2. The composition of claim 1, wherein the composition comprises between 0 wt % and 5 wt % water.

3. The composition of claim 1, wherein the composition lacks a preservative or a stabilizer.

4. The composition of claim 1, wherein the composition consists of or consists essentially of the oil component, the wax component, the broad spectrum UV absorber, and the additive component.

5. The composition of claim 1, wherein the oil component comprises coconut oil, fractionated coconut oil, medium chain triglycerides (MCT oil), babassu oil, baobab oil, sunflower oil, canola oil, apricot oil, rice oil, sesame oil, grapeseed oil, linseed oil, hemp oil, pomegranate oil, jojoba oil, Abyssinian seed oil, a mixture of alkanes of vegetable origin, or any combination thereof.

6. The composition of claim 1, wherein the oil component comprises a first oil and a second oil, wherein a ratio of the first oil and the second oil is between 1:100 wt/wt to 100:1 wt/wt.

7. The composition of claim 1, wherein the wax component comprises sunflower wax, rice bran wax, carnauba wax, or any combination thereof.

8. The composition of claim 1, wherein the wax component comprises a first wax and a second wax, wherein a ratio of the first wax and the second wax is between 1:100 wt/wt to 100:1 wt/wt.

9. The composition of claim 1, wherein the wax component comprises a naturally occurring wax from a single source or an extract thereof.

10. The composition of claim 1, wherein the wax component comprises 0.5 wt % to 8 wt % of the composition.

11. The composition of claim 1, wherein the broad spectrum UV absorber component comprises zinc oxide (ZnO), titanium dioxide ($TiO_2$), p-aminobenzoic acid, 3-(4-tert-butylphenyl)-1-(4-methoxyphenyl)propane-1,3-dione, 2-ethoxyethyl (2E)-3-(4-methoxyphenyl)prop-2-enoate, (2-hydroxy-4-methoxyphenyl)(2-hydroxyphenyl)methanone, 3,3,5-trimethylcyclohexyl 2-hydroxybenzoate, (1R, 3R,4S)-p-menthan-3-yl 2-aminobenzoate, 2-ethylhexyl 2-cyano-3,3-diphenylprop-2-enoate, (RS)-2-ethylhexyl (2E)-3-(4-methoxyphenyl)prop-2-enoate, 2-ethylhexyl 2-hydroxybenzoate, 2-ethylhexyl 4-(dimethylamino)benzoate, 2-phenyl-3H-benzimidazole-5-sulfonic acid, 5-benzoyl-4-hydroxy-2-methoxybenzene-1-sulfonic acid, 2-hydroxy-N,N-bis(2-hydroxyethyl)ethan-1-aminium 2-hydroxybenzoate, or a combination thereof.

12. The composition of claim 1, wherein the broad spectrum UV absorber component comprises particles of a size between 500 and 9000 nanometers in diameter.

13. The composition of claim 1, wherein the additive component comprises vitamin E, sunflower lecithin, isopropyl myristate, isopropyl palmitate, vegetable glycerin, vegetable squalene, stearic acid, cetearyl alcohol, coco glucoside, starch, niacinamide, seaweed extract, iron oxide (FeO), silicate mineral, mica, or any combination thereof.

14. The composition of claim 1, wherein the composition exhibits a % strain between 0.001-25%.

15. The composition of claim 1, wherein the composition has a relative % UV absorption between 70% and 100%, a relative % visible light absorption between 3% and 7%, and a relative % near infrared light absorption between 10% and 14%.

16. The composition of claim 1, wherein the composition has a melting temperature of between 25° C. and 90° C.

17. The composition of claim 1, wherein the composition comprises
about 4.30 wt % sunflower wax, about 76.75 wt % fractionated coconut oil, about 0.20 wt % vitamin E, and about 18.75 wt % ZnO
about 4.30 wt % sunflower wax, about 71.25 wt % fractionated coconut oil, about 0.20 wt % vitamin E, about 3.50 wt % babassu starch, about 2.00 wt % seaweed extract, and about 18.75 wt % ZnO; or
about 4.30 wt % sunflower wax, about 76.95 wt % fractionated coconut oil, and about 18.75 wt % ZnO; or
about 4.30 wt % sunflower wax, about 57.71 wt % fractionated coconut oil, about 19.24 wt % Abyssinian seed oil, and about 18.75 wt % ZnO; or
about 4.30 wt % sunflower wax, about 57.71 wt % fractionated coconut oil, about 19.24 wt % apricot oil, and about 18.75 wt % ZnO; or
about 4.30 wt % sunflower wax, about 57.71 wt % fractionated coconut oil, about 19.24 wt % hemp, and about 18.75 wt % ZnO; or
about 4.30 wt % sunflower wax, about 57.71 wt % fractionated coconut oil, about 19.24 wt % sesame oil, and about 18.75 wt % ZnO.

18. A method of reducing the risk of sun damage to skin comprising applying the composition of claim 1 to the skin of a subject.

19. The composition of claim 1, wherein the composition comprises about 4.30 wt % sunflower wax, about 71.25 wt % fractionated coconut oil, about 0.20 wt % vitamin E, about 3.50 wt % babassu starch, about 2.00 wt % seaweed extract, and about 18.75 wt % ZnO.

20. The composition of claim 1, wherein the composition comprises about 4.30 wt % sunflower wax, about 76.95 wt % fractionated coconut oil, and about 18.75 wt % ZnO.

21. The composition of claim 1, wherein the composition comprises between 0.1 wt % and 10 wt % sunflower wax, between 50 wt % and 90 wt % fractionated coconut oil, between 0 wt % and 20 wt % vitamin E, and between 10 wt % and 30 wt % ZnO.

22. The composition of claim 1, wherein the composition comprises between 0.1 wt % and 10 wt % sunflower wax, between 50 wt % and 90 wt % fractionated coconut oil, between 0 wt % and 20 wt % vitamin E, between 0 wt % and 20 wt % babassu starch, between 0 wt % and 20 wt % seaweed extract, and between 10 wt % and 30 wt % ZnO.

23. The composition of claim 1, wherein the wax component comprises sunflower wax, the oil component comprises fractionated coconut oil, and the broad spectrum UV absorber comprises ZnO.

24. The composition of claim 23, wherein the additive component comprises vitamin E.

25. The composition of claim 24, wherein the additive component further comprises babassu starch and seaweed extract.

26. The composition of claim 23, wherein the composition comprises 0.5 wt % to 8 wt % sunflower wax, 65 wt % to 85 wt % fractionated coconut oil, and 12 wt % to 25 wt % ZnO.

27. The composition of claim 16, wherein the composition has a melting temperature of between 60° C. and 90° C.

* * * * *